US012773411B2

(12) United States Patent
Keene et al.

(10) Patent No.: US 12,773,411 B2
(45) Date of Patent: Oct. 27, 2026

(54) COMBINATION CANCER THERAPY WITH PENTAAZA MACROCYCLIC RING COMPLEX AND PLATINUM-BASED ANTICANCER AGENT

(71) Applicants: Biossil Inc., Toronto (CA); Board of Regents of the University of Texas System, Austin, TX (US)

(72) Inventors: Jeffery L. Keene, St. Louis, MO (US); Dennis P. Riley, Chesterfield, MO (US); Robert A. Beardsley, University City, MO (US); Michael Dean Story, Dallas, TX (US); Kranti Ashok Mapuskar, Iowa City, IA (US); Douglas R. Spitz, Jr., Iowa City, IA (US); Bryan G. Allen, Iowa City, IA (US); Andrew Blake Davis, Iowa City, IA (US); Diana Zepeda Orozco, Iowa City, IA (US)

(73) Assignees: Biossil Inc., Toronto (CA); Board of Regents of the University of Texas System, Austin, TX (US)

( * ) Notice: Subject to any disclaimer, the term of this patent is extended or adjusted under 35 U.S.C. 154(b) by 1109 days.

(21) Appl. No.: 16/965,476

(22) PCT Filed: Jan. 31, 2019

(86) PCT No.: PCT/US2019/016071
§ 371 (c)(1),
(2) Date: Jul. 28, 2020

(87) PCT Pub. No.: WO2019/152661
PCT Pub. Date: Aug. 8, 2019

(65) Prior Publication Data
US 2021/0338686 A1 Nov. 4, 2021

Related U.S. Application Data

(60) Provisional application No. 62/624,250, filed on Jan. 31, 2018.

(51) Int. Cl.
*A61K 31/555* (2006.01)
*A61K 33/243* (2019.01)
*A61P 35/00* (2006.01)

(52) U.S. Cl.
CPC .......... *A61K 31/555* (2013.01); *A61K 33/243* (2019.01); *A61P 35/00* (2018.01)

(58) Field of Classification Search
CPC ...... A61K 31/555; A61K 33/243; A61P 35/00
See application file for complete search history.

(56) References Cited

U.S. PATENT DOCUMENTS

| | | | |
|---|---|---|---|
| 3,930,867 | A | 1/1976 | Bigelow |
| 4,001,212 | A | 1/1977 | Richman |
| 4,702,998 | A | 10/1987 | Tanaka et al. |
| 5,096,724 | A | 3/1992 | Zenner et al. |
| 5,610,293 | A | 3/1997 | Riley et al. |
| 5,637,578 | A | 6/1997 | Riley et al. |
| 5,874,421 | A | 2/1999 | Riley et al. |
| 5,976,498 | A | 11/1999 | Newumann et al. |
| 6,040,330 | A | 3/2000 | Hausheer et al. |
| 6,084,093 | A | 7/2000 | Riley et al. |
| 6,177,419 | B1 | 1/2001 | Campbell et al. |
| 6,180,620 | B1 | 1/2001 | Salvemini |

(Continued)

FOREIGN PATENT DOCUMENTS

| | | |
|---|---|---|
| CN | 1215919 | 5/1999 |
| CN | 2870352 | 2/2007 |

(Continued)

OTHER PUBLICATIONS

Miller et al. Toxins 2010,2,2490-2518.*
Kurtin, Sandra, J Adv Pract Oncol 2012, 3: 209-224.*
Vaidya et al., Nat Biotechnol. May 2010; 28(5): 478-485.*
Du et al., Glutathione and glutaredoxin act as a backup of human thioredoxin reductase 1 to reduce thioredoxin 1 preventing cell death by aurothioglucose, J. Biol Chem, 287(45), 38210-38219 2012.

(Continued)

*Primary Examiner* — Rebecca L Anderson
(74) *Attorney, Agent, or Firm* — Bryan Cave Leighton Paisner LLP

(57) ABSTRACT

A method of treating a cancer in a mammalian subject afflicted with the cancer, consisting essentially of administering to the subject a therapeutically effective amount of a platinum-based anticancer agent, and administering to the subject a therapeutically effective amount of a pentaaza macrocyclic ring complex corresponding to the Formula (I) below, prior to, concomitantly with, or after administration of the platinum-based anticancer agent, whereby response of the cancer to the platinum-based anticancer agent is increased.

(I)

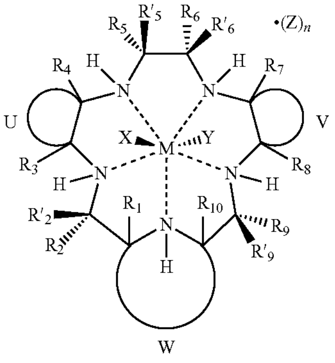

31 Claims, 16 Drawing Sheets

(56) References Cited

U.S. PATENT DOCUMENTS

| | | | |
|---|---|---|---|
| 6,204,259 | B1 | 3/2001 | Riley et al. |
| 6,214,817 | B1 | 4/2001 | Riley et al. |
| 6,245,758 | B1 | 6/2001 | Stern et al. |
| 6,395,725 | B1 | 5/2002 | Salvemini |
| 6,525,041 | B1 | 2/2003 | Neumann et al. |
| 6,781,231 | B2 | 8/2004 | Minervini |
| 6,916,799 | B2 | 7/2005 | Fridovich et al. |
| 7,102,214 | B1 | 9/2006 | Miks et al. |
| 7,166,910 | B2 | 1/2007 | Minervini |
| 7,242,089 | B2 | 7/2007 | Minervini |
| 7,407,645 | B2 | 8/2008 | Neumann et al. |
| 7,445,641 | B1 | 11/2008 | Omberg et al. |
| 7,981,421 | B2 | 7/2011 | Zhou et al. |
| 8,263,568 | B2 | 9/2012 | Slomczynska et al. |
| 8,444,856 | B2 | 5/2013 | Slomczynska et al. |
| 8,808,545 | B2 | 8/2014 | Slomczynska et al. |
| 9,149,483 | B2 | 10/2015 | Keene et al. |
| 9,642,861 | B2 | 5/2017 | Rothstein et al. |
| 9,738,669 | B2 | 8/2017 | Keene et al. |
| 9,738,670 | B2 | 8/2017 | Keene et al. |
| 9,855,279 | B2 | 1/2018 | Rothstein et al. |
| 10,137,133 | B2 | 11/2018 | Keene et al. |
| 10,493,081 | B2 | 12/2019 | Keene et al. |
| 10,597,415 | B2 | 3/2020 | Keene et al. |
| 10,610,533 | B2 | 4/2020 | Rothstein et al. |
| 11,066,433 | B2 | 7/2021 | Keene et al. |
| 11,219,614 | B2 | 1/2022 | Beardsley et al. |
| 11,246,950 | B2 | 2/2022 | Beardsley et al. |
| 2002/0072512 | A1 | 6/2002 | Salvemini |
| 2002/0128248 | A1 | 9/2002 | Salvemini |
| 2003/0050297 | A1 | 3/2003 | Crapo |
| 2004/0132706 | A1 | 7/2004 | Salvemini |
| 2004/0219138 | A1 | 11/2004 | Salvemini |
| 2005/0101581 | A1 | 5/2005 | Reading et al. |
| 2005/0171198 | A1 | 8/2005 | Salvemini |
| 2005/0175580 | A1 | 8/2005 | Salvemini |
| 2005/0222250 | A1 | 10/2005 | Rezvani |
| 2006/0081994 | A1 | 4/2006 | Craig et al. |
| 2006/0089710 | A1 | 4/2006 | Ornberg et al. |
| 2006/0140953 | A1 | 6/2006 | Newell et al. |
| 2006/0199792 | A1 | 9/2006 | Groves et al. |
| 2006/0223808 | A1 | 10/2006 | Chackalamannil et al. |
| 2007/0148154 | A1 | 6/2007 | Weill et al. |
| 2008/0161324 | A1 | 7/2008 | Johansen et al. |
| 2008/0166000 | A1 | 7/2008 | Hsiao |
| 2008/0269185 | A1 | 10/2008 | Rothstein et al. |
| 2008/0318917 | A1 | 12/2008 | Salvemini et al. |
| 2009/0131377 | A1 | 5/2009 | Salvemini |
| 2009/0221622 | A1 | 9/2009 | Teja et al. |
| 2009/0257979 | A1 | 10/2009 | Beigelman et al. |
| 2010/0304415 | A1 | 12/2010 | Slomczynska et al. |
| 2011/0136756 | A1 | 6/2011 | Keene et al. |
| 2013/0079317 | A1 | 3/2013 | Keene et al. |
| 2014/0142065 | A1 | 5/2014 | Che et al. |
| 2017/0044193 | A1 | 2/2017 | Keene et al. |
| 2018/0237462 | A1 | 8/2018 | Keene et al. |
| 2019/0151331 | A1 | 5/2019 | Beardsley et al. |
| 2019/0209524 | A1 | 7/2019 | Beardsley et al. |
| 2020/0215077 | A1 | 7/2020 | Rothstein et al. |
| 2021/0347796 | A1 | 11/2021 | Keene et al. |
| 2022/0088030 | A1 | 3/2022 | Keene et al. |
| 2022/0118119 | A1 | 4/2022 | Beardsley et al. |

FOREIGN PATENT DOCUMENTS

| | | |
|---|---|---|
| CN | 103906756 | 7/2014 |
| EA | 010834 | 12/2008 |
| EP | 0524161 | 1/1993 |
| EP | 0598753 | 3/1998 |
| EP | 2760874 | 8/2014 |
| EP | 3388082 | 10/2018 |
| JP | H06509566 | 10/1994 |
| JP | 1996040941 | 2/1996 |
| JP | 2002506445 | 2/2002 |
| JP | 2002534382 | 10/2002 |
| JP | 2003509423 | 3/2003 |
| JP | 2004507487 | 3/2004 |
| JP | 2004517113 | 6/2004 |
| JP | 2011513333 | 4/2011 |
| JP | 2011516610 | 5/2011 |
| JP | 2014526562 | 10/2014 |
| JP | 2019-131508 A | 8/2019 |
| JP | 2021-512110 A | 5/2021 |
| RU | 2313368 | 9/2011 |
| WO | 1991010645 | 7/1991 |
| WO | 1993002090 | 2/1993 |
| WO | 1994015925 | 7/1994 |
| WO | 1995028968 | 11/1995 |
| WO | 1996039396 | 12/1996 |
| WO | 1997006830 | 2/1997 |
| WO | 1998058636 | 12/1998 |
| WO | 200072893 | 12/2000 |
| WO | 2001019823 | 3/2001 |
| WO | 200158458 | 8/2001 |
| WO | 2002053142 | 7/2002 |
| WO | 2002058686 | 8/2002 |
| WO | 2002071054 | 9/2002 |
| WO | 2002100395 | 12/2002 |
| WO | 2003024434 | 3/2003 |
| WO | 2005042718 | 5/2005 |
| WO | 2006078713 | 7/2006 |
| WO | 2006083508 | 8/2006 |
| WO | 2007139897 | 12/2007 |
| WO | 2008027547 | 3/2008 |
| WO | 2008045559 | 4/2008 |
| WO | 2009111294 | 9/2009 |
| WO | 2009134616 | 11/2009 |
| WO | 2009143454 | 11/2009 |
| WO | 2011113019 | 9/2011 |
| WO | 2013048965 | 4/2013 |
| WO | 2017027728 | 2/2017 |
| WO | 2017192740 | 11/2017 |
| WO | 2018191676 | 10/2018 |

OTHER PUBLICATIONS

Fan et al., Enhancement of auranofin-induced lung cancer cell apoptosis by selenocystine, a natural inhibitor of TrxR1 in vitro and in vivo, Cell Death & Disease, 5, e1191 2018.

Kurosawa et al., Cytotoxicity induced by inhibition of thioredoxin reductases via multiple signaling pathways: Role of cytosolic phospholipase A2alpha-dependent and -independent release of arachidonic acid, Journal of Cell Physiology, 219(3): 606-616 2009.

Li et al., Auranofin-mediated inhibition of PI3K/AKT/mTOR axis and anticancer activity in non-small cell lung cancer cells. Oncotarget, 7(3): 3548-3558 2016.

Fretland et al., Superoxide Dismutase (SOD) Modulates Acetic Acid-Induced Colitis in Rodents, Gastroenterology, 1991, 100: A581 1991.

Scarbrough, P.M., Inhibitors of glucose and hydroperoxide metabolism potentiate 17AAG-induced cancer cell killing via metabolic oxidative stress, University of Iowa Theses and Dissertations 2011.

Sobhakumari et al., Susceptibility of Human Head and Neck Cancer Cells to Combined Inhibition of Glutathione and Thioredoxin Metabolism, PLOS, 7(10): e48175, 10 pgs 2012.

Newton et al., Synthesis and characterization of the Mn(II) complexof [15]aneN.sub.5, J. Coord. Chem., 1988, 19: 265-277 1988.

Bradshaw et al., A simple crab-like cyclization procedure to prepare polyaza-crowns and cyclams with one or two unsubstitute macroring Nitrogen atoms or with a Hydroxy group, J. Heterocyclic Chem, 1989, 26: 1431-1435 1989.

Krakowiak et al., Preparation of Triaza-, Tetraaza- and Peraza-Crown Compounds containing Aminoalkyl Side Groups or Unsubstituted Rin Nitrogen Atoms, J. Org. Chem, 1990, 55(10): 3364-3368 1990.

Riley et al., Stopped-flow Kinetic Analysis for Monitoring superoxide decay in aqueous systems, Analytical Biochemistry, 1991, 196: 344-349 1991.

European Patent Office, Extended Search Report for EP App. 17847659.4, 12 pages Mar. 6, 2020.

(56) References Cited

OTHER PUBLICATIONS

Eldor et al., Perturbation of endothelial functions by ionizing irradiation: effects on prostaglandins, chemoattractants and mitogens, Semin Thromb Hemost, 1989, 15(2): 215-225 1989.
Escribano et al., Aerosol Orgotein (Ontosein) for the Prevention of Radiotherapy-Induced Adverse Effects in Head and Neck Cancer Patients: A feasibility study, Neoplasma, 2002, 49(3): 201-209 2002.
Gridley et al., Chapter 16, Therapeutic Application of Superoxide Dismutase (SOD) (Salvemini and Cuzzocrea, eds.), 2004, 1-20 2004.
Guo et al., Prevention of Radiation-Induced Oral Cavity Mucositis by Plasmid/Liposome Delivery of the Human Manganese Superoxide Dismutase (SOD2) Transgene, Radiat. Red., 2003, 159(3): 361-370 2003.
Knox, et al., Chemotherapy-induced oral mucositis. Prevention and Management, Drugs Aging, 2000, 17(4): 257-267 2000.
Leussink et al., Pathways of Proximal Tubular Cell Death in Bismuth Nephrotoxicity, Toxicol. Appl. Pharmacol., 2002, 180(2): 100-109 2002.
Orrell, R.W., AEOL-10150 (Aeolus), Current Opinion Investig. Drugs, 2006, 7(1): 70-80 2006.
Peterson, D. E. Research advances in oral mucositis. Current Opinion Oncol., 1999, 11(4): 261-266 1999.
Plevova, P. Prevention and treatment of chemotherapy- and radiotherapy-induced oral mucositis: a review. Oral Oncol. 1999; 35(5): 453-470 1999.
Salvemini et al., Amelioration of Joint Disease in a Rat Model of Collagen-Induced Arthritis by M40403, a Superoxide Dismutase Mimetic, Arthritis & Rheumatism, 2001, 44: 2909-2921 2001.
Slikkerveer et al., Pharmacokinetics and Toxicity of Bismuth Compounds, Med. Toxicol. Adverse Drug Exp, 1989, 4(5): 303-323 1989.
Sonis, Oral Mucositis in Cancer Therapy, Support. Oncol., 2004, 2 (supple.3): 3-8 2004.
Sonis et al., Mitigating Effects of Interleukin 11 on Consecutive Courses of 5-Fiuorouracil-Induced Ulcerative Mucositis in Hamsters, Cytokine, 1997, 9(8): 605-612 1997.
Ahmad et al., Mitochondrial O.sub2. and H2O2 Mediate Glucose Deprivation-induced Cytotoxicity and Oxidative Stress in Human Cancer Cells, J. Bio. Chem, 2005, 280(6): 4254-4263 2005.
Sonis et al., Transforming Growth Factor-B3 Mediated Modulation of Cell Cycling and Attenuation of 5-Fiuorouracil Induced Oral Mucositis, Oral Oncol., 1997, 33(1): 47-54 1997.
Sonis et al., Defining Mechanisms of action of interleukin-11 on the progression of radiation-induced oral mucositis in hamsters, Oral Oncology, 2000, 36(4): 373-381 2000.
Cuzzocrea et al., C. Tempol, a membrane-permeable radical scavenger, reduces dinitrobenzene sulfonic acid-induced colitis, Eur J Pharmacol., 2000, 406:127-137 2001.
Salvemini et al., Reply to Role of manganese superoxide dismutase in cancer, Nature Medicine, 9(9): 1103-1103 Sep. 1, 2003.
Goodman & Gilman's The Pharmacological Basis of Therapeutics, 10th Edition, McGraw Hill, 1996 1996.
Suenderhauf et al., A Physiologically Based Pharmacokinetic Model of the Minipig: Data Compilation and Model Implementation, Pharm. Res., 2013, 30(1): 1-15 2013.
Cuzzocrea et al., Protective effects of M40401, a selective superoxide dismutase mimetic, on zymosan-induced nonseptic shock, Crit. Care Med., 2004, 21(1): 157-167 2004.
Cuzzocrea et al., Reduction in the development of Cerulein-induced acute pancreatitis by treatment with M40401, a new selective superoxide dismutase mimetic, Shock, 2004, 22(3): 254-261 2004.
Anderson, C., Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC), Oral Mucositis Research Workshop, MASCC/ISOO Annual Meeting on Supportive Care in Cancer, Copenhagen, Denmark (Jun. 25, 2015) 2015.
Cotton et al., Advanced Inorganic Chemistry, Chapter 5, "Coordination Compounds", 2nd revised edn., Interscience Publishers, 1966, 139 1966.
Cotton et al., Advanced Inorganic Chemistry, Chapter 2, "Coordination Compounds", 2nd revised edn., Interscience Publishers, 1966, 35-36, 45-49 1966.
Wang et al., Evidence of d-phenylglycine as delivering tool for improving I-dopa absorption, J. Biomed. Sci., 2010, 17: 71-79 2010.
Wikipedia, Cefalexin, retrieved Nov. 2, 2016, from en.wikipedia.org/wiki/Cefalexin, 6 pages 2016.
Hironaka et al., Quantitative Evaluation of PEPT1 Contribution to Oral Absorption of Cephalexin in Rats, Pharm. Res., 2009, 26(1): 40-50 2009.
Knütter et al., Transport of Angiotensin-Converting Enzyme Inhibitors by H+/Peptide Transporters Revisited, J. Pharma. Exp. Thera., 2008, 327(2): 432-441 2008.
Patent Cooperation Treaty, International Search Report for PCT/US2016/046599, dated Nov. 17, 2016, 5 pages Nov. 17, 2016.
Park et al., Facility case volume and outcomes for intensity-modulated radiotherapy in head and neck cancer, Department of Therapeutic Radiology, Yale School of Medicine, 1 pg. Sep. 26, 2016.
Boero et al., Importance of Radiation Oncologist Experience Among Patients With Head-and-Neck Cancer Treated With Intensity-Modulated Radiation Therapy, Journal of Clinical Oncology, 2016, 34(7): 684-696 Mar. 1, 2015.
Ferreira et al., Effect of radiotherapy delay in overall treatment time on local control and survival in head and neck cancer: Review of the literature, Reports of Practical Oncology and Radiotherapy, 2015, 20: 328-339 May 24, 2015.
Anderson et al., Phase 1b Trial of Superoxide Dismutase Mimetic GC4419 to Reduce Chemoradiotherapy-induced Oral Mucositis in Patients with Oral Cavity or Oropharyngeal Carcinoma, Multidisciplinary Head and Neck Cancer Symposium, Scottsdale, Arizona, 17 pgs Feb. 18, 2016.
Hussan et al., A review on recent advances of enteric coating, Journal of Pharmacy, 2012, 2(6): 5-11 2012.
Strickley, R. G., Solubilizing Excipience in Oral and Injectable Formulations, Pharmaceutical Research, 2004, 21 (2): 201-230 2004.
Keene, J. L., Declaration under 37 C.F.R. 1.132 May 14, 2014.
Salvemini et al., Pharmacological manipulation of the in ammatory cascade by the superoxide dismutase mimetic, M40403, British Journal of Pharmacology, 2001, 132: 815-827 2001.
Masini et al., Reduction of antigen-induced respiratory abnormalities and airway inflammation in sensitized guinea pigs by a superoxide dismutase mimetic, Free Radical Biology & Medicine, 2005, 39: 520-531 2005.
Salvemini et al., Superoxide Dismutase Mimetics, Pulmonary Pharmacology & Therapeutics, 2002, 15: 439-447 2002.
Weiss et al., Manganese-based Superoxide Dismutase Mimetics Inhibit Neutrophil Infiltration in Vivo, Journal of Biological Chemistry, 1996, 271(42): 26149-26156 1996.
Udipi et al., Modification of inflammatory response to implated biomedical materials in vivo by surface bound superoxide dismutase mimics, Journal of Biomedical Materials Research, 1999, 1-12 1999.
Riley et al., Toward the rational design of superoxide dismutase mimics: mechanistic studies for the elucidation of substituent effects on the catalytic activity of macrocyclic manganese(II) complexes, JACS, 1997, 119(28): 6522-6528.
Salvemini et al., A nonpeptidyl mimic of superoxide dismutase with therapeutic activity in rats, Science, 1999, 286: 304-306 1999.
Sishc et al., The radioprotector GC4419 ameliorates radiation induced lung fibrosis while enhancing the response of non-small cell lung cancer tumors to high dose per fraction radiation exposures, American Association of Cancer Research, 1 pg. 2018.
Sichc et al. The superoxide dismutase mimetic GC4419 enhances tumor killing when combined with stereotactic ablative radition, BioRxiv Mar. 11, 2020.
Zhu et al. Lysine 68 acetylation directs MnSOD as a tetrameric detoxification complex versus a monomeric tumor promoter, Nature Communications Jun. 3, 2019.

(56) References Cited

OTHER PUBLICATIONS

European Patent Office, Extended European Search Report for 20168046.96, 16 pages Oct. 16, 2020.
Jiang et al., Role of IL-2 in cancer immunotherapy, Oncoimmunology, 5(6); E1163462 Apr. 25, 2016.
Lasry et al., Inflammatory networks underlying colorectal cancer, Nature Immunology, 17(3):230-240 Feb. 16, 2016.
Mikirova et al., Effect of high-dose intravenous vitamin C on inflammation in cancer patients, Journal of Translational Medicine, 10(189): 2 pages 2012.
Riley et al., Manganese Macrocyclic Ligand Complexes as Mimics of Superoxide Dismutase, J. Am. Chem. Soc. 116: 387-388 1994.
Pannala et al., Mechanistic Characterization of the Thioredoxin System in the Removal of Hydrogen Peroxide, Free Radic Biol Med., 78: 42-55 2015.
Kelso et al., A Mitochondria-Targeted Macrocyclic Mn(II) Superoxide Dismutase Mimetic, Chemistry & Biology, 19: 1237-1246 2012.
European Patent Office, Extended European Search Report issued for 18785213.2, 16 pages Feb. 8, 2021.
Laurent et al. Controlling Tumor Growth by Modulating Endogenous Production of Reactive Oxygen Species, Cancer Research, 65(3): 948-956 2005.
Tovmasyan et al., Anticancer therapeutic potential of Mn porphyrin/ascorbate system, Free Radical Biology and Medicine, 89:1231-1247 2015.
Rawal et al., Manganoporphyrins Increase Ascorbate-Induced Cytotoxicity by Enhancing H2O2 Generation, Cancer Research, 73(16):5232-5241 2013.
Batinic-Haberle et al., An educational overview of the chemistry, biochemistry and therapeutic aspects of Mn porphyrins—From superoxide dismutation to H2O2-driven pathways, Redox Biology, 5:43-65 2015.
Marzano et al., Inhibition of thioredoxin reductase by auranofin induces apoptosis in cisplatin-resistant human ovarian cancer cells, Free Radical Biology & Medicine 42: 872-881 2007.
U.S. Department of Health and Human Services, Food and Drug Administration, Center for Drug Evaluation and Research (CDER), Guidance for Industry Estimating the Maximum Safe Starting Dose in Initial Clinical Trials for Therapeutics in Adult Healthy Volunteers, 30 pages 2005.
Qian et al., Advances in the study of effects of vitamin C on tumor prevention, Youjiang Medical Journal, 36(6): 741-743 2008.
Ghosh et al., A novel manganese complex, Mn-(II) N-(2-hydroxy acetophenone) glycinate overcomes multidrug-resistance in cancer, European Journal of Pharmaceutical Sciences, 49: 737-747 2013.
Serafim et al., Regulating mitochondrial respiration in cancer in: Kanner S. (eds) Tumor Metabolome Targeting and Drug Development, Cancer Drug Discovery and Development, 45 pages 2014.
Liu et al., Mechanisms of the CDK4/6 inhibitor palbociclib (PD 0332991) and its future application in cancer treatment (Review), Oncology Reports, 36: 901-911 2018.
Shadad et al., Gastrointestinal radiation injury: Symptoms, risk factors and mechanisms, World Journal of Gastroenterology, 19(2): 185-198 2013.
Yu et al., Intestinal stem cell injury and protection during cancer therapy, Transl Cancer Research, 2(5): 384-396 2013.
Anderson et al., Phase 1b/2a Trial of Superoxide (SO) Dismutase (SOD) Mimetic GC4419 to Reduce Chemoradiation Therapy-Induced Oral Mucositis (OM) in Patients With Oral Cavity or Oropharyngeal Carcinoma (OCC), Intl. J. Rad. Oncol., 2016, 94(4): 869-870 2016.
Kim et al., Antiproliferative effect of gold(I) compound auranofin through inhibition of STAT3 and telomerase activity in MDA-MB 231 human breast cancer cells, BMB Rep., 46(1): 59-64 2013.
Zou et al., Auranofin induces apoptosis by ROS-mediated ER stress and mitochondrial dysfunction and displayed synergistic lethality with piperlongumine in gastric cancer, Oncotarget, 6(34): 36505-36521 2015.
Mikirova, et al. "Effect of high-dose intravenous Vitamin C on inflammation in cancer patients," Journal of Translational Medicine 2012.
Declaration under 37 C.F.R. 1.132 of Dennis P. Riley, dated Mar. 7, 2014, and filed in U.S. Appl. No. 11/871,848, filed Mar. 3, 2014.
Declaration under 37 C.F.R. 1.132 of Douglas R. Spitz, dated Feb. 6, 2014, and filed in U.S. Appl. No. 11/871,848, filed Feb. 6, 2014.
Keene, J. L., Declaration under 37 C.F.R. 1.132 May 14, 2014 May 14, 2014.
Mikirova, et al. CAS: 158, 290966, 2012 2012.
Alexandre, et al. "Improvement of the therapeutic index of anticancer drugs by the superoxide dismutase mimic mangafodipir," Journal of the National Cancer Institute, vol. 98, No. 4, Feb. 15, 2006, pp. 236-244 Feb. 15, 2006.
Belotte, et al. "Abstract B01: Superoxide dismutase significantly reversed the development of cisplatin resistance in epithelial ovarian cancer," Acquired Resistance, Feb. 13, 2015 pp. B01-B01 Feb. 13, 2015.
Karlsson, et al."Calmangafodipir [Ca4Mn (DPDP) 5], mangafodipir (MnDPDP) and MnPLED with special reference to their SOD mimetic and therapeutic properties," Drug Discovery Today, vol. 20, No. 4, Apr. 1, 2015 Apr. 1, 2015.
Ahmed, et al. "Tempol, a Superoxide Dismutase Mimetic Agent, Ameliorates Cisplatin-Induced Nephrotoxicity through Alleviation of Mitochondrial Dysfunction in Mice," PLOS ONE, vol. 9, No. 10, Jan. 1, 2014.
Wangila, et al. "Prevention of cisplatin-induced kidney epithelial cell apoptosis with a Cu superoxide dismutase- mimetic [copper 2II (3,5-ditertiarybutylsalicylate)" 4(ethanol) 4], Toxicology In Vitro, Elsevier Science, vol. 20, No. 8 Dec. 1, 2006 pp. 1300-1312 Dec. 1, 2006.
Kobayashi, et al. "Enhancement of Anti-Cancer Activity of Cisdiaminedichloroplatinum by the Protein-Bound Polysaccharide of Coriolus Versicolor QUEL (PS-K) In Vitro," Cancer Biotherapy, vol. 9, No. 4 Jan. 1, 1994 pp. 351-358 Jan. 1, 1994.
Karlsson, et al. "First clinical expeirence with the magnetic resonance imaging contrast agent and superoxide dismutase mimetic mangafodipir as an adjunct in cancer chemotherapy-a translational study," Translational Oncology, Feb. 1, 2012 pp. 32-38 Feb. 1, 2012.
Karlsson, et al. "Superior therapeutic index of calmangafodipir in comparison to mangafodipir as a chemotherapy adjunct," Translational Oncology, Dec. 1, 2012 p. 492 Dec. 1, 2012.
Davis, et al. "Manganese Superoxide Dismutase Attenuates Cisplatin-Induced Renal Injury: Importance of Suproxide," Journal of the American Society of Nephrology, vol. 12, No. 12, Dec. 1, 2001 pp. 2683-2690 Dec. 1, 2001.
Mohanty, et al. "Abstract 2929: GC4419 enhances the response of non-small cell lung carcinoma cell lines to cisplatin and cisplatin plus radiation through a ROS-mediated pathway : Cancer Research," AACR Annual Meeting 2018, Jul. 1, 2018 pp. 1-4 Jul. 1, 2018.
Kranti, et al. "Mitochondrial Superoxide Midmutase in Cisplatin-Induced Kidney Injury," Antioxidants, vol. 10, No. 9, Aug. 24, 2021 p. 1329 Aug. 24, 2001.
Extended European Search Report for EP 19747505.6 dated Feb. 9, 2022.
Dyck et al., Immune checkpoints and their inhibition in cancer and infectious diseases, European Journal of Immunology, 47: 765-779 2017.
Galera Therapeutics, Inc., A Phase 1 Dose Escalation Study of GC4419 in Combination With Chemoradiation for Squamous Cell Cancer of the Head & Neck, NIH U.S. National Library of Medicine, ClinicalTrials.gov,, 8 pages 2013.
Mapuskar, et al. "Mitochondrial Superoxide Dismutase in Cisplatin-Induced Kidney Injury," Antioxidants, vol. 10, No. 9, Aug. 24, 2021 p. 1329 Aug. 24, 2001.
Wagner, B. A., et al., Myeloperoxidase is involved in H2O2-induced apoptosis of HL-60 human leukemia cells, J. Biol. Chem, 2000, 272(29), 22461-9.
Chen, Q., et al., Pharmacologic ascorbic acid concentrations selectively kill cancer cells: action as a pro-drug to deliver hydrogen peroxide to tissues, PNAS, 2005, 102(38), 13604-9.

(56) References Cited

OTHER PUBLICATIONS

Alexandre, J., et al., Novel Action of Paclitaxel against Cancer Cells: Bystander Effect Mediated by Reactive Oxygen Species, Cancer Research, 2007, 67(8), 3512-3517.
Muscoli, C., et al., On the selectivity of superoxide dismutase mimetics and its importance in pharmacological studies, British Journal of Pharmacology, 2003, 140(3), 445-460.
Sawyer, D. T. et al., How super is superoxide?, Acc. Chem. Res., 1981, 14, 393-400.
Li, S., et al., The Role of Cellular Glutathione Peroxidase Redox Regulation in the Suppression of Tumor Cell Growth by Manganese Superoxide Dismutase, Cancer Res., 2000, 60(14), 3927-3939.
Buettner, G. R., et al., A New Paradigm: Manganese Superoxide Dismutase Influences the Production of H2O2 in Cells and Thereby Their Biological State, Free Radical Biology and Medicine, 2006, 41(8), 1338-50.
Day, B. J., Catalase and glutathione peroxidase mimics, Biochem Pharmacol, 2009, 77(3), 285-296.
Day, B. J et al., Manganic Porphyrins Possess Catalase Activity and Protect Endothelial Cells against Hydrogen Peroxide-Mediated Injury, Arch. Biochem. & Biophysics, 1997, 347(2), 256-262.
Oberley, L. W., Mechanism of the tumor suppressive effect of MnSOD overexpression, Biomedicine & Pharmacotherapy, 2005, 59, 143-48 Mar. 19, 2005.
Rocklage et al., Manganese(II) N ,N'-Dipyridoxylethylenediamine-N , N'-diacetate 5,5'-Bis(phosphate). Synthesis and Characterization of a Paramagnetic Chelate for Magnetic Resonance Imaging Enhancement, Inorg. Chem., 1989, 28, 477-485 Sep. 29, 1988.
European Patent Office, Extended Search Report issued for 12835035.2, dated Mar. 9, 2015.
Masini et al., Prevention of antigen-induced early obstruction reaction by inhaled M40419 in actively sensitized guinea-pigs, American Journal of Respiratory and Critical Case Medicine, American Lung Associations, New York, NY, Jan. 1, 2002.
Mccarthy, A., Metaphore Pharmaceuticals, Chemistry & Biology, 2003, 10(12): 1139-1140.
Macarthur et al., Modulation of serum cytokine levels by a novel superoxide dismutase mimetic, M40401, in an *Escherichia coli* model of septic shock: Correlation with preserved circulating catecholamines, Crit. Care Med., 2003, 31(1): 237245.
Aston et al., Computer-Aided Design (CAD) of Mn(II) Complexes: Superoxide Dismutase Mimetics with Catalytic Activity Exceeding the Native Enzyme, Inorg. Chem., 2001, 40: 1779-1789.
Salvemini et al., Nonpeptidyl mimetics of superoxide dismutase in clinical therapies for diseases, Cell and Mol Life Sci, 2000, 57: 1489-1492.
Macarthur et al., Inactivation of catecholamines by superoxide gives new insights on the pathogenesis of septic shock, PNAS, 2000, 97(17): 9753-9758.
Riley, P.A., Free radicals in biology: oxidative stress and the effects of ionizing radiation, Int. J. Radiat. Biol, 1994, 65 (1): 27-33.
Shimizu et al., Neurprotection against hypoxia-ischemia in neonatal rat brain by novel superoxide dismutase mimetics, Neuroscience Letters, 2003, 346: 41-44.
Tuder et al., Oxidative Stress and Apoptosis Interact and Cause Emphysema Due to Vascular Endothelial Growth Factor Receptor Blockade, Am. J. Respir. Cell Mol. Biol., 2003, 29: 88-97.
Fike et al., Reactive oxygen species from NADPH oxidase contribute to altered pulmonary vascular responses in piglets with chronic hypoxia-induced pulmonary hypertension, 2008, 295(5): L881-L888.
Batinic-Haberle et al., The ortho effect makes manganese(III) meso-tetrakis(N-methylpyridinium-2-yl)porphyrin a powerful and potentially useful superoxide dismutase mimic, J Biol Chem, 1998, 273: 24521-24528.
Batinic-Haberle et al., Pure MnTBAP selectively scavenges peroxynitrite over superoxide: , Free Radic Biol Med, 2009, 46:192-201.
Day et al., Metalloporphyrins are potent inhibitors of lipid peroxidation, Free Radic Biol Med, 1999, 26: 730-736.
Day et al., A metalloporphyrin superoxide dismutase mimetic protects against paraquat-induced endothelial cell injury, in vitro, J Pharmacol Exp Ther, 1995, 275: 1227-1232.
Ferrer-Sueta et al., Reactions of Manganese Porphyrins with Peroxynitrite and Carbonate Radical Anion, J Biol Chem, 2003, 278: 27432-27438.
Kachadourian et al., Flavin-dependent antioxidant properties of a new series of meso-N,N'-dialkyl-imidazolium substituted manganese(III) porphyrins, Biochem Pharmacol, 2004, 67:77-85.
Szabo et al., Evaluation of the relative contribution of nitric oxide and peroxynitrite to the suppression of mitochondrial respiration in immunostimulated macrophages using a manganese, FEBS Letters, 1996, 381:82-86.
Murphy et al., Efficacy of Superoxide Dismutase Mimetic M40403 in Attenuating Radiation-Induced Oral Mucositis in Hamsters, Clin Cancer Res, 2008, 14(13): 4292-4297.
Salvemini et al., A nonpeptidyl mimic of superoxide dismutase with therapeutic activity in rats, Science, 1999, 286: 304-306.
Thompson et al., The manganese superoxide dismutase mimetic, M40403, protects adult mice from lethal total body irradiation, Free Radical Research, 2010; 44(5): 529-540.
Tovmasyan et al., Radiation-Mediated tumor growth inhibition is significantly enhanced with redox-active compounds that cycle with ascorbate, Antioxidants and Redox Signaling, 29(13): 1196-1214 Nov. 1, 2018.
Patent Cooperation Treaty, International Search Report issued for PCT/US2012/056921 on Feb. 22, 2013, 5 pages.
Simic et al., Oxygen radicals in biology and medicine, Basic Life Sciences, 1988, vol. 49, Plenum Press, New York and London.
Weiss et al., Catalytic Efficacies of agents that dismutate superoxide, 1991, J. Cell, Biochem, Suppl. 15C, 216 Abstract C110.
Petkau, Scientific basis for the clinical use of superoxide dismutase, 1986, Cancer Treat. Rev. 13, 17.
Mccord, Superoxide dismutase: Rationale for use in ruperfusion injury and inflammation, 1986, J. Free Radicals Biol. Med, 2, 307.
Bannister et al., Aspects of the structure, function, and applications of superoxide dismutase, 1987, Crit. Rev. Biochem., 1987, 22(2): 111-180 1987.
Gryglewski et al., Superoxide anion is involved in the breakdown of endothelium-derived vascular relaxing factor, 1986, Nature, 320, 454-456.
Palmer et al., Nitric oxide release accounts for the biological activity of endothelium derived relaxing factor, 1987, Nature, 327, 523-526.
Samlowski et al., A nonpeptidyl mimic of superoxide dismutase, M40403, inhibits does-limiting hyptension associated with interleukin-2 and increases its antitumor effects, 2003, Nature Medicine, 9, 750-755.
Riley et al., Structure-activity studies and the design of synthetic superoxide dismutase (SOD) mimetics as therapeutics, 2006, Advances in Inorganic Chemistry, 59, 233-263.
Riley et al., Synthesis, characterization, and stability of manganese(II) C-Substituted 1, 4, 7, 10, 12- Pentaazacyclopentadecane complexes exhibity superoxide dismutase activity, J. Inorg. Chem. 1996, 35: 5213-5231.
Salvemini et al., M40403: Superoxied dismutase mimic, Drugs of the Future, 2000, 25(10): 1027-1033.
Salvemini et al., SOD Mimetics are coming of age, Nature Reviews, 2002, 1: 367-374.
Aykin-Burns et al., Increased levels of superoxide and H2O2 mediate the differential susceptibility of cancer cells versus normal cells to glucose deprivation, Biochem. J., 2009, 418: 29-37 2009.
Declaration under 37 C.F.R. 1.132 of Dennis P. Riley, dated Mar. 7, 2014, and filed in U.S. Appl. No. 11/871,848 on Mar. 7, 2014 Mar. 7, 2014.
Declaration under 37 C.F.R. 1.132 of Douglas R. Spitz, dated Feb. 6, 2014, and filed in U.S. Appl. No. 11/871,848 on Feb. 26, 2014 Feb. 6, 2014.
Cuzzocrea et al., Protective effects of M40403, a superoxide dismutase mimetic, in a rodent model of colitis, European Journal of Pharmacology, 2001, 432: 79-89 2001.

(56) References Cited

OTHER PUBLICATIONS

Salvemini et al., Protective effects of superoxied dismutase mimetic nd peroxynitrite decomposition catalyst in endotoxin-indueced intestinal damage, 1999, British Journal of Pharmacology, 127(3):685-692 1999.
European Patent Office, Extended European Search Report issued for App. No. 17166668.8, 11 pages Sep. 27, 2017.
Sindoni et al., Combination of immune checkpoint inhibitors and radiotherapy: Review of the literature, Critical Reviews in Oncology/Hematology, 2017, 113: 63-70 2017.
Pardoll, D. M., The blockade of immune checkpoints in cancer immunotherapy, Nat Rev Cancer, 2012. 12(4): 252-264 Mar. 22, 2012.
Jin et al., Clinical Observation on Superoxide Dismutase in Respect of Resistance to Skin Damage Resulting from Radiation, Chinese Journal of Radiological Health, 1993, 2(3): 137 1993.
Zhou et al., Experimental Study on Superoxide Dismutase for Prophylaxis and Treatment of Inflammatory Damage to Mouth Mucosa in Animals, West China Journal of Stomatology, 1996, 14(2) 1996.
Kasten et al., Potentiation of Nitric Oxide-Mediated Vascular Relaxation by SC52608, a Superoxide Dismustas Mimic, 1995.
Patent Cooperation Treaty, International Search Report for PCT/US2018/027588, 5 pages Aug. 27, 2018.
Park et al., Synthesis and SOD activity of manganese complexes of pentaaza macrocycles containing amino- and guanidino-auxiliary, Bulletin of the Korean Chemical Society, 32(10): 3787-3789 2011.
Patent Cooperation Treaty, International Search Report for PCT/US2018/018407, 6 pages Sep. 17, 2018.
Tabata et al., Ion-Pair Extraction of Metalloporphyrins into Acetonitrile for Determination of Copper(II), Anal. Chem., 68: 758-762 1996.
Mazzucotelli, et al., Determination of trace amounts of Metalloprotein Species in Marine Mussel Samples by High Performance Liquid Chromatography with Inductively Coupled Plasma Atomic Emission Spectrometric Detection, Analyst., 116: 605-608 1991.
Furuya et al., Determination of Pheophytinatoiron(III) Chlorides by Reverse Phase High Performance Liquid Chromatography, Analytical Sciences, 3: 353-357 1987.
Zhang et al., Quantitative determination of SC-68328 in dog plasma using flow injection and tandem mass spectroscopy, Journal of Mass Spectrometry, 35(3): 354-360 2000.
Sakai et al., Liquid-Chromatographic Separation and Determination of Coproporphyrins I & III in Urine, Clinical Chemistry, 29(2): 350-353 1983.
Riley, Functional Mimics of Supeoxide Dismutase Enzymes and Therapeutic Agents, Chem. Rev., 2572-2587 1999.
Berge et al., Pharmaceutical Salts, J. Pharm. Sci., 66: 1-19 1977.
European Patent Office, European Search Report issued for EP 10179542, 4 pages Aug. 5, 2011.
Patent Cooperation Treaty, International Search Report for PCT/US2017/049960, 5pgs. Feb. 21, 2019.
Fritz et al., Intravenous vitamin C and cancer: A systematic review, Integrative Cancer Therapies, 13(4): 280-300 2014.
Mcconnell et al., Ascorbate combination therapy: New tool in the anticancer toolbox?, Science Translational Medicine, 6(222): 1-3 2014.
European Patent Office, Extended European Search Report for 16835928.9, publication 3334744, 10 pgs. Feb. 4, 2019.
Cornwell et al., Glyceryl monocaprylate/caprate as a moderate skin penetration enhancer, International Journal of Pharmaceutics, 171: 243-255 1998.
Eurasian Patent Office, Search Report for 201892510, 1 page May 28, 2019.
European Patent Office, Extended Search Report for EP App. 18215666.1, 12 pages Jul. 19, 2019.
Di Paolo et al., Reduced development of experimental periodontitis by treatment with M40403, a superoxide dismutase mimetic, European Journal of Pharmacology, 51: 151-157 2005.
Mcfadden et al., M40403, a superoxide dismutase mimetic, protects cochlear hair cells from gentamicin, but not cisplatin toxicity, Toxicology and Applied Pharmacology, 186: 46-54 2003.
European Patent Office, Extended Search Report for EP App. 17793268.8, 8 pages Nov. 29, 2019.
Fath et al., Enhancement of Carboplatin-Mediated Lung Cancer Cell Killing by Simultaneous Disruption of Glutathione and Thioredoxin Metabolism, Clinical Cancer Research, 17(19): 6206-6217 2011.
Jungwirth et al., Anticancer Activity of Metal Complexes: Involvement, Antioxidants & Redox Signaling, 15(4): 1085-1127 2011.
Cao et al., Mechanisms of ferroptosis, Cell. Mol. Life Sci., 2016, 11:2195-2209 2016.
Rodman III, et al., Enhancement of Radiation Response in Breast Cancer Stem Cells by Inhibition of Thioredoxin and Glutathione Dependent Metabolism, Radiat Res., 2016, 186(4): 385-395 2016.
Raj et al., Selective killing of cancer cells by a small molecule targeting the stress response to ROS, Nature, 475: 231-234 2016.
Samlowski et al., Evaluation of a Superoxide Dismutase Mimetic as an Adjunct to Interleukin 2 Based Cancer Therapy, Madame Curie Report, 230-249 2006.
Samlowski et al., A nonpeptidyl mimic of superoxide dismutase, M40403, inhibits dose-limiting hypotension associated with interleukin-2 and increases its antitumor effects, Nature Medicine, 9:750-755 2003.
Sishc et al., Superoxide dismutase mimetic GC4419 protects against radiation induced lung fibrosis, exhibits anti-tumor effects, and enhances radiation induced cell killing, 1 pg 2015.
Sishc et al., Superoxide dismutase mimetic GC4419 sensitizes non-small cell lung cancer tumors to high dose per fraction radiation and ameliorates radiation induced lung fibrosis, 1 pg 2016.
Zhang et al. Thioredoxin reductase inhibitors: a patent review, Expert Opinion on Therapeutic Patents, 27(5): 547-556 2017.
Elting et al., The Burdens of Cancer Therapy, Cancer, 98(7): 1531-1539 2003.
Epperly et al., Manganese Superoxide Dismutase-Plasmid/Liposome (MnSOD-PL) Administration Protects Mice from Esophagitis Associated with Fractionated Radiation, Int. J. Cancer (Radiat. Oncol. Invest), 96: 221-231 2001.
Epperly et al., Intraoral Manganese Superoxide Dismutase-Plasmid/Liposome (MnSOD-PL) Radioprotective Gene Therapy Decreases Ionizing Irradiation-induced Murine Mucosal Cell Cycling and Apoptosis, In Vivo, 18:401-410 2004.
Guo et al., Gene Transfer of Human Manganese Superoxide Dismutase Protects Small Intestinal Villi From Radiation Injury, J Gastrointest Surg., 7(2): 229-235 2003.
Lalla et al., Treatment of Mucositis, Including New Medications, Palliative and Supportive Care, 12(5): 348-354 2006.
Murakami, The Chemical Society of Japan, editions, Separation of Optical Isomer quarterly journal, chemical review No. 6, Scientific Societies Press, p. 212-213 (translation) 1989.
Anderson, et al. Two-Year Tumor Outcomes of Phase 2B, Randomized, Double-Blind Trial of Avasopasem Manganese (GC4419) Versus Placebo to Reduce Severe Oral Mucositis Due to Concurrent Radiation Therapy and Cisplatin for Head and Neck Cancer Published:Jun. 17, 2022DOI:https://doi.org/10.1016/j.ijrobp.2022.06.063.
Anderson, et al. Phase IIb, Randomized, Double-Blind Trial of GC4419 Versus Placebo to Reduce Severe Oral Mucositis Due to Concurrent Radiotherapy and Cisplatin for Head and Neck Cancer, Journal of Clinical Oncology 37, No. 34 (Dec. 1, 2019) 3256-3265.
Anderson et al., Phase 1b/2a Trial of Superoxide (SO) Dismutase (SOD) Mimetic GC4419 to Reduce Chemoradiation Therapy-Induced Oral Mucositis (OM) in Patients With Oral Cavity or Oropharyngeal Carcinoma (OCC), Intl. J. Rad. Oncol., vol. 100, Issue 2, p. 427-435, Feb. 1, 2018.
ASCO Abstract Effects of GC4419 (avasopasem manganese) on chronic kidney disease in head and neck cancer patients treated with radiation and cisplatin, American Society of Clinical Oncology, 2020 2 pages.
Mapuskar, et al. Mitochondrial Superoxide Dismutase in Cisplatin-Induced Kidney Injury, Antioxidants 2021, 10, 1329 16 pages.

(56) References Cited

OTHER PUBLICATIONS

O'Leary, et al. Loss of SOD3 (EcSOD) Expression Promotes an Aggressive Phenotype in Human Pancreatic Ductal Adenocarcinoma, Downloaded from www.clincancerres.aacrjournals.org on Jul. 17, 2020 pp. 1741-1751.
Sishc, et al. Avasopasem manganese synergizes with hypofractionated radiation to ablate tumors through the generation of hydrogen peroxide, Sci. Transl. Med. 13, May 12, 2021 pp. 1-13.
Sishc, et al. Avasopasem Manganese Protects Against Radiation Induced Oral Mucositis and Enhances the Response of Squomous Cell Carcinoma of the Head and Neck to Ionizing Radiation and Radioimmune Therapy, Astro, vol. 108, Issue 3, Suppl. S159, Nov. 1, 2020.
Sishc, et al. Abstract: The radioprotector GC4419 enhances the response of pancreatic ductal adenocarcinoma tumors to high dose per fraction radiation exposure, AACR PDAC Meeting 2019.
Steinbach, et al. Effects of GC4419 (Avasopasem Manganese) on Chronic Kidney Disease in Head and Neck Cancer Patients Treated with Radiation and Cisplatin, ASCO20 May 2020 1 pages.
Patent Cooperation Treaty, International Search Report for PCT/US2019/016071, 4pgs. May 14, 2019.
Mapuskar et al., Mitochondrial Superoxide Increases Age-Associated Susceptability of Human Dermal Fibroblasts to Radiation and Chemotherapy, Cancer Research, 77(18): 5054-5067 2017.
Atsushi Yonezawa, "Molecular mechanisms determining Molecular Mechanisms Governing Cancer-Kidney Translocation", Drug Delivery System 27-5, 2012, pp. 381-388.
Atsushi Yonezawa, "Platinum Agent-Induced Nephrotoxicity via Organic Cation Transport System", Yakugaku Zasshi, 2012, 132(11), pp. 1281-1285.
Andrianova et al., "Rapamycin Is Not Protective against Ischemic and Cisplatin-Induced Kidney Injury", Biochemistry (Moscow), 2019, vol. 84, Nos. 12-13, pp. 1502-1512.
Mcginness et al., Amelioration of Cis-Platinum Nephrotoxicity by Orgotein (Superoxide Dismutase), Physiol. Chem. & Physics 10 (1978), pp. 267-277.
Anderson, "Phase 1b/2a Trial of Superoxide Dismutase Mimetic GC4419 to Reduce Chemoradiotherapy-induced Oral Mucositis in Patients with Oral Cavity or Oropharyngeal Carcinoma", Department of Radiation Oncology, University of Iowa, Scottsdale, Arizona, 15 pages, Feb. 18-20, 2016.
Elmorsy et al., "Advances in understanding cisplatin-induced toxicity: Molecular mechanisms and protective strategies", European Journal of Pharmaceutical Sciences 203 (2024) 106939.
Fang et al., "Rapamycin alleviates cisplatin-induced ototoxicity in vivo", Biochemical and Biophysical Research Communications 448 (2014) 443-447.
Griffin et al., "Effects of Avasopasem Manganese on Cisplatin-Induced AKI and CKD", AKI Research: Seeking New Paths to Progress, Nov. 4, 2023.
Mapuskar et al., "Persistent increase in mitochondrial superoxide mediates cisplatin-induced chronic kidney disease", Redox Biology 20 (2019) 98-10.
Mapuskar et al., "Utilizing Superoxide Dismutase Mimetics to Enhance Radiation Therapy Response While Protecting Normal Tissues", Semin Radiat Oncol. Jan. 2019; 29(1) 72-80.
Mapuskar et al., Avasopasem manganese (GC4419) protects against cisplatin-induced chronic kidney disease: An exploratory analysis of renal metrics from a randomized phase 2b clinical trial in head and neck cancer patients, Redox Biology 60 (2023) 102599.
Mapuskar et al., "The antioxidant and anti-inflammatory activities of avasopasem manganese in age-associated, cisplatin-induced renal injury", Redox Biology 70 (2024) 103022.
Mukhopadhyay et al., "Mitochondrial-targeted antioxidants represent a promising approach for prevention of cisplatin-induced nephropathy", Free Radical Biology & Medicine 52 (2012) 497-506.
Pabla et al., "Cisplatin nephrotoxicity: Mechanisms and renoprotective strategies", Kidney International (2008) 73, 994-1007.
Pan et al., "Protective Effect of Metalloporphyrins against Cisplatin-Induced Kidney Injury in Mice", PLOS ONE, Jan. 2014, vol. 3 9, Issue 1, e86057.
Nishikawa et al., "Targeting superoxide dismutase to renal proximal tubule cells inhibits nephrotoxicity of cisplatin and increases the survival of cancer-bearing mice", Cancer Letters 171 (2001) 133-138.
Volarevic et al., "Molecular mechanisms of cisplatin-induced nephrotoxicity: a balance onrenoprotection and tumor toxicity", Journal of Biomedical Science (2019) 26:25.

* cited by examiner

COMBINATION CANCER THERAPY WITH PENTAAZA MACROCYCLIC RING COMPLEX AND PLATINUM-BASED ANTICANCER AGENT

This application claims priority as a 371 national phase application of PCT Patent Application PCT/US19/16071 filed on 31 Jan. 2019, which claims the benefit of priority from U.S. Patent Application No. 62/624,250 filed on 31 Jan. 2018, all of which are hereby incorporated by reference herein in their entireties.

The present disclosure generally relates to combination therapies for cancer treatment, including administration of a pentaaza macrocyclic ring complex in combination with a platinum-based anticancer agent.

Transition metal-containing pentaaza macrocyclic ring complexes having the macrocyclic ring system corresponding to Formula A have been shown to be effective in a number of animal and cell models of human disease, as well as in treatment of conditions afflicting human patients.

FORMULA A

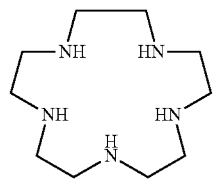

For example, in a rodent model of colitis, one such compound, GC4403, has been reported to very significantly reduce the injury to the colon of rats subjected to an experimental model of colitis (see Cuzzocrea et al., *Europ. J. Pharmacol.,* 432, 79-89 (2001)).

(4403)

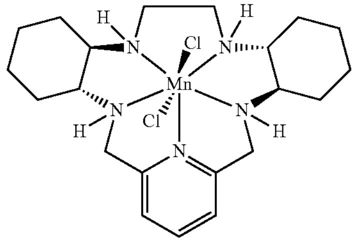

GC4403 has also been reported to attenuate the radiation damage arising both in a clinically relevant hamster model of acute, radiation-induced oral mucositis (Murphy et al., *Clin. Can. Res.,* 14(13), 4292 (2008)), and lethal total body irradiation of adult mice (Thompson et al., *Free Radical Res.,* 44(5), 529-40 (2010)). Similarly, another such compound, GC4419, has been shown to attenuate VEGFr inhibitor-induced pulmonary disease in a rat model (Tuder, et al., *Am. J. Respir. Cell Mol. Biol.,* 29, 88-97 (2003)). Additionally, another such compound, GC4401 has been shown to provide protective effects in animal models of septic shock (S. Cuzzocrea, et. al., *Crit. Care Med.,* 32(1), 157 (2004) and pancreatitis (S. Cuzzocrea, et. al., *Shock,* 22(3), 254-61 (2004)).

(4419)

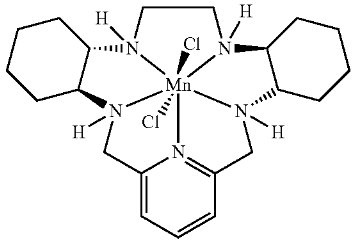

(4401)

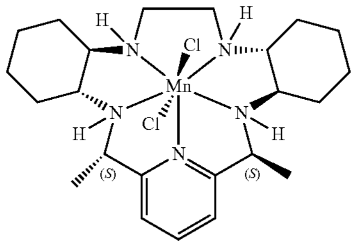

Certain of these compounds have also been shown to possess potent anti-inflammatory activity and prevent oxidative damage in vivo. For example, GC4403 has been reported to inhibit inflammation in a rat model of inflammation (Salvemini, et. al., Science, 286, 304 (1999)), and prevent joint disease in a rat model of collagen-induced arthritis (Salvemini et al., *Arthritis &Rheumatism,* 44(12), 2009-2021 (2001)). Yet others of these compounds, MdPAM and MnBAM, have shown in vivo activity in the inhibition of colonic tissue injury and neutrophil accumulation into colonic tissue (Weiss et al., *The Journal of Biological Chemistry,* 271(42), 26149-26156 (1996)). In addition, these compounds have been reported to possess analgesic activity and to reduce inflammation and edema in the rat-paw carrageenan hyperalgesia model, see, e.g., U.S. Pat. No. 6,180,620.

Compounds of this class have also been shown to be safe and effective in the prevention and treatment of disease in human subjects. For example, GC4419 has been shown to reduce oral mucositis in head-and-neck cancer patients undergoing chemoradiation therapy (Anderson, C., *Phase* 1 *Trial of Superoxide Dismutase* (*SOD*) *Mimetic GC*4419 *to Reduce Chemoradiotherapy* (*CRT*)*-Induced Mucositis* (*OM*) *in Patients* (*pts*) *with Mouth or Oropharyngeal Carcinoma* (*OCC*), Oral Mucositis Research Workshop, MASCC/ISOO Annual Meeting on Supportive Care in Cancer, Copenhagen, Denmark (Jun. 25, 2015)).

In addition, transition metal-containing pentaaza macrocyclic ring complexes corresponding to this class have shown efficacy in the treatment of various cancers. For example, certain compounds corresponding to this class have been provided in combination with agents such as paclitaxel and gemcitabine to enhance cancer therapies, such as in the treatment of colorectal cancer and lung cancer (non-small cell lung cancer) (see, e.g., U.S. Pat. No. 9,998, 893) The 4403 compound above has also been used for treatment in in vivo models of Meth A spindle cell squamous carcinoma and RENCA renal carcinoma (Samlowski et al., *Nature Medicine,* 9(6), 750-755 (2003), and has also been used for treatment in in vivo models of spindle-cell squamous carcinoma metastasis (Samlowski et al., *Madame Curie Bioscience Database* (*Internet*), 230-249 (2006)). The 4419 compound above has also been used in combination with cancer therapies, such as in combination with a therapy involving administration of cisplatin and radiation, to enhance treatment in in vivo models (Sishc et al., poster for Radiation Research Society (2015)).

Platinum-based anticancer agents such as cisplatin and oxaliplatin act by induction of DNA damage in cancer cells (Cruet-Hennequart et al, *DNA Repair,* 7(4): 582-596 (2008)), and have proven to be highly effective in cancer treatment (Kellan et al, *J. Inorg Biochem,* 77(1-2); 121-124 (1999); Wang X, *Anticancer Agents Med Chem,* 10(5): 396-411 (2010); Dilruba et al, *Cancer Chemother Pharmacol,* 77(6): 1103-1124 (2016)). However, while platinum-based anticancer agents such as cisplatin are widely used as chemotherapeutic agents, such agents also frequently have toxicities associated with the administration thereof, such as nephrotoxicity, ototoxicity, gastrotoxicity, and myelotoxicity (Miller et al., *Toxins* (*Basel*), 2(11): 2490-2518 (2010). Accordingly, the use of such platinum-based anticancer agents may be limited by the need to minimize toxic effects associated therewith.

Accordingly, a need remains for enhanced methods for cancer treatment that provide improved efficacy in the killing of cancer cells, while also providing good selectivity in the killing of cancer cells as compared to normal cells. There also remains a need for enhanced methods of treatment to improve outcomes for patients receiving these treatments. There also remains a need for methods of treatment that reduce the toxic effects associated with platinum-based anti-cancer agents such as cisplatin.

Briefly, therefore, aspects of the present disclosure are directed to a method of treating a cancer in a mammalian subject afflicted with the cancer, the method comprising administering to the subject a therapeutically effective amount of a platinum-based anticancer agent, and administering to the subject a therapeutically effective amount of a pentaaza macrocyclic ring complex corresponding to the Formula (I) below, prior to, concomitantly with, or after administration of the platinum-based anticancer agent, to increase the response of the cancer to the platinum-based anticancer agent:

(I)

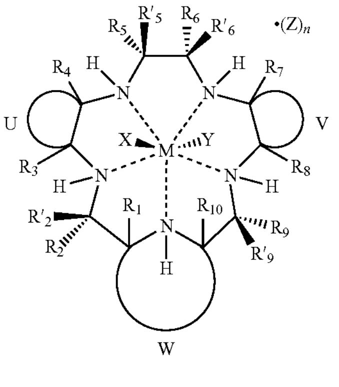

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Another aspect of the present disclosure is directed to a method of increasing the sensitivity of a mammalian subject to treatment with a platinum-based anti-cancer agent in a subject in need thereof, the method comprising:

administering to the subject a therapeutically effective amount of a pentaaza macrocyclic ring complex corresponding to the Formula (I) below, prior to, concomitantly with, or after administration of the platinum-based anticancer agent, to increase the treatment response to the platinum-based anti-cancer agent:

(I)

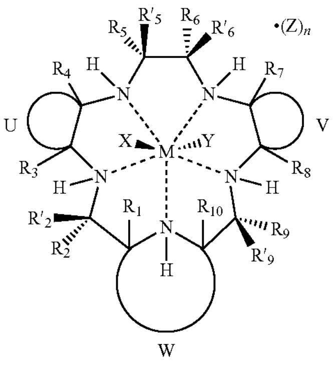

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —P(O)

$(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Another aspect of the present disclosure is directed to a method of reducing toxic effects to a mammalian subject associated with treatment with a platinum-based anti-cancer agent in a subject in need thereof, the method comprising:

administering to the subject a therapeutically effective amount of a platinum-based anticancer agent; and administering to the subject a therapeutically effective amount of a pentaaza macrocyclic ring complex corresponding to the Formula (I) below, prior to, concomitantly with, or after administration of the platinum-based anticancer agent, to reduce toxic effects of the platinum-based anti-cancer agent:

(I)

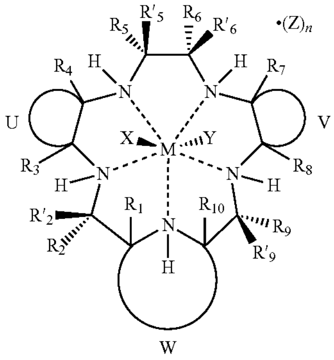

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Another aspect of the present disclosure is directed to a method of treating and/or reducing the risk for a toxic effect associated with treatment with a platinum-based anti-cancer agent in a mammalian subject in need thereof, the method comprising:

administering to the subject a pentaaza macrocyclic ring complex corresponding to the Formula (I) below, prior to, concomitantly with, or after administration of the platinum-based anticancer agent, to reduce toxic effects of the platinum-based anti-cancer agent:

(I)

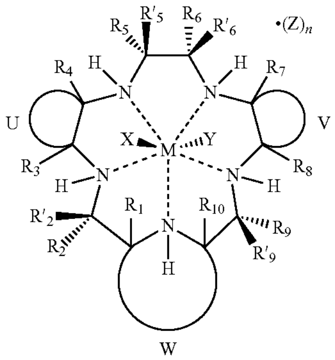

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Other objects and features will be in part apparent and in part pointed out hereinafter.

ABBREVIATIONS AND DEFINITIONS

Figure 1:
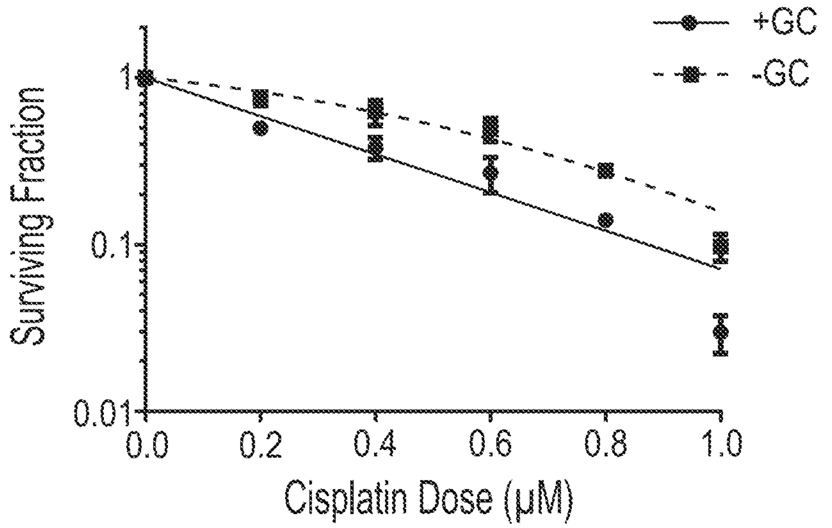
FIG. 1 shows an effect of GC4419 on survival of H460 cells in culture.

The following definitions and methods are provided to better define the present invention and to guide those of ordinary skill in the art in the practice of the present invention. Unless otherwise noted, terms are to be understood according to conventional usage by those of ordinary skill in the relevant art.

"Acyl" means a —COR moiety where R is alkyl, haloalkyl, optionally substituted aryl, or optionally substituted heteroaryl as defined herein, e.g., acetyl, trifluoroacetyl, benzoyl, and the like.

"Acyloxy" means a —OCOR moiety where R is alkyl, haloalkyl, optionally substituted aryl, or optionally substituted heteroaryl as defined herein, e.g., acetyl, trifluoroacetyl, benzoyl, and the like.

"Alkoxy" means a —OR moiety where R is alkyl as defined above, e.g., methoxy, ethoxy, propoxy, or 2-propoxy, n-, iso-, or tert-butoxy, and the like.

"Alkyl" means a linear saturated monovalent hydrocarbon moiety such as of one to six carbon atoms, or a branched saturated monovalent hydrocarbon moiety, such as of three to six carbon atoms, e.g., $C_1$-$C_6$ alkyl groups such as methyl, ethyl, propyl, 2-propyl, butyl (including all isomeric forms), pentyl (including all isomeric forms), and the like.

Moreover, unless otherwise indicated, the term "alkyl" as used herein is intended to include both "unsubstituted alkyls" and "substituted alkyls," the latter of which refers to alkyl moieties having substituents replacing a hydrogen on one or more carbons of the hydrocarbon backbone. Indeed, unless otherwise indicated, all groups recited herein are intended to include both substituted and unsubstituted options.

The term "$C_{x-y}$" when used in conjunction with a chemical moiety, such as alkyl and aralkyl, is meant to include groups that contain from x to y carbons in the chain. For example, the term $C_{x-y}$ alkyl refers to substituted or unsubstituted saturated hydrocarbon groups, including straight chain alkyl and branched chain alkyl groups that contain from x to y carbon atoms in the chain.

"Alkylene" means a linear saturated divalent hydrocarbon moiety, such as of one to six carbon atoms, or a branched saturated divalent hydrocarbon moiety, such as of three to six carbon atoms, unless otherwise stated, e.g., methylene, ethylene, propylene, 1-methylpropylene, 2-methylpropylene, butylene, pentylene, and the like.

"Alkenyl" a linear unsaturated monovalent hydrocarbon moiety, such as of two to six carbon atoms, or a branched saturated monovalent hydrocarbon moiety, such as of three to six carbon atoms, e.g., ethenyl (vinyl), propenyl, 2-propenyl, butenyl (including all isomeric forms), pentenyl (including all isomeric forms), and the like.

"Alkaryl" means a monovalent moiety derived from an aryl moiety by replacing one or more hydrogen atoms with an alkyl group.

"Alkenylcycloalkenyl" means a monovalent moiety derived from an alkenyl moiety by replacing one or more hydrogen atoms with a cycloalkenyl group.

"Alkenylcycloalkyl" means a monovalent moiety derived from a cycloalkyl moiety by replacing one or more hydrogen atoms with an alkenyl group.

"Alkylcycloalkenyl" means a monovalent moiety derived from a cycloalkenyl moiety by replacing one or more hydrogen atoms with an alkyl group.

"Alkylcycloalkyl" means a monovalent moiety derived from a cycloalkyl moiety by replacing one or more hydrogen atoms with an alkyl group.

"Alkynyl" means a linear unsaturated monovalent hydrocarbon moiety, such of two to six carbon atoms, or a branched saturated monovalent hydrocarbon moiety, such as of three to six carbon atoms, e.g., ethynyl, propynyl, butynyl, isobutynyl, hexynyl, and the like.

"Alkoxy" means a monovalent moiety derived from an alkyl moiety by replacing one or more hydrogen atoms with a hydroxy group.

"Amino" means a —$NR^aR^b$ group where $R^a$ and $R^b$ are independently hydrogen, alkyl or aryl.

"Aralkyl" means a monovalent moiety derived from an alkyl moiety by replacing one or more hydrogen atoms with an aryl group.

"Aryl" means a monovalent monocyclic or bicyclic aromatic hydrocarbon moiety of 6 to 10 ring atoms e.g., phenyl or naphthyl.

"Cycle" means a carbocyclic saturated monovalent hydrocarbon moiety of three to ten carbon atoms.

"Cycloalkyl" means a cyclic saturated monovalent hydrocarbon moiety of three to ten carbon atoms, e.g., cyclopropyl, cyclobutyl, cyclopentyl, or cyclohexyl, and the like.

"Cycloalkylalkyl" means a monovalent moiety derived from an alkyl moiety by replacing one or more hydrogen atoms with a cycloalkyl group, e.g., cyclopropylmethyl, cyclobutylmethyl, cyclopentylethyl, or cyclohexylethyl, and the like.

"Cycloalkylcycloalkyl" means a monovalent moiety derived from a cycloalkyl moiety by replacing one or more hydrogen atoms with a cycloalkyl group.

"Cycloalkenyl" means a cyclic monounsaturated monovalent hydrocarbon moiety of three to ten carbon atoms, e.g., cyclopropenyl, cyclobutenyl, cyclopentenyl, or cyclohexenyl, and the like.

"Cycloalkenylalkyl" means a monovalent moiety derived from an alkyl moiety by replacing one or more hydrogen atoms with a cycloalkenyl group, e.g., cyclopropenylmethyl, cyclobutenylmethyl, cyclopentenylethyl, or cyclohexenylethyl, and the like.

"Ether" means a monovalent moiety derived from an alkyl moiety by replacing one or more hydrogen atoms with an alkoxy group.

"Halo" means fluoro, chloro, bromo, or iodo, preferably fluoro or chloro.

"Heterocycle" or "heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group is a saturated ring and is not fused to aryl or heteroaryl ring as stated above, it is also referred to herein as saturated monocyclic heterocyclyl.

"Heteroaryl" means a monovalent monocyclic or bicyclic aromatic moiety of 5 to 10 ring atoms where one or more, preferably one, two, or three, ring atoms are heteroatom selected from N, O, or S, the remaining ring atoms being carbon. Representative examples include, but are not limited to, pyrrolyl, pyrazolyl, thienyl, thiazolyl, imidazolyl, furanyl, indolyl, isoindolyl, oxazolyl, isoxazolyl, benzothiazolyl, benzoxazolyl, benzimidazolyl, quinolinyl, isoquinolinyl, pyridinyl, pyrimidinyl, pyrazinyl, pyridazinyl, triazolyl, tetrazolyl, and the like.

"Nitro" means —$NO_2$.

"Organosulfur" means a monovalent moiety a —SR group where R is hydrogen, alkyl or aryl.

"Platinum based anticancer agent" refers to the class of compounds having anti-cancer effects that are coordination complexes of platinum, and that may also be referred to as platins, platinates, and platinum-based antineoplastic agents. Examples of platinum-based anticancer agents used in chemotherapy include cisplatin, oxaliplatin, carboplatin, nedaplatin, lobaplatin, heptaplatin, dicycloplation, lipoplatin, LA-12, phosphaplatin, phenanthriplatin, ProLindac, triplatin tetranitrate, picoplatin, satraplatin and/or pharmaceutically acceptable salts thereof.

"Substituted alkyl," "substituted cycle," "substituted phenyl," "substituted aryl," "substituted heterocycle," and "substituted nitrogen heterocycles" means an alkyl, cycle, aryl, phenyl, heterocycle or nitrogen-containing heterocycle, respectively, optionally substituted with one, two, or three substituents, such as those independently selected from alkyl, alkoxy, alkoxyalkyl, halo, hydroxy, hydroxyalkyl, or organosulfur. Generally, the term "substituted" includes groups that are substituted with any one or more of $C_{1-4}$alkyl, $C_{2-4}$alkenyl, halogen, alcohol and/or amine.

"Thioether" means a monovalent moiety derived from an alkyl moiety by replacing one or more hydrogen atoms with an —SR group wherein R is alkyl.

As used herein, (i) the compound referred to herein and in the Figures as compound 401, 4401 or GC4401 is a reference to the same compound, (ii) the compound referred to herein and in the Figures as compound 403, 4403 or GC4403 is a reference to the same compound, (iii) the compound referred to herein and in the Figures as compound 419, 4419 or GC4419 is a reference to the same compound, and (iv) the compound referred to herein and in the Figures as compound 444, 4444 or GC4444 is a reference to the same compound.

Furthermore, the use of the term "consisting essentially of," in referring to a method of treatment, means that the method substantially does not involve providing another therapy and/or another active agent in amounts and/or under conditions that would be sufficient to provide the treatment, and which are other than the therapies and/or active agents specifically recited in the claim. Similarly, the use of the term "consisting essentially of," in referring to a kit for treatment, means that the kit substantially does not include another therapy and/or another active agent provided in amounts and/or under conditions that would be sufficient to provide the treatment, and which are other than the therapies and/or active agents specifically recited in the claim.

DETAILED DESCRIPTION

In one embodiment, aspects of the present disclosure are directed to the treatment of cancer by administration of a therapeutically effective amount of a pentaaza macrocyclic ring complex according to Formula (I), described below, in combination with a therapeutically effective amount of a platinum-based anticancer agent, to a subject suffering from cancer, to provide treatment of the cancer. The pentaaza macrocyclic ring complexes may be administered prior to, concomitantly with, or after administration of the platinum-based anticancer agent, to increase response of the cancer to the platinum-based anti-cancer agent. In particular, it has unexpectedly been discovered that the pentaaza macrocyclic ring complex according to Formula (I) exhibits synergistic effects when administered in combination with the platinum-based anti-cancer agent, to produce a more-than-additive effect as compared to administration of either the platinum-based anti-cancer agent and/or pentaaza macrocyclic ring complex according to Formula (I) alone. Without being limited by any specific theory, it is believed that the pentaaza macrocyclic ring complex according to Formula (I) may act to sensitize cancer cells to treatment with the platinum-based anti-cancer agent, such that the cancer cells become highly responsive to the anti-cancer effects of the platinum-based anti-cancer agent. Furthermore, again without being limited by any particular theory, it has been discovered that the platinum-based anti-cancer agents may be capable of acting to kill cancer cells in combination with pentaaza macrocyclic ring complexes according to Formula (I) via a previously unknown mechanism of action involving hydrogen peroxide, which mechanism is synergistically enhanced by the combination. Further discussion of the synergy between the pentaaza macrocyclic ring complex according to Formula (I) and the platinum-based anti-cancer agents is provided in the Examples described herein.

Accordingly, in one aspect of the present disclosure, a method of increasing the sensitivity of a mammalian subject to treatment with a platinum-based anti-cancer agent in a subject in need thereof is provided. The method can comprise administering to the subject a therapeutically effective amount of a pentaaza macrocyclic ring complex corresponding to the Formula (I) below, prior to, concomitantly with, or after administration of the platinum-based anticancer agent, to increase the treatment response to the platinum-based anticancer agent.

Yet another aspect of the present disclosure relates to the discovery that administration of the pentaaza macrocyclic ring complex corresponding to Formula (I) below can reduce the toxic effects of platinum-based anticancer agents, such as for example nephrotoxicity and myelotoxicity. Accordingly, in one embodiment a method of reducing toxic effects to a mammalian subject associated with treatment with a platinum-based anti-cancer agent in a subject in need thereof comprises administering to the subject a therapeutically effective amount of a platinum-based anticancer agent, and administering to the subject a therapeutically effective amount of a pentaaza macrocyclic ring complex corresponding to the Formula (I) below, prior to, concomitantly with, or after administration of the platinum-based anticancer agent, to reduce toxic effects of the platinum-based anti-cancer agent. In yet another embodiment, a method of treating and/or reducing the risk for a toxic effect associated with treatment with a platinum-based anti-cancer agent in a mammalian subject in need thereof is provided that comprises administering to the subject a pentaaza macrocyclic ring complex corresponding to the Formula (I) below, prior to, concomitantly with, or after administration of the platinum-based anticancer agent, to reduce toxic effects of the platinum-based anti-cancer agent.

In one embodiment, the subject may be one that is at risk for a toxic effect associated with treatment with a platinum-based anti-cancer agent, by virtue of their receiving the platinum-based anti-cancer agent as a part of a treatment regimen. For example, the subject may be receiving the platinum-based anti-cancer agent as a part of a regimen for cancer treatment, and thus may be at risk for development of toxic effects associated with the platinum-based anti-cancer agent while receiving the cancer treatment. In another embodiment, the subject may be also and/or alternatively be one who is currently suffering from toxic effects associated with the platinum-based anti-cancer agents, such as nephrotoxicity, myelotoxicity and/or other toxicities. It has been discovered that, in certain embodiments, the administration of the pentaaza macrocyclic ring complex corresponding to Formula (I) can mitigate, alleviate and/or otherwise treat conditions associated with platinum-based anti-cancer agent toxicities, and may even be able to reduce the subject's risk of developing conditions associated with such toxicities. Accordingly, the pentaaza macrocyclic ring complex according to Formula (I) below may, in certain embodiments, be capable of reducing the toxicity of platinum-based anti-cancer agents without substantially reducing the effectiveness of the platinum-based anticancer agents. Further, in certain embodiments, the reduced toxicity provided by the combination can even result simultaneously in an enhancement in treatment response of cancer to the platinum-based anti-cancer agent. That is, the combination may be capable of simultaneously and synergistically sensitizing cancer cells to killing with the platinum-based anti-cancer agent, while also reducing the toxic effects to normal (non-cancerous cells) of the platinum-based anti-cancer agent.

Transition Metal Pentaaza Macrocyclic Ring Complex

In one embodiment, the pentaaza macrocyclic ring complex corresponds to the complex of Formula (I):

(I)

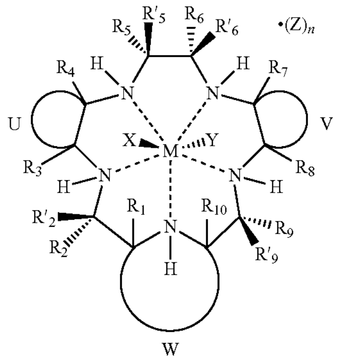

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $—OR_{11}$, $—NR_{11}R_{12}$, $—COR_{11}$, $—CO_2R_{11}$, $—CONR_{11}R_{12}$, $—SR_{11}$, $—SOR_{11}$, $—SO_2R_{11}$, $—SO_2NR_{11}R_{12}$, $—N(OR_{11})(R_{12})$, $—P(O)(OR_{11})(OR_{12})$, $—P(O)(OR_{11})(R_{12})$, and $—OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

As noted above in connection with the pentaaza macrocyclic ring complex of Formula (I), M is $Mn^{2+}$ or $Mn^{3+}$. In one particular embodiment in which the pentaaza macrocyclic ring complex corresponds to Formula (I), M is $Mn^{2+}$. In another particular embodiment in which the pentaaza macrocyclic ring complex corresponds to Formula (I), M is $Mn^{3+}$.

In the embodiments in which one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are hydrocarbyl, for example, suitable hydrocarbyl moieties include, but are not limited to alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and aralkyl. In one embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, or heterocyclyl. More preferably in this embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl (e.g., $C_1$-$C_6$ alkyl, more typically $C_1$-$C_4$ alkyl). Thus, for example, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ may be independently hydrogen, methyl, ethyl, propyl, or butyl (straight, branched, or cyclic). In one preferred embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl.

In one preferred embodiment in which the pentaaza macrocyclic ring complex corresponds to Formula (I), $R_1$, $R_2$, $R'_2$, $R_3$, $R_4$, $R_5$, $R'_5$, $R_7$, $R_8$, $R_9$, $R'_9$, and $R_{10}$ are each hydrogen and one of $R_6$ and $R'_6$ is hydrogen and the other of $R_6$ and $R'_6$ is methyl. In this embodiment, for example, $R_1$, $R_2$, $R'_2$, $R_3$, $R_4$, $R_5$, $R'_5$, $R_6$, $R_7$, $R_8$, $R_9$, $R'_9$, and $R_{10}$ may each be hydrogen while $R'_6$ is methyl. Alternatively, for example, $R_1$, $R_2$, $R'_2$, $R_3$, $R_4$, $R_5$, $R'_5$, $R'_6$, $R_7$, $R_8$, $R_9$, $R'_9$, and $R_{10}$ may each be hydrogen while $R_6$ is methyl. In another preferred embodiment in which the pentaaza macrocyclic ring complex corresponds to Formula (I), $R_1$, $R_3$, $R_4$, $R_5$, $R'_5$, $R'_6$, $R_7$, $R_8$, and $R_{10}$ are each hydrogen, one of $R_2$ and $R'_2$ is hydrogen and the other of $R_2$ and $R'_2$ is methyl, and one of $R_9$ and $R'_9$ is hydrogen and the other of $R_9$ and $R'_9$ is methyl. In this embodiment, for example, $R_1$, $R'_2$, $R_3$, $R_4$, $R_5$, $R'_5$, $R_7$, $R_8$, $R_9$, and $R_{10}$ may each be hydrogen while $R_2$ and $R'_9$ are methyl. Alternatively, for example, $R_1$, $R_2$, $R_3$, $R_4$, $R_5$, $R'_5$, $R_7$, $R_8$, $R'_9$, and $R_{10}$ may each be hydrogen while $R'_2$ and $R_9$ are methyl. In another embodiment in which the pentaaza macrocyclic ring complex corresponds to Formula (I), $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

In certain embodiments the U and V moieties are independently substituted or unsubstituted fused cycloalkyl moieties having 3 to 20 ring carbon atoms, more preferably 4 to 10 ring carbon atoms. In a particular embodiment, the U and V moieties are each trans-cyclohexanyl fused rings.

In certain embodiments the W moiety is a substituted or unsubstituted fused heteroaromatic moiety. In a particular embodiment, the W moiety is a substituted or unsubstituted fused pyridino moiety. Where W is a substituted fused pyridino moiety, for example, the W moiety is typically substituted with a hydrocarbyl or substituted hydrocarbyl moiety (e.g., alkyl, substituted alkyl) at the ring carbon atom positioned para to the nitrogen atom of the heterocycle. In a one preferred embodiment, the W moiety is an unsubstituted fused pyridino moiety.

As noted above, X and Y represent suitable ligands which are derived from any monodentate or polydentate coordinating ligand or ligand system or the corresponding anion thereof (for example benzoic acid or benzoate anion, phenol or phenoxide anion, alcohol or alkoxide anion). For example, X and Y may be selected from the group consisting of halo, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, among other possibilities. In one embodiment, X and Y if present, are independently selected from the group consisting of halo, nitrate, and bicarbonate ligands. For example, in this embodiment, X and Y, if present, are halo ligands, such as chloro ligands.

Furthermore, in one embodiment X and Y correspond to —O—C(O)—$X_1$, where each $X_1$ is —C($X_2$)($X_3$)($X_4$), and each $X_1$ is independently substituted or unsubstituted phenyl or —C(—$X_2$)(—$X_3$)(—$X_4$);

each $X_2$ is independently substituted or unsubstituted phenyl, methyl, ethyl or propyl;

each $X_3$ is independently hydrogen, hydroxyl, methyl, ethyl, propyl, amino, —$X_5$C(═O)$R_{13}$ where $X_5$ is NH or O, and $R_{13}$ is C1-C18 alkyl, substituted or unsubstituted aryl or C1-C18 aralkyl, or —$OR_{14}$, where $R_{14}$ is C1-C18 alkyl, substituted or unsubstituted aryl or C1-C18 aralkyl, or together with $X_4$ is (═O); and each $X_4$ is independently hydrogen or together with $X_3$ is (═O).

In yet another embodiment, X and Y are independently selected from the group consisting of charge-neutralizing anions which are derived from any monodentate or polydentate coordinating ligand and a ligand system and the corresponding anion thereof; or X and Y are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$.

In the pentaaza macrocyclic ring complex corresponding to Formula (I), Z is a counterion (e.g., a charge-neutralizing anion), wherein n is an integer from 0 to 3. In general, Z may correspond to counterions of the moieties recited above in connection for X and Y.

In combination, among certain preferred embodiments are pentaaza macrocyclic ring complexes corresponding to Formula (I) wherein M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl;

U and V are each trans-cyclohexanyl fused rings;

W is a substituted or unsubstituted fused pyridino moiety;

X and Y are ligands; and

Z, if present, is a charge-neutralizing anion.

More preferably in these embodiments, M is $Mn^{2+}$; $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl; U and V are each trans-cyclohexanyl fused rings; W is an unsubstituted fused pyridino moiety; and X and Y are independently halo ligands (e.g., fluoro, chloro, bromo, iodo). Z, if present, may be a halide anion (e.g., fluoride, chloride, bromide, iodide).

In yet another embodiment, the pentaaza macrocyclic ring complex is represented by Formula (II) below:

(II)

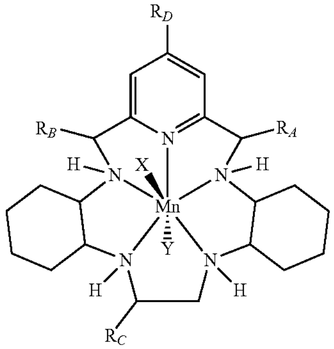

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —N($OR_{11}$)($R_{12}$), —P(O)($OR_{11}$)($OR_{12}$), —P(O)($OR_{11}$)($R_{12}$), and —OP(O)($OR_{11}$)($OR_{12}$), wherein $R_{11}$ and $R_{12}$ are independently hydrogen or alkyl.

Furthermore, in one embodiment, the pentaaza macrocyclic ring complex is represented by Formula (III) or Formula (IV):

(III)

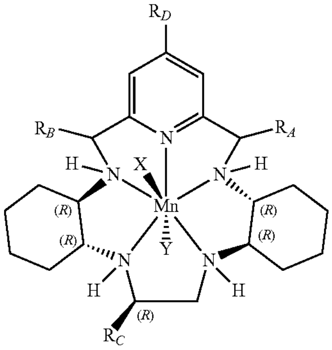

(IV)

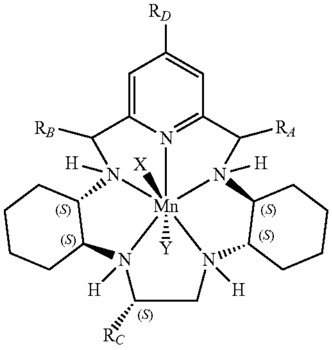

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —N($OR_{11}$)($R_{12}$), —P(O)($OR_{11}$)($OR_{12}$), —P(O)($OR_{11}$)($R_{12}$), and —OP(O)($OR_{11}$)($OR_{12}$), wherein $R_{11}$ and $R_{12}$ are independently hydrogen or alkyl.

In yet another embodiment, the pentaaza macrocyclic ring complex is a compound represented by a formula selected from the group consisting of Formulae (V)-(XVI):

-continued
(V)
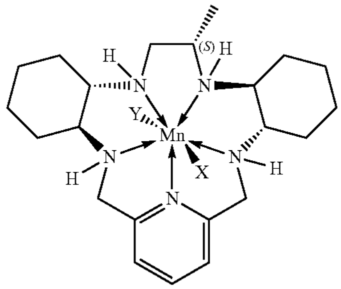
(VI)
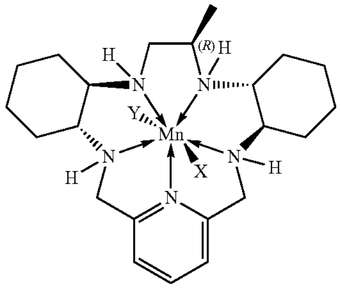
(VII)
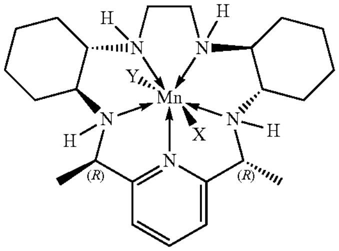
(VIII)
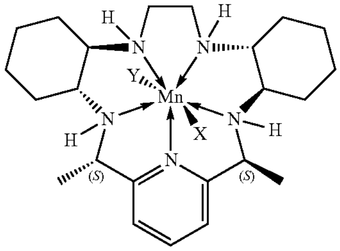
(IX)
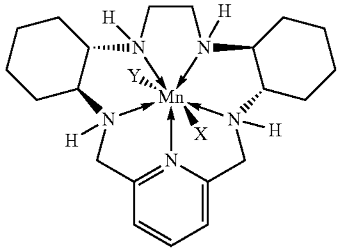
(X)
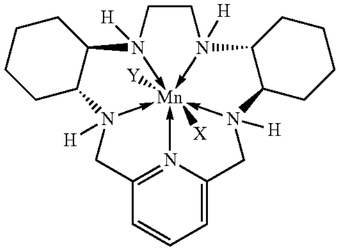
(XI)
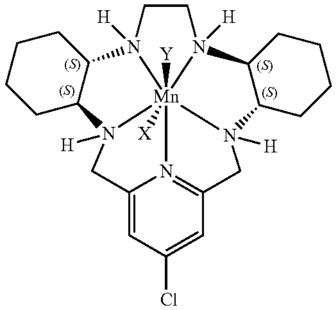
(XII)
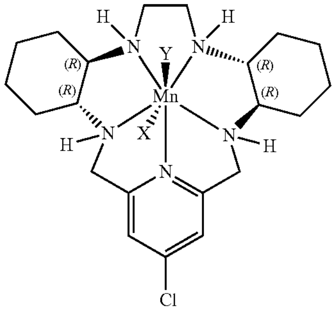
(XIII)
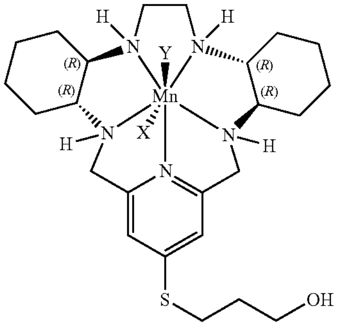
(XIV)
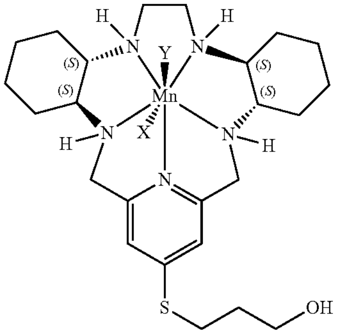
(XV)
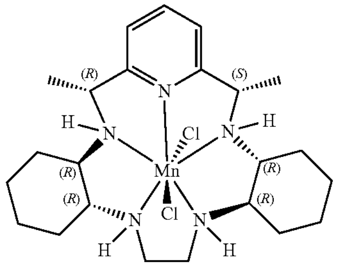

-continued (XVI)

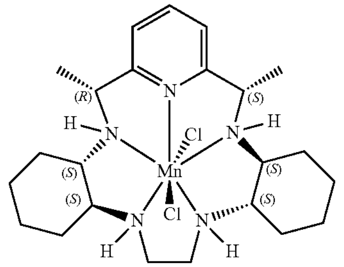

In one embodiment, X and Y in any of the formulae herein are independently selected from the group consisting of fluoro, chloro, bromo and iodo anions. In yet another embodiment, X and Y in any of the formulae herein are independently selected from the group consisting of alkyl carboxylates, aryl carboxylates and arylalkyl carboxylates. In yet another embodiment, X and Y in any of the formulae herein are independently amino acids.

In one embodiment, the pentaaza macrocyclic ring complex has the following Formula (IA):

(IA)

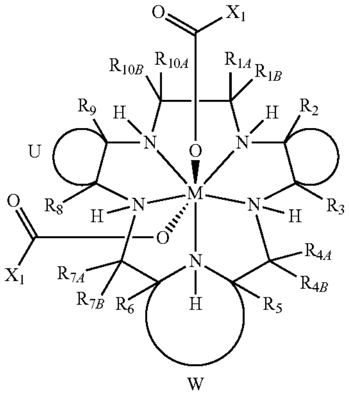

wherein

M is $Mn^{2+}$ or $Mn^{3+}$;

$R_{1A}$, $R_{1B}$, $R_2$, $R_3$, $R_{4A}$, $R_{4B}$, $R_5$, $R_6$, $R_{7A}$, $R_{7B}$, $R_8$, $R_9$, $R_{10A}$, and $R_{10B}$ are independently hydrogen, hydrocarbyl, substituted hydrocarbyl, heterocyclyl, an amino acid side chain moiety, or a moiety independently selected from the group consisting of $—OR_{11}$, $—NR_{11}R_{12}$, $—COR_{11}$, $—CO_2R_{11}$, $—C(═O)NR_{11}R_{12}$, $—SR_{11}$, $—SOR_{11}$, $—SO_2R_1$, $—SO_2NR_{11}R_{12}$, $—N(OR_{11})(R_{12})$, $—P(═O)(OR_1)(OR_{12})$, $—P(═O)(OR_{11})(R_{12})$, and $—OP(═O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_5$ and $R_6$ attached to the carbon atoms which are both part of the heterocycle and the macrocycle are absent; wherein each $X_1$ is independently substituted or unsubstituted phenyl or $—C(—X_2)(—X_3)(—X_4)$;

each $X_2$ is independently substituted or unsubstituted phenyl or alkyl;

each $X_3$ is independently hydrogen, hydroxyl, alkyl, amino, $—X_5C(═O)R_{13}$ where $X_5$ is NH or O, and $R_{13}$ is $C_1$-$C_{18}$ alkyl, substituted or unsubstituted aryl or $C_1$-$C_{18}$ aralkyl, or $—OR_{14}$, where $R_{14}$ is $C_1$-$C_{18}$alkyl, substituted or unsubstituted aryl or $C_1$-$C_{18}$ aralkyl, or together with $X_4$ is (═O);

each $X_4$ is independently hydrogen or together with $X_3$ is (═O); and the bonds between the transition metal M and the macrocyclic nitrogen atoms and the bonds between the transition metal M and the oxygen atoms of the axial ligands $—OC(═O)X_1$ are coordinate covalent bonds.

In one embodiment, within Formula (IA), and groups contained therein, in one group of compounds $X_1$ is $—C(—X_2)(—X_3)(—X_4)$ and each $X_2$, $X_3$, and $X_4$, in combination, corresponds to any of the combinations identified in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | ═O ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | =O ($X_3$ and $X_4$ in combination) | |

Furthermore, within embodiment (IA), and groups contained therein, in one group of compounds $X_1$ is $—C(—X_2)(—X_3)(—X_4)$, and $X_3$ is $—X_5C(═O)R_{13}$, such that the combinations of $X_2$, $X_3$ and $X_4$ include any of the combinations identified in the following table:

| Combination | $X_2$ | $X_3$ | $X_4$ |
|---|---|---|---|
| 1 | Ph | $NHC(═O)R_{13}$ | H |
| 2 | Ph | $OC(═O)R_{13}$ | H |
| 3 | $CH_3$ | $NHC(═O)R_{13}$ | H |
| 4 | $CH_3$ | $OC(═O)R_{13}$ | H |

where $R_{13}$ is $C_1$-$C_{18}$ alkyl, substituted or unsubstituted aryl or $C_1$-$C_{18}$ aralkyl, or $—OR_{14}$, where $R_{14}$ is $C_1$-$C_{18}$ alkyl, substituted or unsubstituted aryl or $C_1$-$C_{18}$ aralkyl.

In one embodiment, the pentaaza macrocyclic ring complex corresponding to Formula (IA) is one of the complexes Formula (IE), such as ($IE_{R1}$), ($IE_{R2}$), ($IE_{R2}$), ($IE_{R3}$), or ($IE_{S3}$):

($IE_{R1}$)

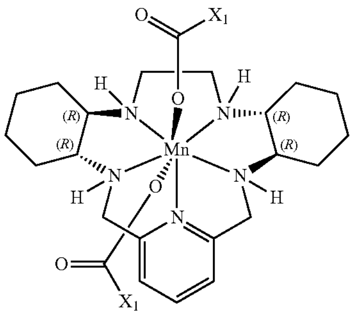

($IE_{S1}$)

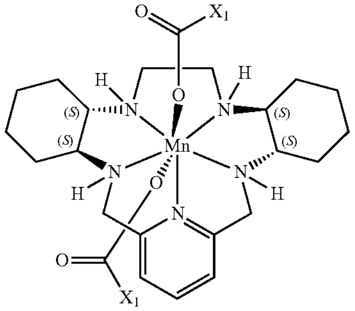

($IE_{R2}$)

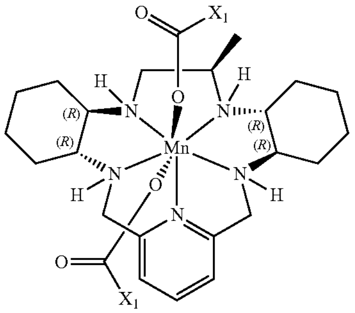

($IE_{S2}$)

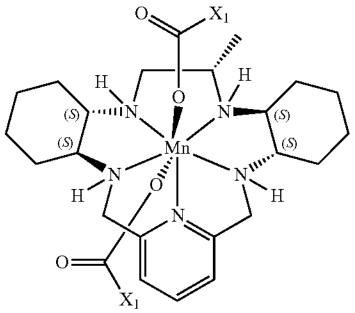

($IE_{R3}$)

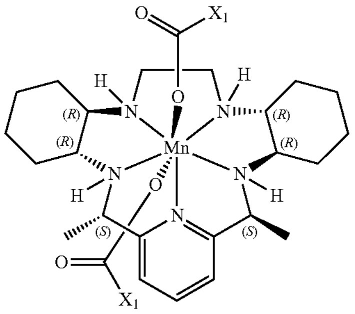

-continued ($IE_{S3}$)

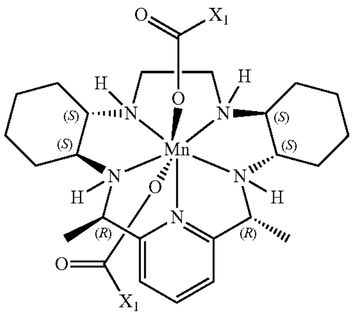

wherein

M is $Mn^{+2}$ or $Mn^{+3}$;

each $X_1$ is independently substituted or unsubstituted phenyl or —$C(X_2)(X_3)(X_4)$;

each $X_2$ is independently substituted or unsubstituted phenyl, methyl, ethyl, or propyl;

each $X_3$ is independently hydrogen, hydroxyl, methyl, ethyl, propyl, amino, or together with $X_4$ is ═O;

each $X_4$ is independently hydrogen or together with $X_3$ is ═O; and the bonds between the manganese and the macrocyclic nitrogen atoms and the bonds between the manganese and the oxygen atoms of the axial ligands —$OC(O)X_1$ are coordinate covalent bonds.

In one embodiment, each $X_1$ is —$C(X_2)(X_3)(X_4)$ and each —$C(X_2)(X_3)(X_4)$ corresponds to any of combinations 1 to 9 appearing in the table for Formula (IA) above.

In yet another embodiment, the X and Y in pentaaza macrocyclic ring complex of Formula (I) correspond to the ligands in Formulas (IA) or (IE). For example, X and Y in the complex of Formula (I) may correspond to —O—C(O)—$X_1$, where $X_1$ is as defined for the complex of Formula (IA) and (IE) above.

In one embodiment, the pentaaza macrocyclic ring complexes corresponding to Formula (I) (e.g., of Formula (I) or any of the subsets of Formula (I) corresponding to Formula (II)-(XIV), (IA) and (IE)), can comprise any of the following structures:

(4419)

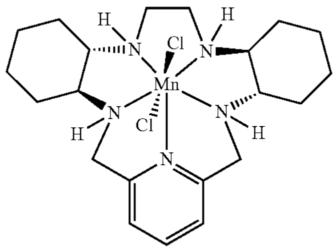

(4403)

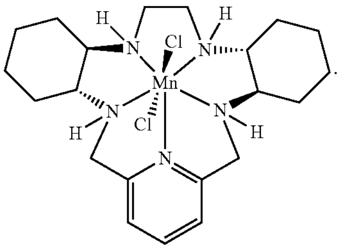

-continued
(4401)
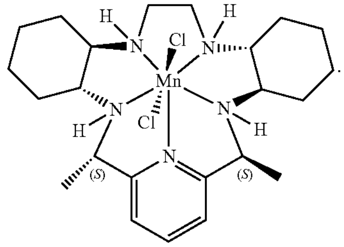
GC4444
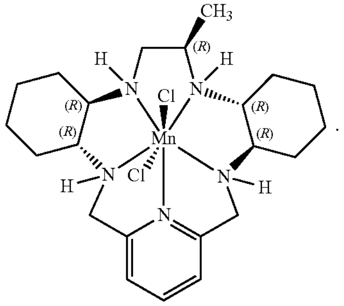
GC4702
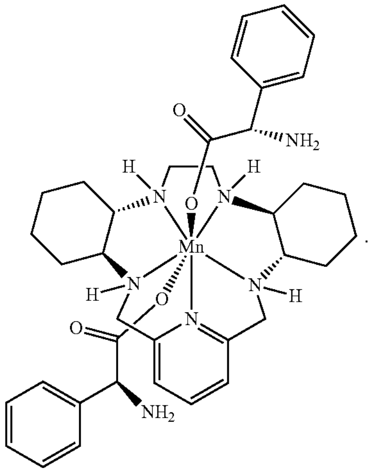
GC4711
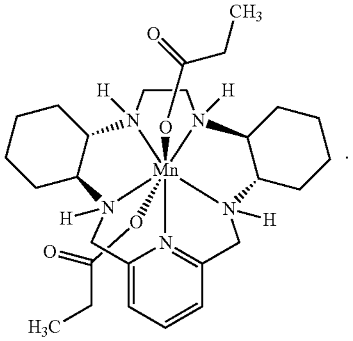
In one embodiment, the pentaaza macrocyclic ring complexes for use in the methods and compositions described herein include those corresponding to Formulae (2), (3), (4), (5), (6), and (7):
2
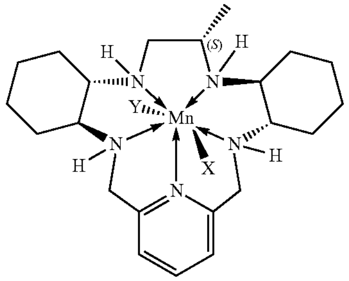
3
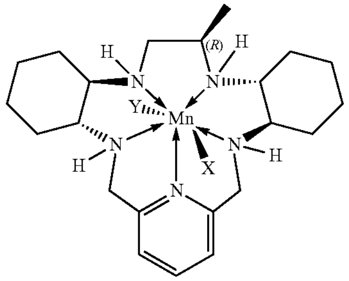
4
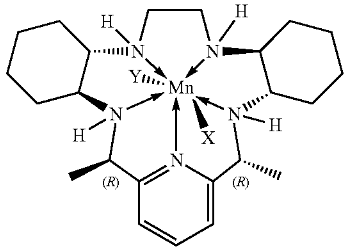
5
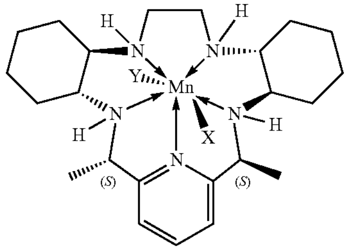
6
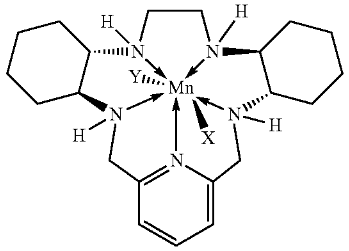
7
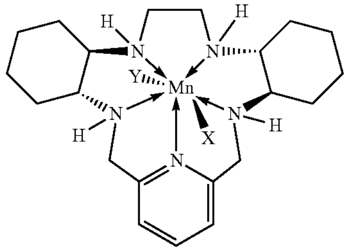

wherein X and Y in each of Formulae (2), (3), (4), (5), (6), and (7) are independently ligands. For example, according to one embodiment, the pentaaza macrocyclic ring complex for use in the methods and compositions described herein include those corresponding to Formulae (2), (3), (4), (5), (6), and (7) with X and Y in each of these formulae being halo, such as chloro. Alternatively, X and Y may be ligands other than chloro, such as any of the ligands described above.

In another embodiment, the pentaaza macrocyclic ring complex corresponds to Formula (6) or Formula (7):

6

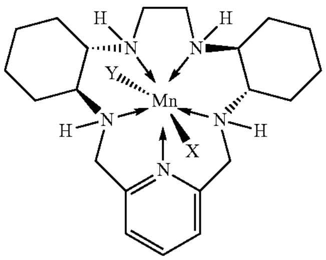

7

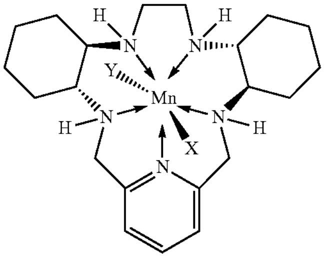

The chemical structures of 6 (such as the dichloro complex form described, for example, in Riley, D. P., Schall, O. F., 2007, Advances in Inorganic Chemistry, 59:233-263) and of 7 herein (such as the dichloro complex form of 7), are identical except that they possess mirror image chirality; that is, the enantiomeric structures are non-superimposable.

For example, the pentaaza macrocyclic ring complex may correspond to at least one of the complexes below:

(4403)

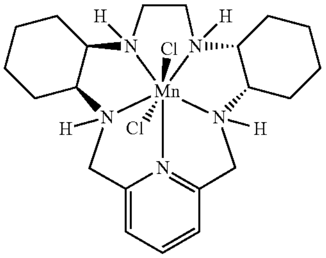

-continued (4419)

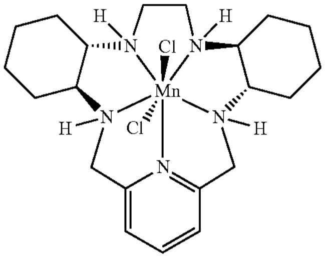

In yet another embodiment, the pentaaza macrocyclic ring complex may correspond to at least one of the complexes below, and/or an enantiomer thereof:

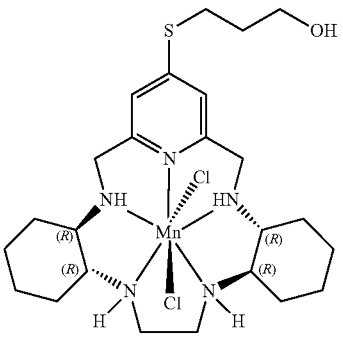

(4432)

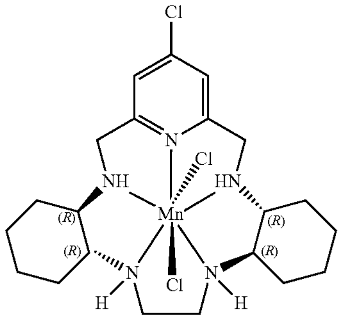

In one embodiment, the enantiomeric purity of the pentaaza macrocyclic ring complex is greater than 95%, more preferably greater than 98%, more preferably greater than 99%, and most preferably greater than 99.5%. As used herein, the term "enantiomeric purity" refers to the amount of a compound having the depicted absolute stereochemistry, expressed as a percentage of the total amount of the depicted compound and its enantiomer. In one embodiment, the diastereomeric purity of the pentaaza macrocyclic ring complex is greater than 98%, more preferably greater than 99%, and most preferably greater than 99.5%. As used herein, the term "diastereomeric purity" refers to the amount of a compound having the depicted absolute stereochemistry, expressed as a percentage of the total amount of the depicted compound and its diastereomers. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC). Similarly, enantiomeric purity can be determined by any analytical method capable of quantitatively distinguishing between a compound and its enantiomer. Examples of suitable analytical methods for determining enantiomeric purity include, without limitation, optical rotation of plane-polarized light using a polarimeter, and HPLC using a chiral column packing material.

In one embodiment, a therapeutically effective amount of the pentaaza macrocyclic ring complex may be an amount sufficient to provide a peak plasma concentration of at least 0.1 μM when administered to a patient. For example, in one embodiment, the pentaaza macrocyclic ring complex may be administered in an amount sufficient to provide a peak plasma concentration of at least 1 μM when administered to a patient. In yet another embodiment, the pentaaza macrocyclic ring complex may be administered in an amount sufficient to provide a peak plasma concentration of at least 10 μM when administered to a patient. Generally, the pentaaza macrocyclic ring complex will not be administered in an amount that would provide a peak plasma concentration greater than 40 μM when administered to a patient. For example, the pentaaza macrocyclic ring complex may be administered in an amount sufficient to provide a peak plasma concentration in the range of from 0.1 μM to 40 μM in a patient. As another example, the pentaaza macrocyclic ring complex may be administered in an amount sufficient to provide a peak plasma concentration in the range of from 0.5 μM to 20 μM in a patient. As another example, the pentaaza macrocyclic ring complex may be administered in an amount sufficient to provide a peak plasma concentration in the range of from 1 μM to 10 μM in a patient.

In yet another embodiment, a dose of the pentaaza macrocyclic ring complex that is administered per kg body weight of the patient may be at least 0.1 mg/kg, such as at least 0.2 mg/kg. For example, the dose of the pentaaza macrocyclic ring complex that is administered per kg body weight of the patient may be at least 0.5 mg/kg. As another example, the dose of the pentaaza macrocyclic ring complex that is administered per kg body weight of the patient may be at least 1 mg/kg. In another example, the pentaaza macrocyclic compound that is administered per kg body weight may be at least 2 mg/kg, such as at least 3 mg/kg, and even at least about 15 mg/kg, such as at least 24 mg/kg and even at least 40 mg/kg. Generally, the dose of the pentaaza macrocyclic ring complex that is administered per kg body weight of the patient will not exceed 1000 mg/kg. For example the dose of the pentaaza macrocyclic ring complex that is administered per kg body weight of the patient may be in the range of from 0.1 to 1000 mg/kg, such as from 0.2 mg/kg to 40 mg/kg, such as 0.2 mg/kg to 24 mg/kg, and even 0.2 mg/kg to 10 mg/kg. As another example, the dose of the pentaaza macrocyclic ring complex that is administered per kg body weight may be in a range of from 1 mg/kg to 1000 mg/kg, such as from 3 mg/kg to 1000 mg/kg, and even from 5 mg/kg to 1000 mg/kg, such as 10 mg/kg to 1000 mg/kg. As another example, the dose of the pentaaza macrocyclic ring complex that is administered per kg body weight may be in a range of from 2 mg/kg to 15 mg/kg. As yet another example, the dose of the pentaaza macrocyclic ring complex that is administered per kg body weight may be in a range of from 3 mg/kg to 10 mg/kg. As another example, the dose of the pentaaza macrocyclic ring complex that is administered per kg body weight of the patient may be in the range of from 0.5 to 5 mg/kg. As yet a further example, the dose of the pentaaza macrocyclic ring complex that is administered per kg body weight of the patient may be in the range of from 1 to 5 mg/kg.

In one embodiment, the dosages and/or plasma concentrations discussed above may be particularly suitable for the pentaaza macrocyclic ring complex corresponding to GC4419, although they may also be suitable for other pentaaza macrocyclic ring complexes. In addition, one or ordinary skill in the art would recognize how to adjust the dosages and/or plasma concentrations based on factors such as the molecular weight and/or activity of the particular compound being used. For example, for a pentaaza macrocyclic ring complex having an activity twice that of GC4419, the dosage and/or plasma concentration may be halved, or for a pentaaza macrocyclic ring complex having a higher molecular weight that GC4419, a correspondingly higher dosage may be used.

The dosing schedule of the pentaaza macrocyclic ring complex can similarly be selected according to the intended treatment. For example, in one embodiment, a suitable dosing schedule can comprise dosing a patient at least once per week, such as at least 2, 3, 4, 5, 6 or 7 days per week (e.g., daily), during a course of treatment. As another example, in one embodiment, the dosing may be at least once a day (qd), or even at least twice a day (bid). In one embodiment, the course of treatment with the pentaaza macrocyclic ring complex may last at least as long as a course of treatment with a platinum-based anti-cancer agent, such as cisplatin, and may even exceed the duration during which the platinum-based anticancer agent is provided. The course of therapy with the pentaaza macrocyclic ring complex may also start on the same date as treatment with the platinum-based anticancer agent, or may start sometime after initial dosing with the platinum-based anti-cancer agent, as is discussed in more detail below. For example, in one embodiment, for platinum-based anticancer agent that is administered for a course of therapy lasting at least a day, two days, three days, four days, five days, six days, one week, two weeks, three weeks, a month, two months, three months, four months, five months, six months, the pentaaza macrocyclic ring complex may be administered for a course of therapy lasting at least at least a day, two days, three days, four days, five days, six days, one week, two weeks, three weeks, a month, two months, three months, four months, five months, six months.

Platinum-Based Anti-Cancer Agent

According to one embodiment, a platinum-based anti-cancer agent is provided as a part of the treatment method(s) herein, in combination with the pentaaza macrocyclic compound. Platinum-based anti-cancer agents include the class of compounds that are coordination complexes of platinum, and that have anti-cancer effects. Platinum-based anticancer agents such as cisplatin and oxaliplatin have been understood to provide anti-cancer effects by induction of DNA damage in cancer cells (Cruet-Hennequart et al, *DNA Repair,* 7(4): 582-596 (2008)), and have proven to be highly effective in cancer treatment (Kelland et al, *J. Inorg Biochem,* 77(1-2); 121-124 (1999); Wang X, *Anticancer Agents Med Chem,* 10(5): 396-411 (2010); Dilruba et al, *Cancer Chemother Pharmacol,* 77(6): 1103-1124 (2016); Johnstone et al., *Anticancer Res,* 34(1): 471-476 (2014)). The platinum-based anticancer compounds can comprise platinum(II) complexes such as cisplatin, carboplatin and oxaliplatin, and may also comprise platinum(IV) complexes such as satraplatin and LA-12 (see, e.g., Bouchal et al. *Proteome Science,* 9:68 (2011). The platinum-based anti-cancer agent may be provided in various formulations, and may also be provided as a part of a delivery vesicle or other targeting moiety for targeting tumors and/or cancerous cells, such as for example with the platinum-based anticancer agent ProLindac (AP5346), which is a DACH (diaminocyclohexane) platinum polymer prodrug that uses a 25 kDa polymer delivery vehicle based on hydroxypropylmethacrylamide (HPMA) to target oxaliplatin to tumors (see, e.g., Nowotnik et al., *Advanced Drug Delivery Reviews,* 61(13): 1214-1219 (2009). Other targeting mechanisms for targeting and/or enhancing delivery of the platinum-based anticancer agent to tumors and/or cancerous cells can include, for example, peptides, polymer carriers, micelles, radiation and/or photoactivated prodrugs, functionalized carbon nanotubes and/or nanorods, hollow Prussian Blue, magnetic iron oxide and/or gold nanoparticles, and nanogels (see, e.g., Butler et al., *Current Opinion in Chemical Biology,* 17(2): 175-188 (2013).

In one embodiment, suitable platinum-based anticancer agents can be selected from the group consisting of cisplatin, carboplatin, oxaliplatin, nedaplatin, lobaplatin, heptaplatin, dicycloplation, lipoplatin, LA-12 ((OC-6-43)-bis(acetato)(1-adamantylamine)amminedichloroplatinum (IV)), phosphaplatin, phenanthriplatin, ProLindac (AP5346), triplatin tetranitrate, picoplatin, satraplatin, pyriplatin and/or a pharmaceutically acceptable salt thereof.

The dose of the platinum-based anticancer agent can be selected according to the treatment to be provided and the particular platinum-based anticancer agent being used. For example, a suitable dose of a platinum-based anti-cancer agent such as cisplatin may be in a range from 10 $mg/m^2$ to 200 $mg/m^2$, such as 20 $mg/m^2$ to 100 $mg/m^2$.

The dosing schedule of the platinum-based anti-cancer agent can similarly be selected according to the intended treatment and the platinum-based anti-cancer agent being provided. For example, in one embodiment, a suitable dosing schedule can comprise dosing a patient at a frequency of once or twice per day, two days, three days, four days, five days, six days, per week, per two weeks, per three weeks or per month.

Timing of Administration

In one embodiment, a course of therapy with the platinum-based anti-cancer agent and pentaaza macrocyclic ring complex can comprise one or multiple doses of the agent and/or complex, according to the treatment to be provided. In one embodiment, a course of therapy comprising one or multiple doses can comprise administering a dose of the pentaaza macrocyclic complex a predetermined period of time before administration of the platinum-based anticancer agent. For example, the course of therapy can comprise administering an initial dose and optionally one or more subsequent doses of the platinum-based anticancer agent, with the onset of dosing with the pentaaza macrocyclic ring complex being performed a predetermined period of time before the initial platinum-based anticancer agent dose. In another embodiment, a course of therapy comprising one or multiple doses can comprise administering a dose of the pentaaza macrocyclic complex after a predetermined period of time has elapsed since administration of an dose of a platinum-based anticancer agent. That is, the course of therapy can comprise administering an initial dose and optionally one or more subsequent doses of the platinum-based anticancer agent, with the onset of dosing with the pentaaza macrocyclic ring complex being delayed for a predetermined period of time after the initial platinum-based anticancer agent dose.

In one embodiment, at least one of the doses of the pentaaza macrocyclic ring complex during the course of therapy, is administered at least one week, at least 5 days, at least 3 days, at least 2 days, at least 1 day at least 12 hours, at least 8 hours, at least 4 hours, at least 2 hours, at least 1 hour and/or at least 30 mins before administration of the platinum-based anticancer agent. In another embodiment, the at least one of the doses of the pentaaza macrocyclic ring complex during the course of therapy, is administered at least one week, at least 5 days, at least 3 days, at least 2 days, at least 1 day at least 12 hours, at least 8 hours, at least 4 hours, at least 2 hours, at least 1 hour and/or at least 30 mins after administration of the platinum-based anticancer agent. Furthermore, the timing of the at least one dose of the pentaaza macrocyclic ring complex may also apply to a plurality of doses provided during the course of therapy, such as at least 25%, at least 50%, at least 75%, at least 90%, and even substantially all of the doses provided during the course of therapy.

Other Cancer Therapies

In one embodiment, the treatment provided herein can further comprise treatment with another therapy other than those specifically described above, such as for example one or more of a radiation therapy and/or another chemotherapeutic treatment. As yet another example, the treatment could comprise administering another anti-cancer agent such as a PARP inhibitor (poly ADP ribose polymerase inhibitor), such as for example any one or more of olaparib, rucaparib, niraparib, iniparib, talazoparib, and veliparib, before, concomitantly with, or after administration of one or more of the platinum-based anti-cancer compound and pentaaza macrocyclic ring complex. Other anti-cancer agents could also be provided. For example, in one embodiment, a radiation therapy may be administered to the subject prior to, concomitantly with, or after administration of one or more of the platinum-based anticancer agent and the pentaaza macrocyclic ring complex. Further detailed description of radiation therapies and other chemotherapies suitable for the treatment of cancer are provided below.

In one embodiment, a radiation therapy can be administered concomitantly with administration of one or more of the platinum-based anticancer agent and pentaaza macrocyclic ring complex. For example, one or more of the platinum-based anticancer agent and pentaaza macrocyclic ring complexes may be administered during a course of radiation therapy, such as in between, before or after, or on the same day as dosing with radiation, such that the subject is receiving radiation therapy concurrently with one or more of the platinum-based anticancer agent and pentaaza macrocyclic ring complex.

In yet another embodiment, the combination therapy of the pentaaza macrocyclic ring complex and platinum-based anticancer agent (e.g. cisplatin) and pentaaza macrocyclic ring complexes, can be administered in the absence of any other cancer treatment. As demonstrated further in the examples below, it has been unexpectedly discovered that the pentaaza macrocyclic ring complexes are capable of enhancing the response to and/or efficacy of platinum-based anticancer agents such as cisplatin, even when administered without radiation therapy. Accordingly, in one embodiment, the cancer treatment provided to the subject may consist essentially of the pentaaza macrocyclic ring complex and platinum-based anticancer agent, without radiation exposure (i.e. without administering a radiation dose or dose fraction). For example, the combination of the pentaaza macrocyclic ring complex and the platinum-based anticancer agent may be administered to a subject that is not receiving radiation therapy. That is, in one embodiment, the treatment comprises administering the pentaaza macrocyclic ring complex to a subject that is not receiving radiation therapy.

In yet another embodiment, the treatment comprises administering the platinum-based anticancer agent and the pentaaza macrocyclic ring complex to a subject that is not receiving radiation therapy. In yet another embodiment, where a course of therapy comprises administration of the pentaaza macrocyclic ring complex and the platinum-based anticancer agent, they are administered to a subject that does not receive radiation therapy during the course of therapy.

In one embodiment, the subject receiving the combination of pentaaza macrocyclic ring complex and platinum-based anticancer agent (e.g. cisplatin), may be one that has not been exposed to radiation (i.e., received a dose or dose fraction of radiation) for at least one day, such as at least one week, and even at least one month, and even at least 6 months, and/or that has not ever received such treatment at all before initial treatment with one or more of the pentaaza macrocyclic ring complex and the platinum-based anticancer agent. In yet another embodiment, any radiation therapy that is administered to the subject after the combination treatment with the pentaaza macrocyclic ring complex and the platinum-based anticancer agent is delayed by at least one day, such as at least one week, and even at least one month, such as at least 6 months, after a final dose of one or more of the pentaaza macrocyclic ring complex and the platinum-based anticancer agent provided during the course of the combination therapy treatment. That is, the combination therapy of the pentaaza macrocyclic ring complex and the platinum-based anticancer agent can be administered to a subject that has never before received radiation therapy, or that has received such therapy only in the distant past. Furthermore, the combination therapy of the pentaaza macrocyclic ring complex and the platinum-based anticancer agent can be administered to provide a course of treatment that does not include any exposure to radiation. As yet a further embodiment, the combination therapy of the pentaaza macrocyclic ring complex and the platinum-based anticancer agent can be provided to form a course of treatment substantially without performing any radiation therapy during or after the course of treatment, or with such radiation treatment being performed only after a significant period of time has elapsed after the course of combination treatment has ended. In one embodiment, the treatment comprises administering one or more of the pentaaza macrocyclic ring complex and the platinum-based anticancer agent to the subject on a day other than a day that the subject is receiving radiation therapy.

Methods of Administration

According to one embodiment, the platinum-based anticancer agent (e.g., cisplatin), is administered as a co-therapy or combination therapy with the pentaaza macrocyclic ring complex. Co-therapy or combination therapy according to the methods described herein is intended to embrace administration of each compound in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent, or single or multiple parenteral administrations, or other routes of administration and dosage forms. When administered in combination, therefore, the therapeutic agents (i.e., the pentaaza macrocyclic ring complex and/or the platinum-based anticancer agent) can be formulated as separate compositions that are administered at the same time or sequentially at different times, or the therapeutic agents can be given as a single composition. Pharmaceutical compositions and formulations are discussed elsewhere herein.

It is not necessary that the pentaaza macrocyclic ring complex and the platinum-based anticancer agent be administered simultaneously or essentially simultaneously; the agents and compounds may be administered in sequence. The advantage of a simultaneous or essentially simultaneous administration, or sequential administration, is well within the determination of the skilled clinician. For instance, while a pharmaceutical composition or formulation comprising platinum-based anticancer agent may be advantageous for administering first in the combination for one particular treatment, prior to administration of the pentaaza macrocyclic ring complex, prior administration of the pentaaza macrocyclic ring complex may be advantageous in another treatment. It is also understood that the instant combination of the pentaaza macrocyclic ring complex and the platinum-based anticancer agent may be used in conjunction with other methods of treating cancer (typically cancerous tumors) including, but not limited to, radiation therapy and surgery, or other chemotherapy. It is further understood that another active agent, such as a cytostatic or quiescent agent, or antiemetic agent, if any, may be administered sequentially or simultaneously with any or all of the other synergistic therapies.

Thus, embodiments of the therapeutic method include wherein a pentaaza macrocyclic ring complex and a platinum-based anticancer agent, and combinations thereof, are administered simultaneously or sequentially. For instance, aspects of the present disclosure encompass a method for the treatment of cancer wherein a pentaaza macrocyclic ring complex and a platinum-based anticancer agent are administered simultaneously or sequentially. Other active agents can also be administered simultaneously or sequentially with the pentaaza macrocyclic ring complex and the platinum-based anticancer agent.

As noted above, if the pentaaza macrocyclic ring complex and the platinum-based anticancer agent are not administered simultaneously or essentially simultaneously, then the initial order of administration of the components may be varied. Thus, for example, the platinum-based anticancer agent may be administered first, followed by the administration of the pentaaza macrocyclic ring complex; or the pentaaza macrocyclic ring complex may be administered first, followed by the administration of the platinum-based anticancer agent. This alternate administration may be repeated during a single treatment protocol. Other sequences of administration to exploit the effects described herein are contemplated, and other sequences of administration of other active agents can also be provided.

In one embodiment, the subject is pre-treated with the platinum-based anticancer agent, followed by administration of the pentaaza macrocyclic ring complex, or vice versa. In accordance with such embodiments, the pentaaza macrocyclic ring complex may be administered at least 1 hour, and even at least 3 days, after administration of the platinum-based anticancer agent, or vice versa. For example, in one embodiment, the pentaaza macrocyclic ring complex is administered between 1 hour and 3 days after administration of the platinum-based anticancer agent, or vice versa. In another embodiment, for example, the pentaaza macrocyclic ring complex is administered between 1 hour and 1 day after administration of the platinum-based anticancer agent, or vice versa. For example, the pentaaza macrocyclic ring complex may be administered within 1 hour, 2 hours, 3 hours, 4 hours, 5 hours, 6 hours, 12 hours, 18 hours, 24 hours, 36 hours, 48 hours, one week, 2 weeks, 3 weeks, 4 weeks, 6 weeks, 8 weeks, 9 weeks, 10 weeks or 12 weeks after administration of the platinum-based anticancer agent, or vice versa. In these and other embodiments, the platinum-based anticancer agent may be administered in multiple doses leading up to administration of the pentaaza macrocyclic ring complex, or vice versa.

Alternatively, the subject may be pre-treated with the pentaaza macrocyclic ring complex, followed by administration of the platinum-based anticancer agent, or vice versa. In accordance with such embodiments, the pentaaza macrocyclic ring complex may be administered within at least 1 plasma half-life of the platinum-based anticancer agent, such as within 4 plasma half-lives of the platinum-based anticancer agent, or vice versa. For example, the pentaaza macrocyclic ring complex may be administered within 1, 2, or 3 plasma half-lives of the other platinum-based anticancer agent, or vice versa.

In other alternative embodiments, the subject may be pre-treated with the platinum-based anticancer agent, followed by administration of the pentaaza macrocyclic ring complex, which is further followed by one or more additional administrations of the platinum-based anticancer agent, or vice versa. For example, the subject could be pre-treated with a dose of platinum-based anticancer agent, followed by administration of a dose of pentaaza macrocyclic ring complex, which is then followed by the administration of additional (or partial) dose of the same or different platinum-based anticancer agent, which may be further followed by another dose of pentaaza macrocyclic ring complex. Further, the subject could be pre-treated with a partial or full dose of pentaaza macrocyclic ring complex, followed by administration of a platinum-based anticancer agent, which is then followed by administration of an additional (or partial) dose of pentaaza macrocyclic complex.

As described in further detail below, the combinations of the disclosure may also be co-administered with other well known therapeutic agents that are selected for their particular usefulness against the condition that is being treated. Combinations may alternatively be used sequentially with known pharmaceutically acceptable agent(s) when a multiple combination formulation is inappropriate.

In one embodiment, the pentaaza macrocyclic ring complex and the platinum-based anticancer agent can generally be administered according to therapeutic protocols that may be known for these agents. For example, the administration of the various components can be varied depending on the disease being treated and the effects of pentaaza macrocyclic ring complex and platinum-based anticancer agent on that disease. Also, in accordance with the knowledge of the skilled clinician, the therapeutic protocols (e.g., dosage amounts and times of administration) can be varied in view of the observed effects of the administered therapeutic agents (i.e., pentaaza macrocyclic ring complex, platinum-based anticancer agent) on the patient, and in view of the observed responses of the disease to the administered therapeutic agents.

Also, in general, the pentaaza macrocyclic ring complex and the platinum-based anticancer agent do not have to be administered in the same pharmaceutical composition, and may, because of different physical and chemical characteristics, have to be administered by different routes. For example, the pentaaza macrocyclic ring complex may be administered orally to generate and maintain good blood levels thereof, while the platinum-based anticancer agent may be administered intravenously or via transfusion, or vice versa. The mode of administration may include, where possible, in the same pharmaceutical composition, or in separate pharmaceutical compositions (e.g., two or three separate compositions). Furthermore, once the initial administration has been made, then based upon the observed effects, the dosage, modes of administration and times of administration can be modified.

The particular choice of pentaaza macrocyclic ring complex and the platinum-based anticancer agent, and other related therapies (such as radiation or other chemotherapies), will depend upon the diagnosis of the attending physicians and their judgment of the condition of the patient and the appropriate treatment protocol.

Thus, in accordance with experience and knowledge, the practicing physician may modify each protocol for the administration of a component (the pentaaza macrocyclic ring complex and the platinum-based anticancer agent of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The products of which the combination are composed may be administered simultaneously, separately or spaced out over a period of time so as to obtain the maximum efficacy of the combination; it being possible for each administration to vary in its duration from a rapid administration to a relatively continuous perfusion of either component (in separate formulations or in a single formulation). As a result, for the purposes of the present disclosure, the combinations are not exclusively limited to those which are obtained by physical association of the constituents, but also to those which permit a separate administration, which can be simultaneous or spaced out over a period of time.

Accordingly, administration of the components described herein can occur as a single event or over a time course of treatment. For example, the pentaaza macrocyclic ring complex and the platinum-based anticancer agent can be administered (simultaneously or in sequence) hourly (e.g., every hour, every two hours, every three hours, every four hours, every five hours, every six hours, and so on), daily, weekly, bi-weekly, or monthly. For treatment of acute conditions, the time course of treatment may be at least several hours or days. Certain conditions could extend treatment from several days to several weeks. For example, treatment could extend over one week, two weeks, or three weeks. For more chronic conditions, treatment could extend from several weeks to several months, a year or more, or the lifetime of the patient in need of such treatment. Alternatively, the compounds and agents can be administered hourly, daily, weekly, bi-weekly, or monthly, for a period of several weeks, months, years, or over the lifetime of the patient as a prophylactic measure.

The dose or amount of pharmaceutical compositions including the pentaaza macrocyclic ring complex and the platinum-based anticancer agent administered to the patient should be an effective amount for the intended purpose, i.e., treatment or prophylaxis of one or more of the diseases, pathological disorders, and medical conditions discussed herein, particularly cancer. Generally speaking, the effective amount of the composition administered can vary according to a variety of factors such as, for example, the age, weight, sex, diet, route of administration, and the medical condition of the patient in need of the treatment. Specifically preferred doses are discussed more fully herein. It will be understood, however, that the total daily usage of the compositions described herein will be decided by the attending physician or veterinarian within the scope of sound medical judgment.

As noted above, the combinations can be co-administered (via a co-formulated dosage form or in separate dosage forms administered at about the same time). The combinations can also be administered separately, at different times, with each agent in a separate unit dosage form. Numerous approaches for administering the platinum-based anticancer agent and pentaaza macrocyclic ring complex can be readily adapted for use in the present disclosure. The pharmaceutical compositions may be delivered orally, e.g., in a tablet or capsule unit dosage form, or parenterally, e.g., in an injectable unit dosage form, or by some other route. For systemic administration, for example, the drugs can be administered by, for example, intravenous infusion (continuous or bolus). The compositions can be used for any therapeutic or prophylactic treatment where the patient benefits from treatment with the combination.

The specific therapeutically effective dose level for any particular patient will depend upon a variety of factors including the disorder being treated and the severity of the disorder; activity of the specific compound(s) employed; the age, body weight, general health, sex and diet of the patient; the time of administration; the route of administration; the rate of excretion of the specific compound(s) employed; the duration of the treatment; drugs used in combination or coincidental with the specific compound(s) employed and like factors well known in the medical and/or veterinary arts. For example, it is well within the skill of the art to start doses of the compound(s) at levels lower than those required to achieve the desired therapeutic effect and to gradually increase the dosage until the desired effect is achieved. If desired, the effective daily doses may be divided into multiple doses for purposes of administration. Consequently, single dose compositions may contain such amounts or submultiples to make up the daily dose.

In one embodiment, suitable or preferred doses for each of the components are employed in the methods or included in the compositions described herein. Preferred dosages for the pentaaza macrocyclic ring complex, for instance, may be within the range of 10 to 500 mg per patient per day. However, the dosage may vary depending on the dosing schedule, which can be adjusted as necessary to achieve the desired therapeutic effect. It should be noted that the ranges of effective doses provided herein are not intended to limit the disclosure and represent exemplary dose ranges. The most preferred dosage will be tailored to the individual subject, taking into account, among other things, the particular combinations employed, and the patient's age, sex, weight, physical condition, diet, etc., as is understood and determinable by one of ordinary skill in the art without undue experimentation.

Treatment of cancer, or cancer therapies, described herein includes achieving a therapeutic benefit, however the therapy may also be administered to achieve a prophylactic benefit. Therapeutic benefits generally refer to at least a partial eradication or amelioration of the underlying disorder being treated. For example, in a cancer patient, therapeutic benefit includes (partial or complete) eradication or amelioration of the underlying cancer. Also, a therapeutic benefit is achieved with at least partial, or complete, eradication or amelioration of one or more of the physiological symptoms associated with the underlying disorder such that an improvement is observed in the patient, notwithstanding the fact that the patient may still be afflicted with the underlying disorder. For prophylactic benefit, a method of the disclosure may be performed on, or a composition of the invention administered to, a patient at risk of developing cancer, or to a patient reporting one or more of the physiological symptoms of such conditions, even though a diagnosis of the condition may not have been made.

Furthermore, treatment of toxic effects associated with administration of a platinum-based anticancer agent, and/or treatment of a condition resulting from administration of a platinum-based anticancer agent, includes achieving a therapeutic benefit, however the therapy may also be administered to achieve a prophylactic benefit. Therapeutic benefits generally refer to at least a partial eradication or amelioration of the underlying disorder being treated. For example, in a patient at risk for or suffering from the toxic effects associated with administration of a platinum-based anticancer agent, therapeutic benefit includes (partial or complete) eradication or amelioration of the underlying condition and/or symptoms thereof. Also, a therapeutic benefit is achieved with at least partial, or complete, eradication or amelioration of one or more of the physiological symptoms associated with the underlying disorder such that an improvement is observed in the patient, notwithstanding the fact that the patient may still be afflicted with the underlying disorder. For prophylactic benefit, a method of the disclosure may be performed on, or a composition of the invention administered to, a patient at risk for toxicities associated with platinum-based anticancer agents (e.g., a person that is receiving or has received a platinum-based anticancer agent, or that is scheduled to receive a platinum-based anticancer agent), or to a patient reporting and/or suffering from one or more of the physiological symptoms of such conditions, even though a diagnosis of the condition may not have been made.

Cancer Treatment Methods

In general, any subject having, or suspected of having, a cancer or other proliferative disorder may be treated using the compositions and methods of the present disclosure. Subjects receiving treatment according to the methods described herein are mammalian subjects, and typically human patients. Other mammals that may be treated according to the present disclosure include companion animals such as dogs and cats, farm animals such as cows, horses, and swine, as well as birds and more exotic animals (e.g., those found in zoos or nature preserves). In one embodiment of the disclosure, a method is provided for the treatment of cancerous tumors, particularly solid tumors. Advantageously, the methods described herein may reduce the development of tumors, reduce tumor burden, or produce tumor regression in a mammalian host. Cancer patients and individuals desiring cancer prophylaxis can be treated with the combinations described herein.

Cancer and tumors generally refer to or describe the physiological condition in mammals that is typically characterized by unregulated cell growth. By means of the pharmaceutical combinations, co-formulations, and combination therapies of the present disclosure, various tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver.

In one embodiment, the tumor or cancer is chosen from adenoma, angio-sarcoma, astrocytoma, epithelial carcinoma, germinoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma, and teratoma. The tumor can be chosen from acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic, papillary serous adeno-carcinoma, pineal cell, pituitary tumors, plasmacytoma, pseudo-sarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Thus, for example, the present disclosure provides methods for the treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

For example, particular leukemias that can be treated with the combinations and methods described herein include, but are not limited to, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas can also be treated with the combinations and methods described herein. Lymphomas are generally neoplastic transformations of cells that reside primarily in lymphoid tissue. Lymphomas are tumors of the immune system and generally are present as both T cell- and as B cell-associated disease. Among lymphomas, there are two major distinct groups: non-Hodgkin's lymphoma (NHL) and Hodgkin's disease. Bone marrow, lymph nodes, spleen and circulating cells, among others, may be involved. Treatment protocols include removal of bone marrow from the patient and purging it of tumor cells, often using antibodies directed against antigens present on the tumor cell type, followed by storage. The patient is then given a toxic dose of radiation or chemotherapy and the purged bone marrow is then re-infused in order to repopulate the patient's hematopoietic system.

Other hematological malignancies that can be treated with the combinations and methods described herein include myelodysplastic syndromes (MDS), myeloproliferative syndromes (MPS) and myelomas, such as solitary myeloma and multiple myeloma. Multiple myeloma (also called plasma cell myeloma) involves the skeletal system and is characterized by multiple tumorous masses of neoplastic plasma cells scattered throughout that system. It may also spread to lymph nodes and other sites such as the skin. Solitary myeloma involves solitary lesions that tend to occur in the same locations as multiple myeloma.

In one embodiment, the methods and pharmaceutical compositions described herein are used to treat a cancer that is any of breast cancer, melanoma, oral squamous cell carcinoma, lung cancer including non-small cell lung cancer, renal cell carcinoma, colorectal cancer, prostate cancer, brain cancer, spindle cell carcinoma, urothelial cancer, bladder cancer, colorectal cancer, head and neck cancers such as squamous cell carcinoma, and pancreatic cancer. In yet another embodiment, the methods and pharmaceutical compositions described herein are used to treat a cancer that is any of head and neck cancer and lung cancer.

Methods for Treatment of Toxicities Associated with Platinum-Based Anticancer Agents In general, any subject having, or suspected of having, a condition resulting from the toxic effects of administration of a platinum-based anticancer agent (e.g., cisplatin) may be treated using the compositions and methods of the present disclosure. Subjects receiving treatment according to the methods described herein are mammalian subjects, and typically human patients. Other mammals that may be treated according to the present disclosure include companion animals such as dogs and cats, farm animals such as cows, horses, and swine, as well as birds and more exotic animals (e.g., those found in zoos or nature preserves). In one embodiment of the disclosure, a method is provided for the treatment of a condition associated with the toxicity of platinum-based anticancer agents, such as a condition from which a subject is suffering following administration to the subject of a platinum-based anticancer agent, for example as provided during cancer treatment, to alleviate the condition. In another embodiment, the treatment is provided to reduce and/or inhibit the toxicity of a platinum-based anticancer agent, for example when the platinum-based anticancer agent is provided during cancer treatment, to reduce the risk of developing a condition associated with the toxicity of the platinum-based anticancer agent. Advantageously, the methods described herein may reduce the toxic effects and/or alleviate toxic condition while simultaneously allowing for cancer treatment with the platinum-based anti-cancer agent, so example to reduce the development of tumors, reduce tumor burden, or produce tumor regression in a mammalian host. Cancer patients and individuals desiring cancer prophylaxis can be treated with the combinations described herein.

In one embodiment, the toxicity and/or toxic condition associated with administration of the platinum-based anticancer agent, and which may be treated with the method(s) described herein (and/or the risk of developing such a condition can be reduced), includes at least one of nephrotoxicity, myelotoxicity, ototoxicity and neurotoxicity, and conditions associated therewith. For example, in one embodiment the administration of the pentaaza macrocyclic ring complex may be capable of reducing nephrotoxic effects associated with the administration of a platinum-based anticancer agent. Nephrotoxicity refers to toxicity to the kidneys, and can result in reduced renal function, and acute kidney injury, and even renal failure, among other conditions and is commonly associated with the administration of anti-cancer drugs (see, e.g., Lameire N., *Clin Kidney J,* 7(1): 11-22 (2014); Zhu et al, *Arch Toxicol,* 89(12): 2197-2205 (2015)). Whole blood urea nitrogen (BUN) levels and creatinine levels may be measured to provide an indication of an extent of kidney injury, with increased levels indicating reduced kidney function. Other markers of kidney injury include kidney injury molecule 1 (KIM1) and neutrophil gelatinase-associated lipocalin (NGAL). As another example, in one embodiment the administration of the pentaaza macrocyclic ring complex may be capable of reducing myelotoxic effects associated with the administration of a platinum-based anticancer agent. Myelotoxicity, also referred to as myelosuppression and/or bone marrow suppression, refers to the decrease in the production of cells such as leukocytes, erythrocytes and thrombocytes, and can result in conditions such as neutropenia, thrombocytopenia, and anemia, among other conditions, and is commonly associated with the administration of anti-cancer drugs (see, e.g., Kurtin S., *J Adv Pract Oncol,* 3(4): July-August (2012); Son et al., *Hum Exp Toxicol,* 30(7): 649-655 (2011)). Neutrophils and white blood cell counts may also be decreased. In yet another embodiment, the administration of the pentaaza macrocyclic ring complex may be capable of reducing ototoxic effects associated with the administration of a platinum-based anticancer agent, which are toxicities to the each such as the cochlea, auditory nerve and/or vestibular system. Accordingly, in one embodiment, the treatment methods herein can comprise treating a subject who is afflicted with and/or at risk for a toxicity resulting from platinum-based anticancer treatment, such as a subject afflicted with and/or at risk for one or more of nephrotoxicity and myelotoxicity, due to administration of a platinum-based anticancer agent.

Pharmaceutical Formulations

Another aspect of the present disclosure relates to the pharmaceutical compositions comprising the combinations described herein, together with a pharmaceutically acceptable excipient. The pharmaceutical compositions include the pentaaza macrocyclic ring complex (e.g., those corresponding to Formula (I)), and at least one platinum-based anticancer agent, and combinations thereof, as discussed above, typically formulated as a pharmaceutical dosage form, optionally in combination with a pharmaceutically acceptable carrier, additive or excipient. In one embodiment, for example, the pharmaceutical composition comprises a pentaaza macrocyclic ring complex, a platinum-based anticancer agent and a pharmaceutically acceptable excipient. Pharmaceutical compositions according to the present disclosure may be used in the treatment of cancer.

The pharmaceutical compositions described herein are products that result from the mixing or combining of more than one active ingredient and include both fixed and non-fixed combinations of the active ingredients. Fixed combinations are those in which the active ingredients, e.g., a pentaaza macrocyclic ring complex and a platinum-based anticancer agent, are administered to a patient simultaneously in the form of a single entity or dosage. Other active agents may also be administered as a part of the single entity or dosage, or may be separately administered Non-fixed combinations are those in which the active ingredients, e.g., a pentaaza macrocyclic ring complex and a platinum-based anticancer agent, are administered to a patient as separate entities either simultaneously, concurrently or sequentially with no specific intervening time limits, wherein such administration provides effective levels of the compounds in the body of the patient. The latter also applies to cocktail therapy, e.g., the administration of three or more active ingredients.

The above-described pentaaza macrocyclic ring complex and the platinum-based anticancer agent may be dispersed in a pharmaceutically acceptable carrier prior to administration to the mammal; i.e., the components described herein are preferably co-formulated. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the compositions of the described herein can be formulated for any route of administration so long as the blood circulation system is available via that route, and in accordance with the conventional route of administration. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in combination with the compositions of the present disclosure are well known to those of ordinary skill in the art and are selected based upon a number of factors: the particular compound(s) and agent(s) used, and its/their concentration, stability and intended bioavailability; the subject, its age, size and general condition; and the route of administration. Suitable non-aqueous, pharmaceutically-acceptable polar solvents include, but are not limited to, alcohols (e.g., a-glycerol formal, 6-glycerol formal, 1,3-butyleneglycol, aliphatic or aromatic alcohols having 2 to 30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(6-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di-, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di-, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyester, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, DE, polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$ to $C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2 to 30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3 to 30 carbon atoms (e.g., acetone, methyl ethyl ketone, methyl isobutyl ketone); aliphatic, cycloaliphatic or aromatic hydrocarbons having 4 to 30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, di methylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1 to 30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

In some embodiments, oils or non-aqueous solvents may be employed in the formulations, e.g., to bring one or more of the compounds into solution, due to, for example, the presence of large lipophilic moieties. Alternatively, emulsions, suspensions, or other preparations, for example, liposomal preparations, may be used. With respect to liposomal preparations, for example, any known methods for preparing liposomes may be used. See, for example, Bangham et al., J. Mol. Biol, 23: 238-252 (1965) and Szoka et al., Proc. Natl Acad. Sci 75: 4194-4198 (1978), incorporated herein by reference. Thus, in one embodiment, one or more of the compounds are administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines. Ligands may also be attached to the liposomes, for instance, to direct these compositions to particular sites of action.

Other pharmaceutically acceptable solvents for use in the pharmaceutical compositions described herein are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, New York, 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, New York, 1980), Remington's Pharmaceutical Sciences (A. Gennaro, ed., 19th ed.) (Mack Publishing, Easton, PA, 1995), The United States Pharmacopeia 24, The National Formulary 19, (National Publishing, Philadelphia, PA, 2000), and A. J. Spiegel et al., Use of Non-aqueous Solvents in Parenteral Products, Journal of Pharmaceutical Sciences, Vol. 52, No. 10, pp. 917-927 (1963).

Formulations containing the pentaaza macrocyclic ring complex and the platinum-based anticancer agent may take the form of solid, semi-solid, lyophilized powder, or liquid dosage forms such as, for instance, aerosols, capsules, creams, emulsions, foams, gels/jellies, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages. If formulated as a fixed dose, such pharmaceutical compositions or formulation products employ the pentaaza macrocyclic ring complex and the platinum-based anticancer agent within accepted dosage ranges.

In one embodiment, a formulation is provided that contains the platinum-based anticancer agent as a part of liquid dosage form, such as a sterile liquid dosage form suitable for injection. For example, the liquid form containing the platinum-based anticancer agent in combination with one or more further ingredients, such as edetate disodium (EDTA). In one embodiment, the liquid form can comprise EDTA in an amount suitable to act as a preservative and/or metalchelating agent, such as an amount of about 0.025%. The liquid form can further comprise water, and may also comprise a pH adjuster, such as sodium bicarbonate, for pH adjustment in the range of pH 5.5 to 7.0. In one embodiment, the pentaaza macrocyclic ring complex can also be provided as a part of a sterile liquid dosage form suitable for injection, either in the same liquid dosage form with the platinum-based anticancer agent or as a separate dosage form.

Formulations for certain pentaaza macrocyclic ring complexes are also described in, for example, in U.S. Pat. Nos. 5,610,293, 5,637,578, 5,874,421, 5,976,498, 6,084,093, 6,180,620, 6,204,259, 6,214,817, 6,245,758, 6,395,725, and 6,525,041 (each of which is hereby incorporated herein by reference in its entirety).

It is contemplated that co-formulations of the pentaaza macrocyclic ring complex and the platinum-based anticancer agent may employ conventional formulation techniques for these components individually, or alternative formulation routes, subject to compatibility and efficacy of the various components, in combination.

The above-described pharmaceutical compositions including the pentaaza macrocyclic compound and the platinum-based anticancer agent may additionally include one or more additional pharmaceutically active components. Suitable pharmaceutically active agents that may be included in the compositions according to aspects of the present invention include, for instance, antiemetics, anesthetics, antihypertensives, antianxiety agents, anticlotting agents, anticonvulsants, blood glucose-lowering agents, decongestants, antihistamines, antitussives, antineoplastics, beta blockers, anti-inflammatory agents, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's Disease agents, antibiotics, anti-depressants, and antiviral agents. The individual components of such combinations may be administered either sequentially or simultaneously in separate or combined pharmaceutical formulations.

In yet another embodiment, a kit may be provided that includes both a pentaaza macrocyclic ring complex and a platinum-based anticancer agent, for treatment of a condition such as cancer, and/or to treat and/or reduce the risk of toxicities associated with administration of a platinum-based anticancer agent. For example, the kit may comprise a first vessel or container having therein a formulation comprising the pentaaza macrocyclic ring complex, such as an oral or injectable formulation of the pentaaza macrocyclic ring complex, and a second vessel or container having therein a formulation comprising the platinum-based anticancer agent, such as an injectable formulation of platinum-based anticancer agent. The kit may further comprise a label or other instructions for administration of the active agents, recommended dosage amounts, durations and administration regimens, warnings, listing of possible drug-drug interactions, and other relevant instructions, such as a label instructing therapeutic regimens (e.g., dosing, frequency of dosing, etc.) corresponding to any of those described herein.

Combination Treatment with Cancer Therapy

In one embodiment, the pentaaza macrocyclic ring complex and the platinum-based anticancer agent can be administered in combination with another cancer therapy, to provide therapeutic treatment. For example, the pentaaza macrocyclic ring complex and the platinum-based anticancer agent may be administered as a part of a radiation therapy.

In general, the temporal aspects of the administration of the pentaaza macrocyclic ring complex and the platinum-based anticancer agent may depend for example, on the particular radiation therapy that is selected, or the type, nature, and/or duration of the radiation exposure. Other considerations may include the disease or disorder being treated and the severity of the disease or disorder; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors. For example, the compounds may be administered in various embodiments before, during, and/or after the administration of the radiation therapy (e.g., before, during or after exposure to and/or before, during or after a course of radiation therapy comprising multiple exposures and/or doses). By way of another example, the compounds may be administered in various embodiments before, during, and/or after an exposure to radiation.

If desired, the effective dose can be divided into multiple doses for purposes of administration; consequently, single dose compositions may contain such amounts or submultiples thereof to make up the dose.

In one embodiment, for example, the pentaaza macrocyclic ring complex and the platinum-based anticancer agent are administered to the patient prior to or simultaneous with the radiation exposure. In another embodiment, for example, the components are administered to the patient prior to, but not after, the radiation exposure. In yet another embodiment, one or more of the pentaaza macrocyclic ring complex and the platinum-based anticancer agent are administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the radiation exposure, such as an initial radiation exposure in a course of radiation treatment, or prior to another dose or dose fraction of radiation that is one of the doses or dose fractions of radiation in the course of treatment. In still other embodiments, for example, the pentaaza macrocyclic ring complex and the platinum-based anticancer agent are administered to the patient after the radiation exposure; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the radiation exposure, which may be a dose or dose fraction of radiation in a multi-dose course of radiation therapy, or may be the single or final dose or dose fraction of radiation in the radiation therapy.

In one embodiment, the pentaaza macrocyclic ring complex and the platinum-based anticancer agent are administered as a part of a course of therapy that includes the radiation therapy. In radiation therapy, a patient receives a dose or dose fraction of ionizing radiation to kill or control the growth of cancerous cells. The dose or dose fraction of radiation may be directed at a specific part of the body, and the beam of radiation may also be shaped according to a predetermined treatment regimen, to reduce deleterious effects on parts of the body not afflicted with cancer. A typical course of radiation therapy may include one or a plurality of doses or dose fractions of radiation, which can be administered over the course of days, weeks and even months. A total "dose" of radiation given during a course of radiation therapy typically refers to the amount of radiation a patient receives during the entire course of radiation therapy, which doses may be administered as dose "fractions" corresponding to multiple radiation exposures in the case where the total dose is administered over several sessions, with the sum of the fractions administered corresponding to the overall dose.

In one embodiment, at least one of the pentaaza macrocyclic ring complex and the platinum-based anticancer agent are administered within a predetermined time period before or after a radiation exposure, such as a before or after a radiation dose or dose fraction. For example, the pentaaza macrocyclic ring complex and the platinum-based anticancer agent may be administered within 1 week, 48 hours, 24 hours, 12 hours, 6, hours, 2 hours, 1 hour or even within 30 minutes of the patient receiving the radiation exposure, such as the dose or dose fraction (either before or after the radiation exposure corresponding to the radiation dose or dose fraction). Other durations between the radiation exposure and administration of the compound that result in the enhanced the killing of cancer cells may also be suitable. In one embodiment, one or more of the pentaaza macrocyclic ring complex and the platinum-based anticancer agent may be administered before the radiation exposure, and the remaining one or more of the pentaaza macrocyclic ring complex and the platinum-based anticancer agent can be administered after the radiation exposure. One or more of the pentaaza macrocyclic ring complex and the platinum-based anticancer agent may also be administered both before and after administration of a radiation exposure.

In one embodiment, a course of radiation therapy includes a plurality of radiation doses or dose fractions given over a predetermined period of time, such as over the course of hours, weeks, days and even months, with the plural doses or dose fractions being either of the same magnitude or varying. That is, a course of radiation therapy can comprise the administration of a series of multiple doses or dose fractions of radiation. In one embodiment, the pentaaza macrocyclic ring complex and the platinum-based anticancer agent can be administered before one or more radiation doses or dose fractions in the series, such as before each radiation dose or dose fraction, or before some number of the radiation doses or dose fractions. Furthermore, the administration of the pentaaza macrocyclic ring complex and the platinum-based anticancer agent during the course of radiation therapy can be selected to enhance the cancer treating effects of the radiation therapy, such as by sensitizing cancer cells to the radiation therapy. In one embodiment, the pentaaza macrocyclic ring complex and the platinum-based anticancer agent are administered within a predetermined duration before or after of each dose or dose fraction, such as the predetermined duration discussed above. In another embodiment, the pentaaza macrocyclic ring complex and the platinum-based anticancer agent are administered within a predetermined duration of time before or after only select doses or dose fractions. In yet another embodiment, at least one of the pentaaza macrocyclic ring complex and the platinum-based anticancer agent is administered within a predetermined duration of time before the doses, while another of the pentaaza macrocyclic ring complex and the platinum-based anticancer agent is administered within a predetermined duration of time after the doses or dose fraction. In a further embodiment, at least one of the pentaaza macrocyclic ring complex and the platinum-based anticancer agent is administered only within the predetermined duration before or after select doses or dose fractions, while another of the pentaaza macrocyclic ring complex and the platinum-based anticancer agent is administered only within the predetermined duration before or after doses or dose fractions other than the select doses or dose fractions.

A suitable overall dose to provide during a course of therapy can be determined according to the type of treatment to be provided, the physical characteristics of the patient and other factors, and the dose fractions that are to be provided can be similarly determined. In one embodiment, a dose fraction of radiation that is administered to a patient may be at least 1.8 Gy, such as at least 2 Gy, and even at least 3 Gy, such as at least 5 Gy, and even at least 6 Gy. In yet another embodiment, a dose fraction of radiation that is administered to a patient may be at least 10 Gy, such as at least 12 Gy, and even at least 15 Gy, such as at least 18 Gy, and even at least 20 Gy, such as at least 24 Gy. In general, a dose fraction of radiation administered to a patient will not exceed 54 Gy. Furthermore, it should be noted that, in one embodiment, a dose fraction delivered to a subject may refer to an amount delivered to a specific target region of a subject, such as a target region of a tumor, whereas other regions of the tumor or surrounding tissue may be exposed to more or less radiation than that specified by the nominal dose fraction amount.

In yet another embodiment, the pentaaza macrocyclic ring complex and the platinum-based anticancer agent are administered as a part of a course of therapy that includes administration of an additional chemotherapeutic agent. In chemotherapy, chemotherapeutic agents are administered to a patient to kill or control the growth of cancerous cells. A typical course of chemotherapy may include one or a plurality of doses of one or more chemotherapeutic agents, which can be administered over the course of days, weeks and even months. Chemotherapeutic agents can include at least one of: alkylating antineoplastic agents such as nitrogen mustards (e.g. cyclophosphamide, chlorambucil), nitrosoureas (e.g. n-nitroso-n-methylurea, carmustine, semustine), tetrazines (e.g. dacarbazine, mitozolimide), aziridines (e.g. thiotepa, mytomycin); anti-metabolites such as anti-folates (e.g. methotrexate and pemetrexed), fluoropyrimidines (e.g., fluorouracil, capecitabine), anthracyclines (e.g. doxorubicin, daunorubicin, epirubicin), deoxynucleoside analogs (e.g. cytarabine, gemcitabine, decitabine) and thiopurines (e.g., thioguanine, mercaptopurine); anti microtubule agents such as taxanes (e.g. paclitaxel, docetaxel); topoisomerase inhibitors (e.g. etoposide, doxorubicin, mitoxantrone, teniposide); and antitumor antibiotics (e.g. bleomycin, mitomycin). For example, the chemotherapeutic agent may be selected from the group consisting of all-trans retinoic acid, arsenic trioxide, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tiguanine, valrubicin, vinblastine, vincristine, vindesine, and vinorelbine. The administration of many of the chemotherapeutic agents is described in the "Physicians' Desk Reference" (PDR), e.g., 1996 edition (Medical Economics Company, Montvale, N.J. 07645-1742, USA).

In one embodiment, the pentaaza macrocyclic ring complex and the platinum-based anticancer agent are administered as a part of a course of therapy that includes an additional chemotherapeutic agent selected from the group consisting of doxorubicin, bleomycin, and paclitaxel. Furthermore, in one embodiment, the additional chemotherapeutic agent may be selected from the group consisting of a taxane, an anticancer antibiotic, and an anthracycline. Other chemotherapeutic agents can include arsenic trioxide and 5-FU, which agents can also be used in the methods and compositions described herein. (Alexandre et al., Cancer Res. 67: (8), 3512-3517 (2007); Yen et al., J. Clin. Invest. 98 (5), 1253-1260 (1996); Masuda et al., Cancer Chemother. Pharmacol. 47(2), 155-160 (2001)).

According to yet another embodiment, the additional chemotherapeutic agent can include at least one of an antimetabolite anti-cancer agents and antimitotic anti-cancer agents, and combinations thereof, which may include some of the agents described above and well as other agents described further herein. Various antimetabolite and antimitotic agents may be employed in the methods and compositions described herein.

Antimetabolic agents typically structurally resemble natural metabolites, which are involved in normal metabolic processes of cancer cells such as the synthesis of nucleic acids and proteins. The antimetabolites, however, differ enough from the natural metabolites such that they interfere with the metabolic processes of cancer cells. In the cell, antimetabolites are mistaken for the metabolites they resemble, and are processed by the cell in a manner analogous to the normal compounds. The presence of the "decoy" metabolites prevents the cells from carrying out vital functions and the cells are unable to grow and survive. For example, antimetabolites may exert cytotoxic activity by substituting these fraudulent nucleotides into cellular DNA, thereby disrupting cellular division, or by inhibition of critical cellular enzymes, which prevents replication of DNA.

In one embodiment, therefore, the antimetabolite agent is a nucleotide or a nucleotide analog. In certain embodiments, for example, the antimetabolite agent may comprise purine (e.g., guanine or adenosine) or analogs thereof, or pyrimidine (cytidine or thymidine) or analogs thereof, with or without an attached sugar moiety.

Suitable antimetabolite agents for use in the present disclosure may be generally classified according to the metabolic process they affect, and can include, but are not limited to, analogues and derivatives of folic acid, pyrimidines, purines, and cytidine. Thus, in one embodiment, the antimetabolite agent(s) is selected from the group consisting of cytidine analogs, folic acid analogs, purine analogs, pyrimidine analogs, and combinations thereof.

In one particular embodiment, for example, the antimetabolite agent is a cytidine analog. According to this embodiment, for example, the cytidine analog may be selected from the group consisting of cytarabine (cytosine arabinodside), azacitidine (5-azacytidine), and salts, analogs, and derivatives thereof.

In another particular embodiment, for example, the antimetabolite agent is a folic acid analog. Folic acid analogs or antifolates generally function by inhibiting dihydrofolate reductase (DHFR), an enzyme involved in the formation of nucleotides; when this enzyme is blocked, nucleotides are not formed, disrupting DNA replication and cell division. According to certain embodiments, for example, the folic acid analog may be selected from the group consisting of denopterin, methotrexate (amethopterin), pemetrexed, pteropterin, raltitrexed, trimetrexate, and salts, analogs, and derivatives thereof.

In another particular embodiment, for example, the antimetabolite agent is a purine analog. Purine-based antimetabolite agents function by inhibiting DNA synthesis, for example, by interfering with the production of purine containing nucleotides, adenine and guanine which halts DNA synthesis and thereby cell division. Purine analogs can also be incorporated into the DNA molecule itself during DNA synthesis, which can interfere with cell division. According to certain embodiments, for example, the purine analog may be selected from the group consisting of acyclovir, allopurinol, 2-aminoadenosine, arabinosyl adenine (ara-A), azacitidine, azathiprine, 8-aza-adenosine, 8-fluoro-adenosine, 8-methoxy-adenosine, 8-oxo-adenosine, cladribine, deoxycoformycin, fludarabine, gancylovir, 8-aza-guanosine, 8-fluoro-guanosine, 8-methoxy-guanosine, 8-oxo-guanosine, guanosine diphosphate, guanosine diphosphate-beta-L-2-aminofucose, guanosine diphosphate-D-arabinose, guanosine diphosphate-2-fluorofucose, guanosine diphosphate fucose, mercaptopurine (6-MP), pentostatin, thiamiprine, thioguanine (6-TG), and salts, analogs, and derivatives thereof.

In yet another particular embodiment, for example, the antimetabolite agent is a pyrimidine analog. Similar to the purine analogs discussed above, pyrimidine-based antimetabolite agents block the synthesis of pyrimidine-containing nucleotides (cytosine and thymine in DNA; cytosine and uracil in RNA). By acting as "decoys," the pyrimidine-based compounds can prevent the production of nucleotides, and/or can be incorporated into a growing DNA chain and lead to its termination. According to certain embodiments, for example, the pyrimidine analog may be selected from the group consisting of ancitabine, azacitidine, 6-azauridine, bromouracil (e.g., 5-bromouracil), capecitabine, carmofur, chlorouracil (e.g. 5-chlorouracil), cytarabine (cytosine arabinoside), cytosine, dideoxyuridine, 3'-azido-3'-deoxythymidine, 3'-dideoxycytidin-2'-ene, 3'-deoxy-3'-deoxythymidin-2'-ene, dihydrouracil, doxifluridine, enocitabine, floxuridine, 5-fluorocytosine, 2-fluorodeoxycytidine, 3-fluoro-3'-deoxythymidine, fluorouracil (e.g., 5-fluorouracil (also known as 5-FU), gemcitabine, 5-methylcytosine, 5-propynylcytosine, 5-propynylthymine, 5-propynyluracil, thymine, uracil, uridine, and salts, analogs, and derivatives thereof. In one embodiment, the pyrimidine analog is other than 5-fluorouracil. In another embodiment, the pyrimidine analog is gemcitabine or a salt thereof.

In certain embodiments, the antimetabolite agent is selected from the group consisting of 5-fluorouracil, capecitabine, 6-mercaptopurine, methotrexate, gemcitabine, cytarabine, fludarabine, pemetrexed, and salts, analogs, derivatives, and combinations thereof. In other embodiments, the antimetabolite agent is selected from the group consisting of capecitabine, 6-mercaptopurine, methotrexate, gemcitabine, cytarabine, fludarabine, pemetrexed, and salts, analogs, derivatives, and combinations thereof. In one particular embodiment, the antimetabolite agent is other than 5-fluorouracil. In a particularly preferred embodiment, the antimetabolite agent is gemcitabine or a salt or thereof (e.g., gemcitabine HCl (Gemzar®)).

Other antimetabolite agents may be selected from, but are not limited to, the group consisting of acanthifolic acid, aminothiadiazole, brequinar sodium, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, Wellcome EHNA, Merck & Co. EX-015, fazarabine, fludarabine phosphate, N-(2'-furanidyl)-5-fluorouracil, Daiichi Seiyaku FO-152, 5-FU-fibrinogen, isopropyl pyrrolizine, Lilly LY-188011; Lilly LY-264618, methobenzaprim, Wellcome MZPES, norspermidine, NCI NSC-127716, NCI NSC-264880, NCI NSC- 39661, NCI NSC-612567, Warner-Lambert PALA, pentostatin, piritrexim, plicamycin, Asahi Chemical PL-AC, Takeda TAC-788, tiazofurin, Erbamont TIF, tyrosine kinase inhibitors, Taiho UFT and uricytin, among others.

In one embodiment, the chemotherapeutic agent comprises an antimitotic agent that is a microtubule inhibitor or a mictrotubule stabilizer. In general, microtubule stabilizers, such as taxanes (some of which are also described above) and epothilones, bind to the interior surface of the beta-microtubule chain and enhance microtubule assembly by promoting the nucleation and elongation phases of the polymerization reaction and by reducing the critical tubulin subunit concentration required for microtubules to assemble. Unlike mictrotubule inhibitors, such as the vinca alkaloids, which prevent microtubule assembly, the microtubule stabilizers, such as taxanes, decrease the lag time and dramatically shift the dynamic equilibrium between tubulin dimers and microtubule polymers towards polymerization. In one embodiment, therefore, the microtubule stabilizer is a taxane or an epothilone. In another embodiment, the microtubule inhibitor is a vinca alkaloid.

One element of the therapy described herein may include the use of a taxane or derivative or analog thereof, some of which have also been discussed above. In one embodiment, the taxane may be a naturally derived compound or a related form, or may be a chemically synthesized compound or a derivative thereof, with antineoplastic properties. The taxanes are a family of terpenes, including, but not limited to paclitaxel (Taxol®) and docetaxel (Taxotere®), which are derived primarily from the Pacific yew tree, *Taxus brevifolia*, and which have activity against certain tumors, particularly breast and ovarian tumors. In one embodiment, the taxane is docetaxel or paclitaxel. Paclitaxel is a preferred taxane and is considered an antimitotic agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions.

Also included are a variety of known taxane derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; deoxygenated paclitaxel compounds such as those described in U.S. Pat. No. 5,440,056; and taxol derivatives described in U.S. Pat. No. 5,415,869. As noted above, it further includes prodrugs of paclitaxel including, but not limited to, those described in WO 98/58927; WO 98/13059; and U.S. Pat. No. 5,824,701. The taxane may also be a taxane conjugate such as, for example, paclitaxel-PEG, paclitaxel-dextran, paclitaxel-xylose, docetaxel-PEG, docetaxel-dextran, docetaxel-xylose, and the like. Other derivatives are mentioned in "Synthesis and Anticancer Activity of Taxol Derivatives," D. G. I. Kingston et al., Studies in Organic Chemistry, vol. 26, entitled "New Trends in Natural Products Chemistry" (1986), Atta-ur-Rabman, P. W. le Quesne, Eds. (Elsevier, Amsterdam 1986), among other references. Each of these references is hereby incorporated by reference herein in its entirety.

Various taxanes may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267) (each of which is hereby incorporated by reference herein in its entirety), or obtained from a variety of commercial sources, including for example, Sigma-Aldrich Co., St. Louis, MO.

Alternatively, the antimitotic agent can be a microtubule inhibitor; in one preferred embodiment, the microtubule inhibitor is a vinca alkaloid. In general, the vinca alkaloids are mitotic spindle poisons. The vinca alkaloid agents act during mitosis when chromosomes are split and begin to migrate along the tubules of the mitosis spindle towards one of its poles, prior to cell separation. Under the action of these spindle poisons, the spindle becomes disorganized by the dispersion of chromosomes during mitosis, affecting cellular reproduction. According to certain embodiments, for example, the vinca alkaloid is selected from the group consisting of vinblastine, vincristine, vindesine, vinorelbine, and salts, analogs, and derivatives thereof.

The antimitotic agent can also be an epothilone. In general, members of the epothilone class of compounds stabilize microtubule function according to mechanisms similar to those of the taxanes. Epothilones can also cause cell cycle arrest at the G2-M transition phase, leading to cytotoxicity and eventually apoptosis. Suitable epithiolones include epothilone A, epothilone B, epothilone C, epothilone D, epothilone E, and epothilone F, and salts, analogs, and derivatives thereof. One particular epothilone analog is an epothilone B analog, ixabepilone (Ixempra™).

In certain embodiments, the antimitotic anti-cancer agent is selected from the group consisting of taxanes, epothilones, vinca alkaloids, and salts and combinations thereof. Thus, for example, in one embodiment the antimitotic agent is a taxane. More preferably in this embodiment the antimitotic agent is paclitaxel or docetaxel, still more preferably paclitaxel. In another embodiment, the antimitotic agent is an epothilone (e.g., an epothilone B analog). In another embodiment, the antimitotic agent is a vinca alkaloid.

In one embodiment, at least one of the pentaaza macrocyclic ring complex and the platinum-based anticancer agent are administered within a predetermined time period before or after a dose of an additional chemotherapeutic agent is administered. For example, the pentaaza macrocyclic ring complex and the platinum-based anticancer agent may be administered within 1 week, 48 hours, 24 hours, 12 hours, 6, hours, 2 hours, 1 hour or even within 30 minutes of the patient receiving the dose of the additional chemotherapeutic agent (either before or after the dose of chemotherapeutic agent). Other durations between the additional chemotherapeutic agent dose and administration of the components that result in the enhanced the killing of cancer cells may also be suitable. In one embodiment, one or more of the pentaaza macrocyclic ring complex and the platinum-based anticancer agent may be administered before the dose of the additional chemotherapeutic agent, and the remaining one or more of the pentaaza macrocyclic ring complex and the platinum-based anticancer agent can be administered after the dose of the additional chemotherapeutic agent. One or more of the pentaaza macrocyclic ring complex and the platinum-based anticancer agent may also be administered both before and after administration of the dose of additional chemotherapeutic agent.

In one embodiment, a course of chemotherapy includes a singular dose of the additional chemotherapeutic agent. In another embodiment, a course of chemotherapy includes a plurality of doses of the additional chemotherapeutic agent given over a predetermined period of time, such as over the course of hours, weeks, days and even months. The plural doses may be either of the same magnitude or varying, and can include doses of the same or different chemotherapeutic agents and/or a combination of chemotherapeutic agents. The administration of the pentaaza macrocyclic ring complex and the platinum-based anticancer agent during the course of chemotherapy can be selected to enhance the cancer treating effects of the chemotherapy, such as by increasing intracellular levels of hydrogen peroxide to promote oxidative stress in the cancer cells. In one embodiment, the pentaaza macrocyclic ring complex and the platinum-based anticancer agent are administered within a predetermined duration before or after each dose, such as the predetermined duration discussed above. In another embodiment, the pentaaza macrocyclic ring complex and platinum-based anticancer agent are administered within a predetermined duration of time before or after only select doses. In yet another embodiment, at least one of the pentaaza macrocyclic ring complex and the platinum-based anticancer agent are administered within a predetermined duration of time before the doses, while another of the pentaaza macrocyclic ring complex and the platinum-based anticancer agent are administered within a predetermined duration of time after the doses. In a further embodiment, at least one of the pentaaza macrocyclic ring complex and the platinum-based anticancer agent is administered only within the predetermined duration before or after select doses, while another of the pentaaza macrocyclic ring complex and the platinum-based anticancer agent is administered only within the predetermined duration before or after doses other than the select doses.

In yet another embodiment, at least one of the pentaaza macrocyclic ring complex and the platinum-based anticancer agent is administered in combination with both a radiation therapy and a chemotherapy involving administration of an additional chemotherapeutic agent.

EXAMPLES

The following non-limiting examples are provided to further illustrate aspects of the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Synergistic Effects of Anticancer Treatment

Example 1

Effect of GC4419 and Cisplatin on Survival of Cancer Cells in Culture. H460 human non-small cell lung carcinoma (NSCLC) cells in culture were treated with 24 μM GC4419 (+GC) or Media (−GC) and the indicated concentrations of cisplatin. After 120 hrs the surviving fraction of cells was determined. The addition of GC4419 to cisplatin treatment decreased the surviving fraction of H460 cells compared to cells treated with cisplatin alone. GC4419 significantly sensitized H460 lung carcinoma cells to the cisplatin (see FIG. 1: Effect of GC4419 and Cisplatin on Survival of H460 Cells in Culture).

Example 2

Figure 2:
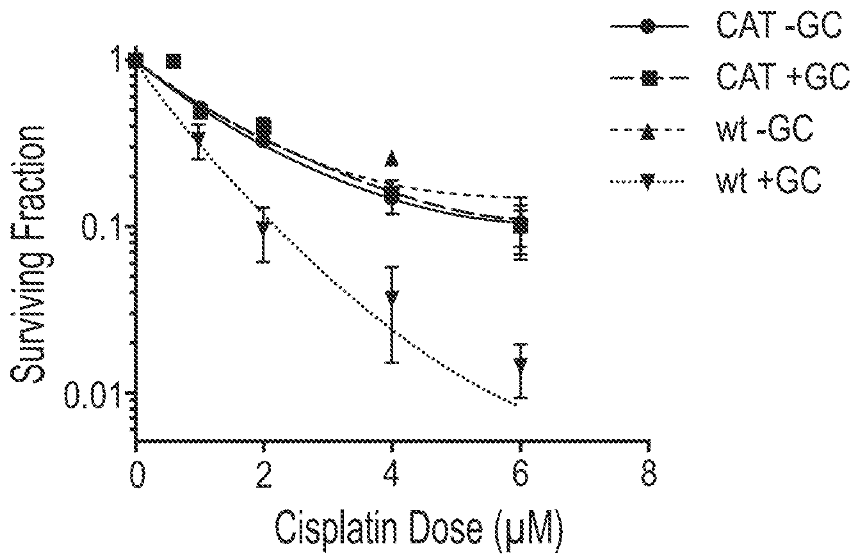
FIG. 2 shows an effect of GC4419, cisplatin and overexpressoinof catalase on survival of H1299CAT cells in culture.

Effect of GC4419, Cisplatin and Overexpression of Catalase on Survival of Cancer Cells in Culture. H1299 human NSCLC cells, modified to inducibly overexpress catalase (CAT), an enzyme that removes hydrogen peroxide ($H_2O_2$) were treated in cell culture with 24 μM GC4419 (+GC) or Media (−GC) and the indicated concentrations of cisplatin. CAT overexpression in this line (H1299CAT) was induced by administration of doxycycline, which turned on transcription of the inserted catalase genes. 120 hrs after treatment with cisplatin with or without GC4419. the surviving fraction of H1299CAT cells was determined, both with and without CAT overexpression. Without CAT overexpression ("wt"), the addition of GC4419 to cisplatin treatment decreased the surviving fraction of H460 cells compared to cells treated with cisplatin alone. similarly to H460 cells when treated with both GC4419 and cisplatin. In contrast, the overexpression of CAT ("CAT", removing $H_2O_2$ generated from superoxide by GC4419) abrogated the GC4419 contribution to cisplatin response, demonstrating that GC4419 significantly sensitized H460 lung carcinoma cells to the cisplatin and that the enhanced response was $H_2O_2$ dependent (see, FIG. 2: Effect of GC4419, Cisplatin and Overexpression of Catalase on Survival of H1299CAT Cells in Culture).

Example 3

Figure 3:
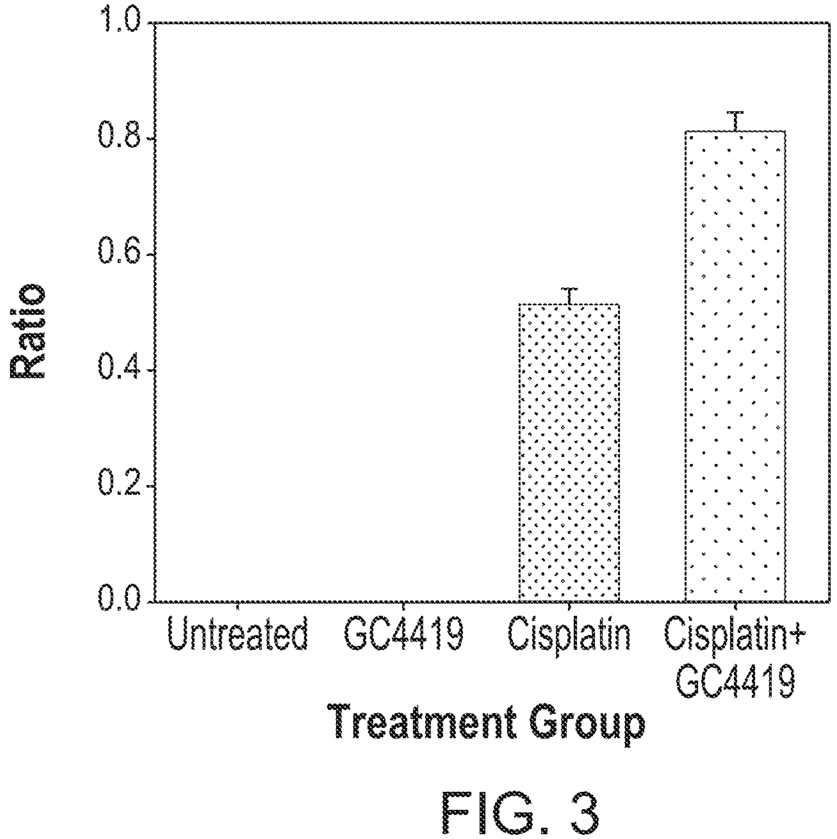
FIG. 3 shows an effect of GC4419 and cisplatin on PARP activation in H460 cells.

Effect of GC4419 and Cisplatin on PARP Activation in Cancer Cells. H460 NSCLC cells in culture were treated with 24 μM GC4419 and 1 μM cisplatin for 24 hr. At this time cells were solubilized and PARP (poly (ADP ribosyl) polymerase) activity was measured by Western blot as the ratio of the 89 kd active form to the 116 kd inactive form. PARP is a nuclear enzyme involved in DNA repair of single strand breaks and is activated following cell stress including chemotherapy and irradiation. As shown in FIG. 3, cisplatin increased PARP activity compared to untreated cells or GC4419 treatment alone. The addition of GC4419 to cisplatin further and significantly ($p<0.01$) increased PARP activity, suggesting that GC4419 increased the cancer cell damage caused by cisplatin (see, FIG. 3: Effect of GC4419 and Cisplatin on PARP Activation in H460 Cells).

Figure 4:
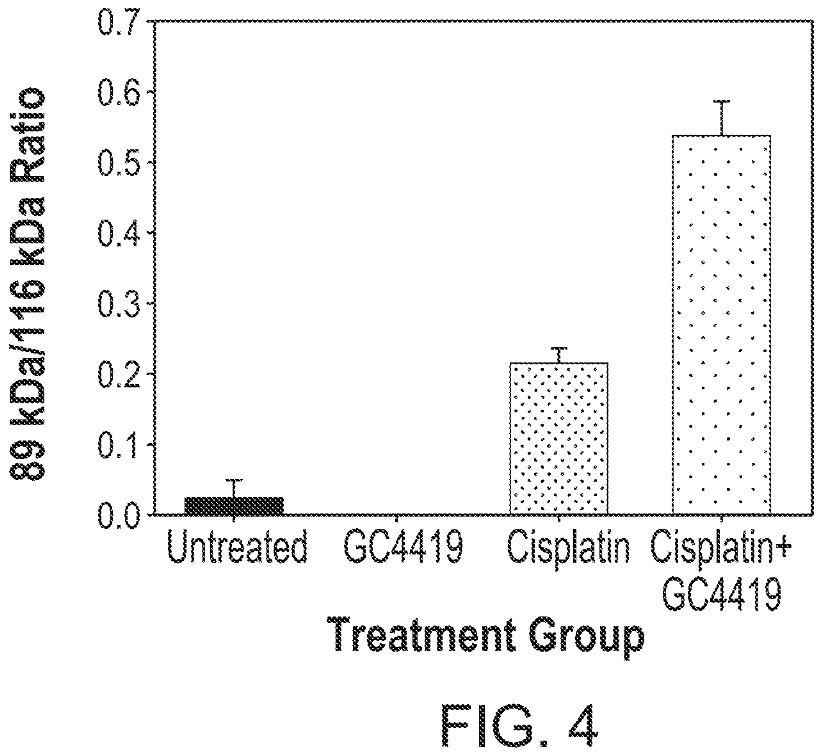
FIG. 4 shows an effect of GC4419 and cisplatin on PARP activation H1299 cells.

H1299 (wild type) NSCLC cells in culture were also treated with 24 μM GC4419 and 10 μM cisplatin for 24 hr. At this time cells were solubilized and PARP activity was measured by Western blot as the ratio of the 89 kd active form to the 116 kd inactive form. As shown in FIG. 4 and consistent with the effects seen in H460 lung carcinoma cells, cisplatin increased PARP activity compared to untreated cells or GC4419 treatment alone. The addition of GC4419 to cisplatin further and significantly $p<0.01$) increased PARP activity, suggesting that GC4419 increased the cancer cell damage caused by cisplatin (see FIG. 4: Effect of GC4419 and Cisplatin on PARP Activation in H1299 Cells).

Figure 5:
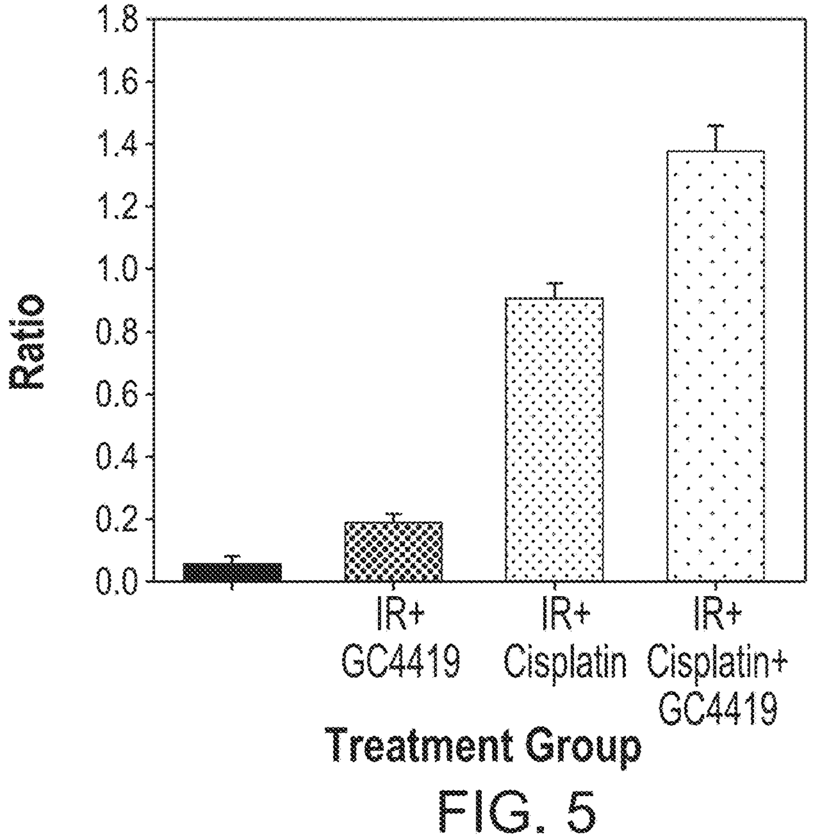
FIG. 5 shows an effect of GC4419, cisplatin and radiation on PARP activation in H460 cells.

H460 cells in culture were further exposed to 6 Gy irradiation (IR), and either 24 μM GC4419, 1 μM cisplatin, or GC4419 and cisplatin for 24 hr. At this time cells were solubilized and PARP activity was measured by Western blot as the ratio of the 89 kd active form to the 116 kd inactive form. As shown in FIG. 5, radiation (IR) alone increased PARP activity significantly ($p<0.05$) over background. The addition of GC4419 to IR significantly increased PARP activity over that seen with radiation alone. Cisplatin added to IR caused a larger increase in PARP activity and GC4419 added to this combination significantly increased ($p<0.01$) this, suggesting that GC4419 increased the cancer cell damage caused by radiation and cisplatin (see, FIG. 5: Effect of GC4419, Cisplatin and Radiation on PARP Activation in H460 Cells).

Figure 6A:
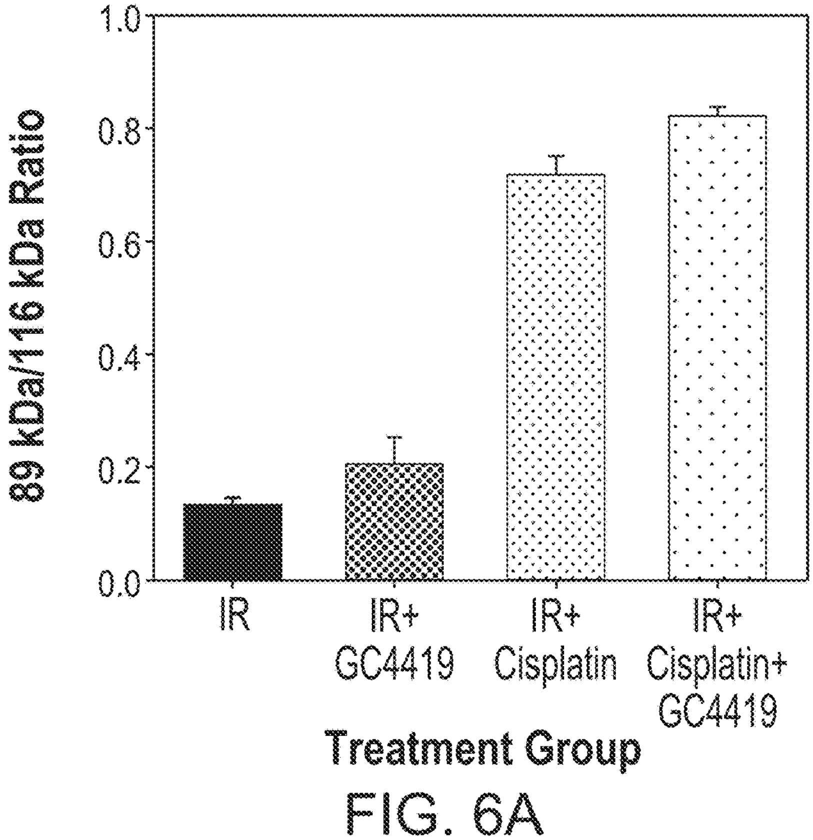
FIG. 6A shows an effect of GC4419, cisplatin and radiation on PARP activation in H1299 cells.

H1299 (wild type) cells in culture were also exposed to 6 Gy irradiation (IR), and either 24 μM GC4419, 1 μM cisplatin, or GC4419 and cisplatin for 24 hr. At this time cells were solubilized and PARP activity was measured by Western blot as the ratio of the 89 kd active form to the 116 kd inactive form. As shown in FIG. 6A and consistent with the effects seen in H460 lung carcinoma cells, radiation (IR) alone increased PARP activity slightly over background. The addition of GC4419 to IR significantly increased PARP activity over that seen with radiation alone. Cisplatin added to IR caused a larger increase in PARP activity and GC4419 added to this combination significantly increased ($p<0.0.05$) this, suggesting that GC4419 increased the cancer cell damage caused by radiation and cisplatin (see, FIG. 6A: Effects of GC4419, Cisplatin and Radiation on PARP Activation in H1299 Cells).

Figure 6B:
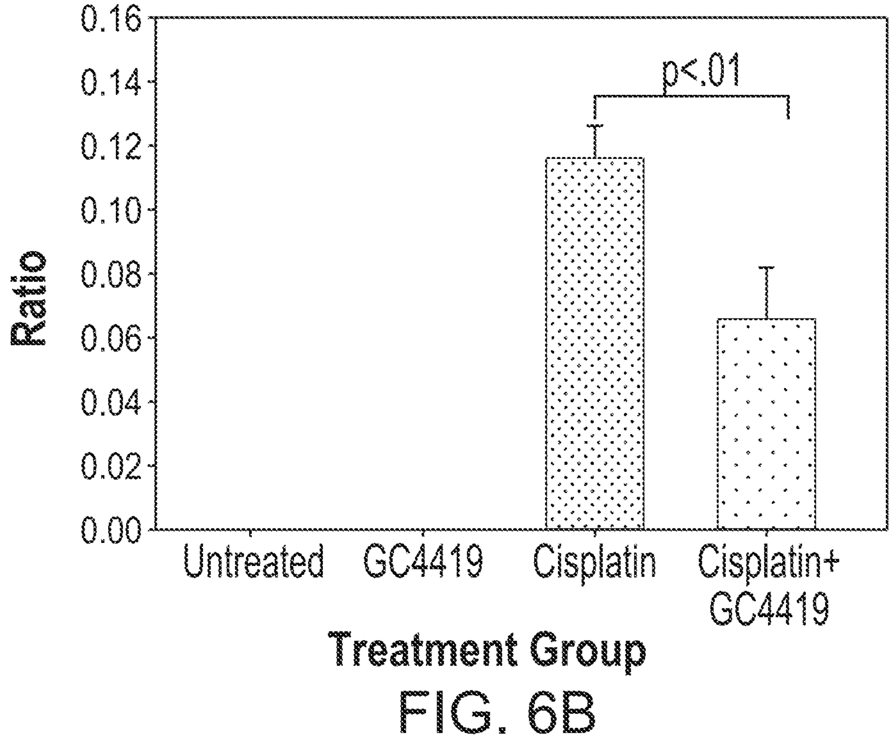
FIG. 6B shows treatment of H1299CAT cells with cisplatin and GC4419.
Figure 6C:
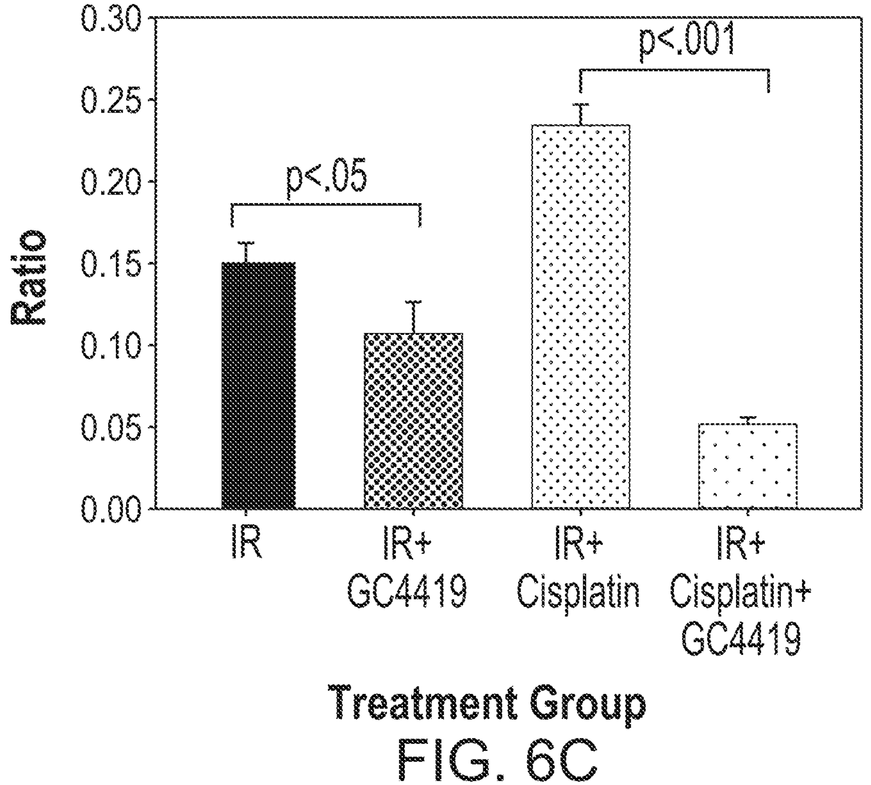
FIG. 6C shows treatment of H1299CAT cells with cisplatin, IR and GC4419.
Figure 7A:
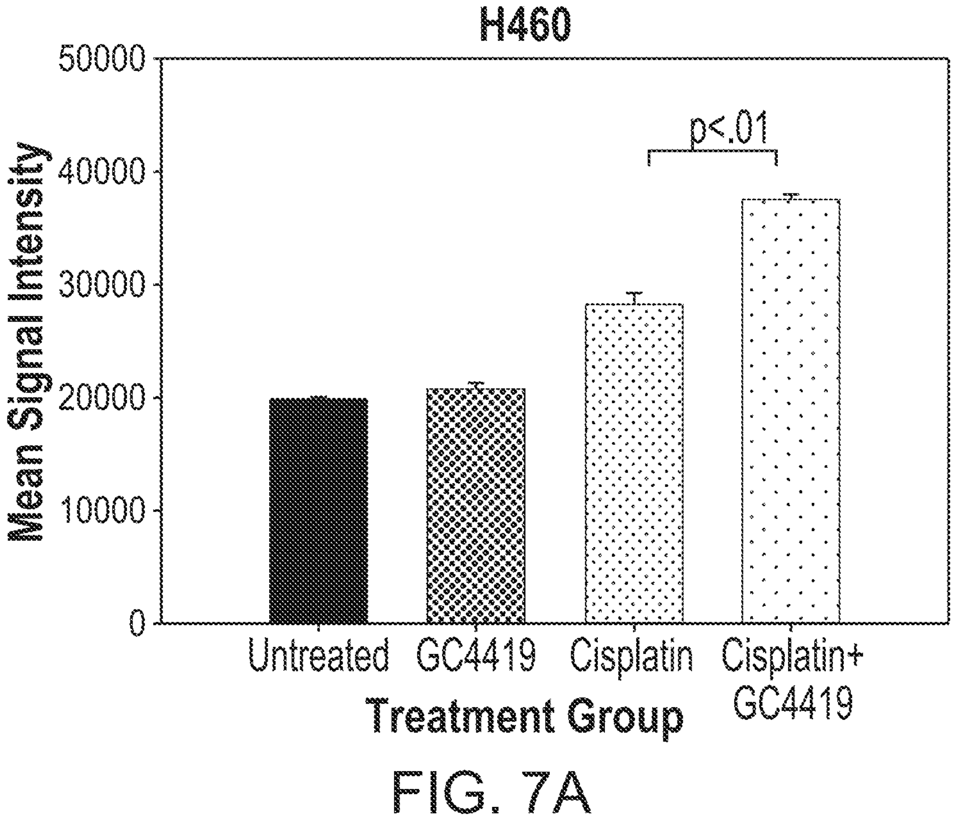
FIGS. 7A-7D show total reactive oxygen species in cancer cell lines with treatment with cisplatin and GC4419.
Figure 7B:
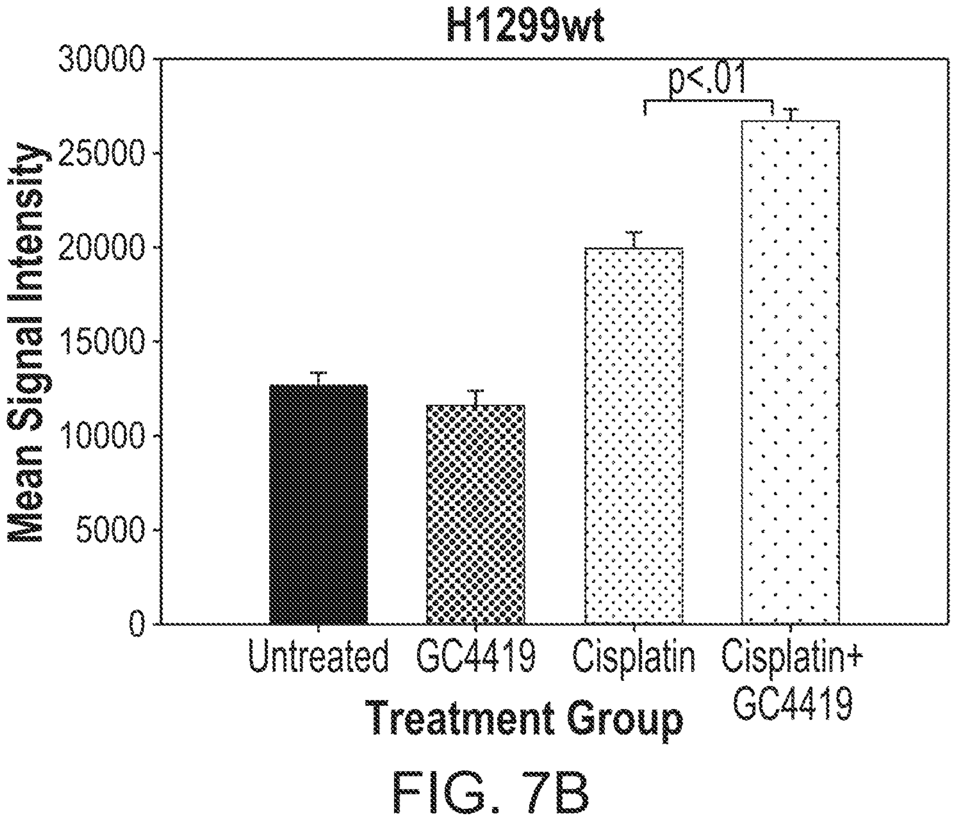
Figure 7C:
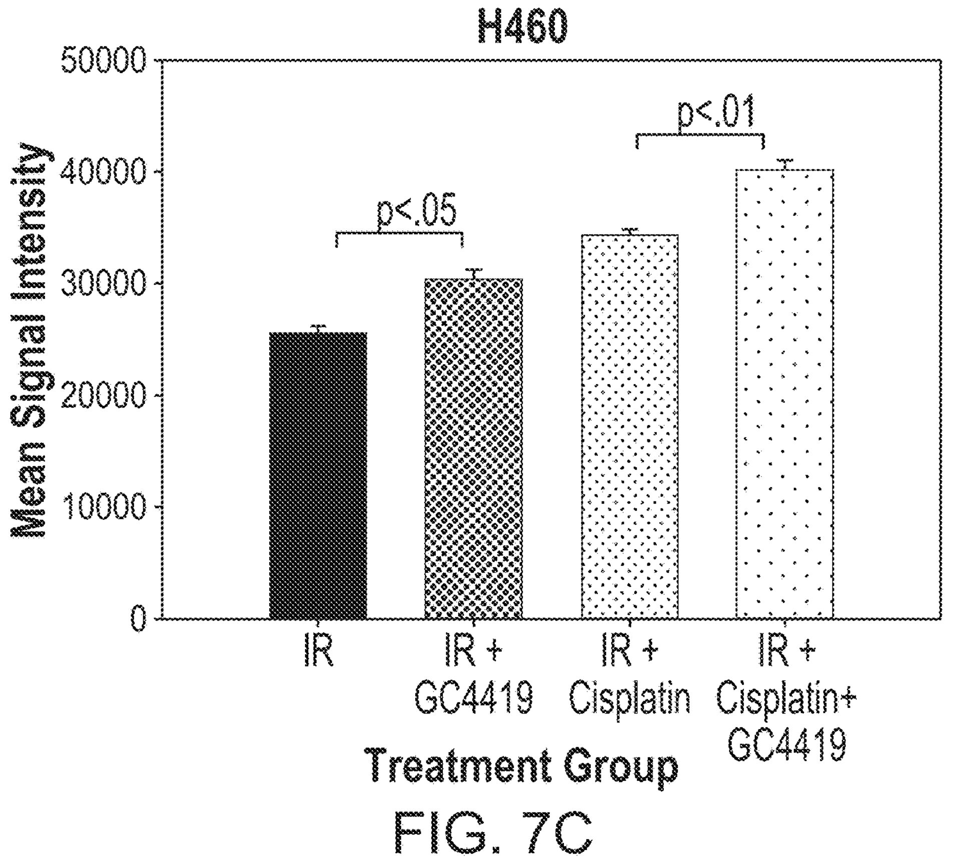
Figure 7D:
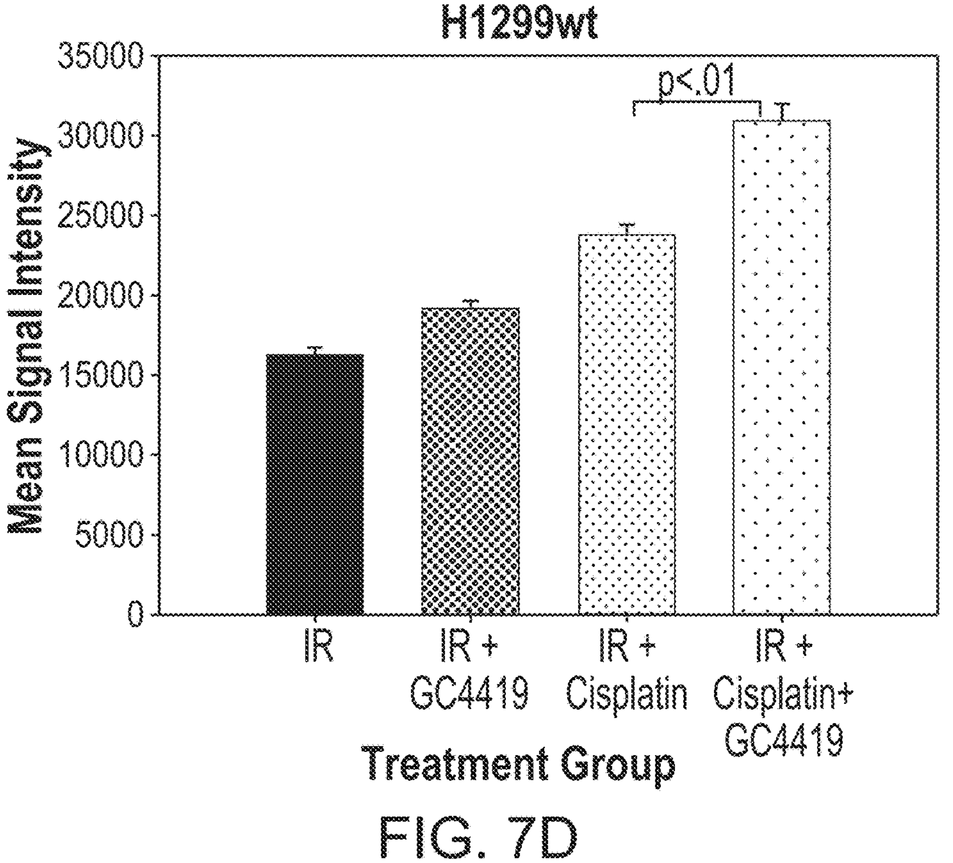
Figure 8A:
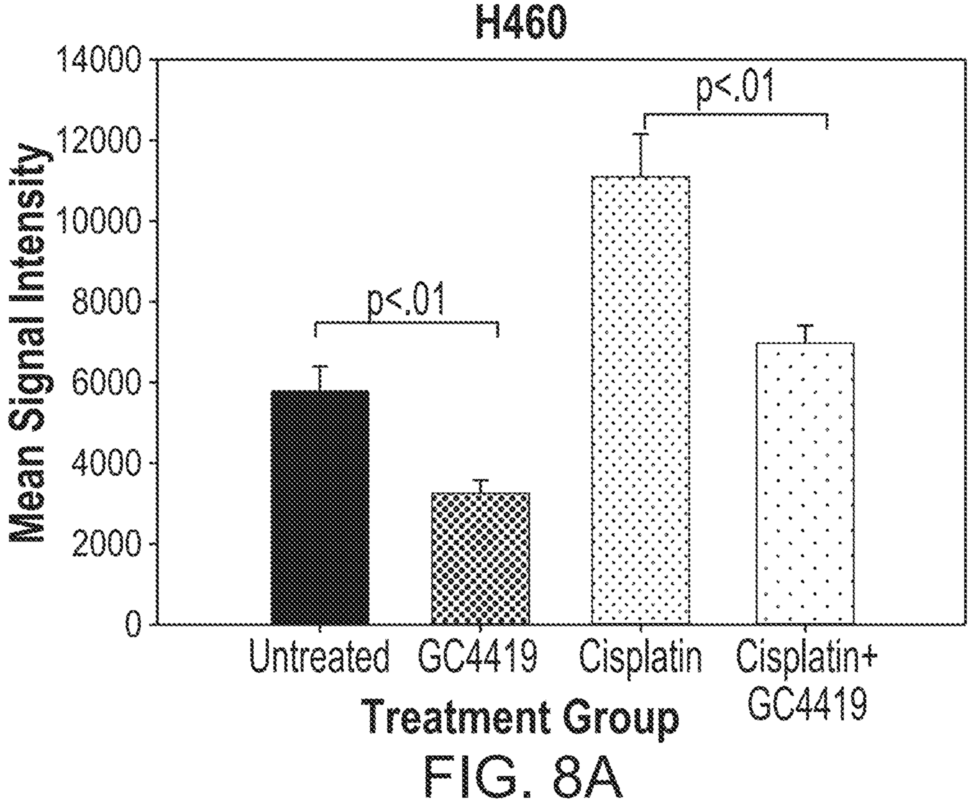
FIGS. 8A-8D show mitochondrial superoxide in cancer cells with treatment with cisplatin and GC4419.
Figure 8B:
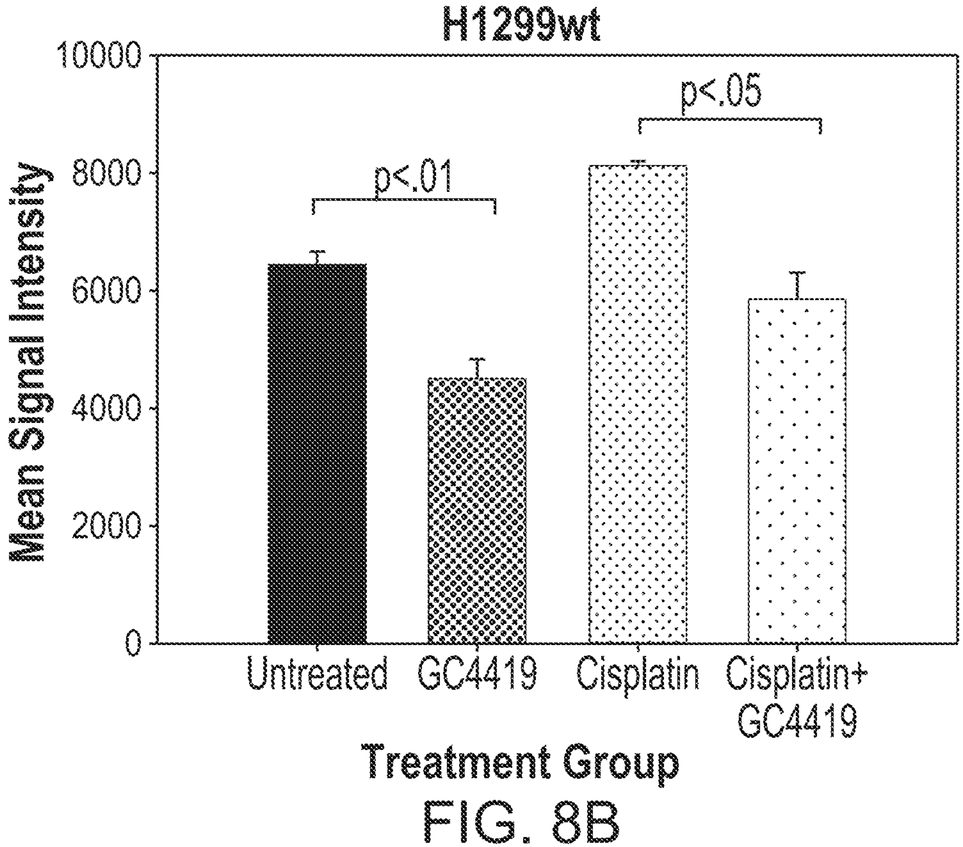
Figure 8C:
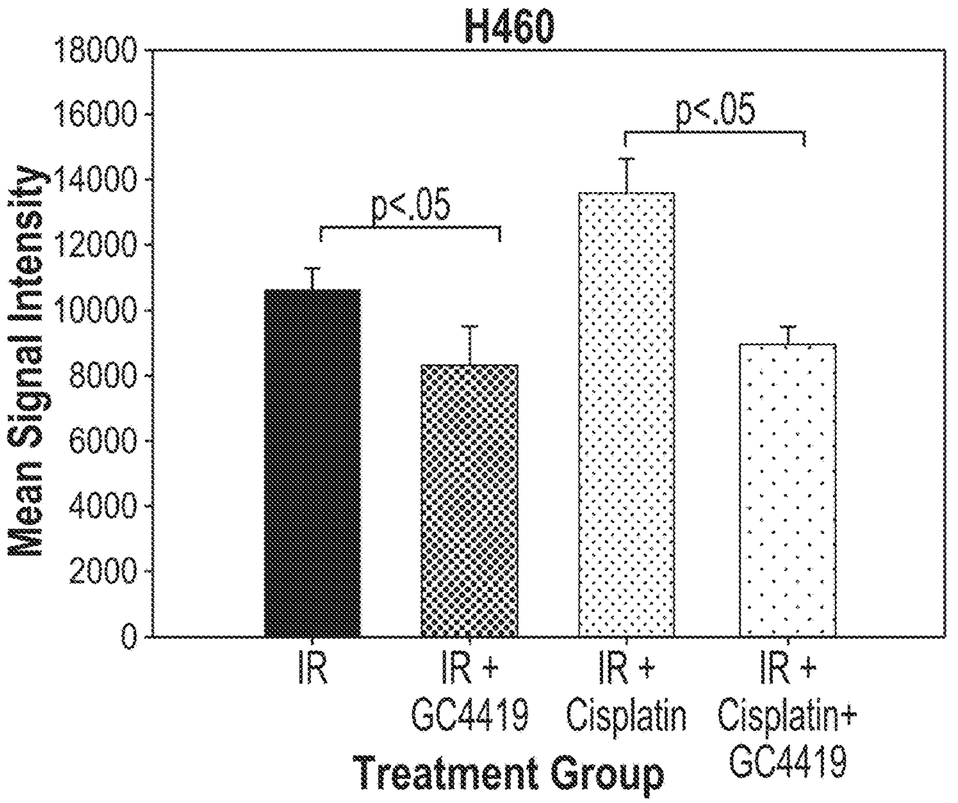
Figure 8D:
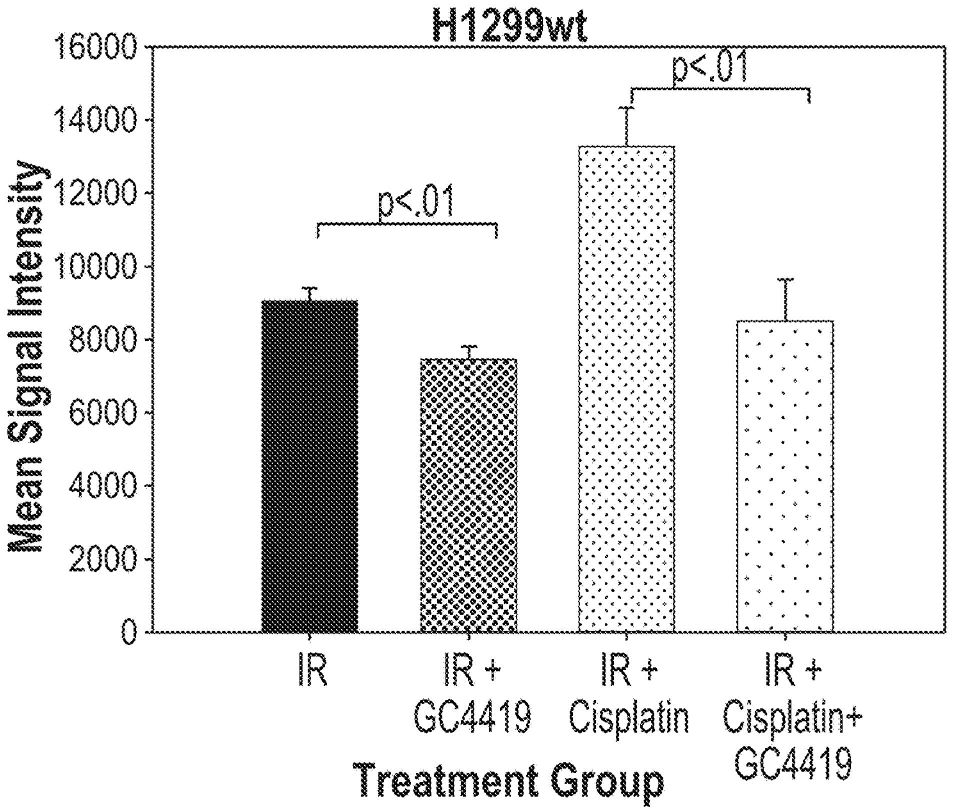
Figure 9A:
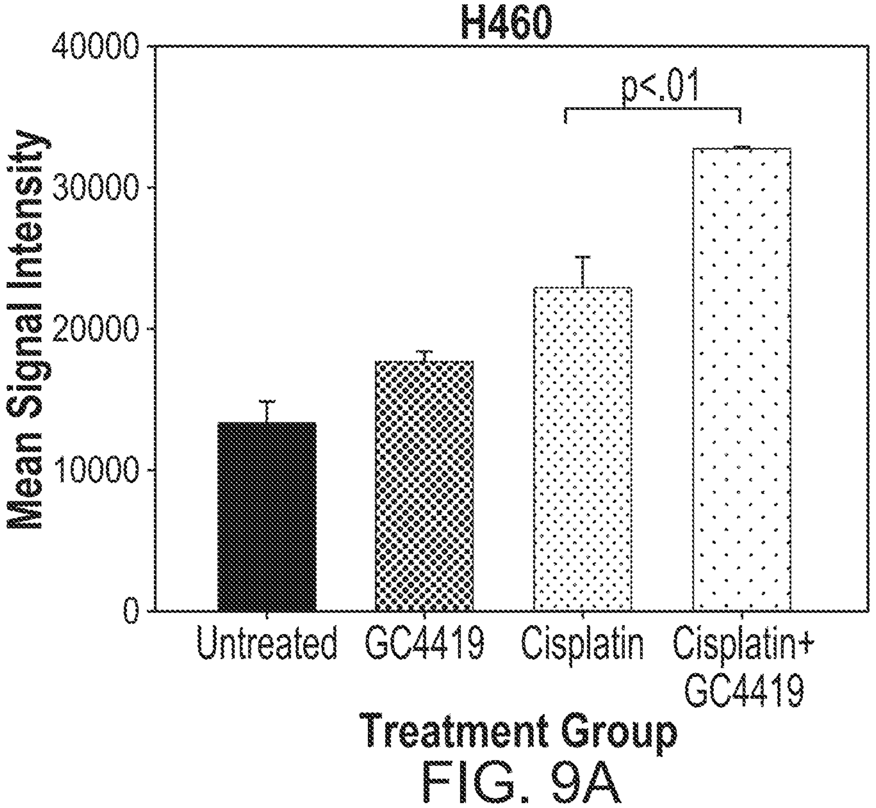
FIGS. 9A-9D show hydrogen peroxide in cancer cells with treatment with cisplatin and GC4419.
Figure 9B:
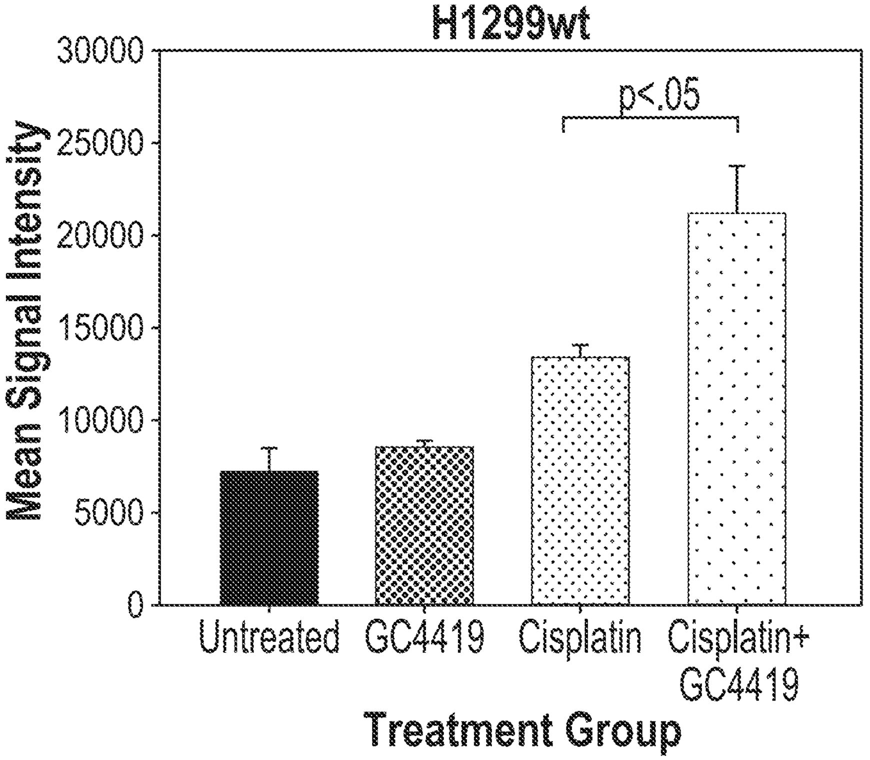
Figure 9C:
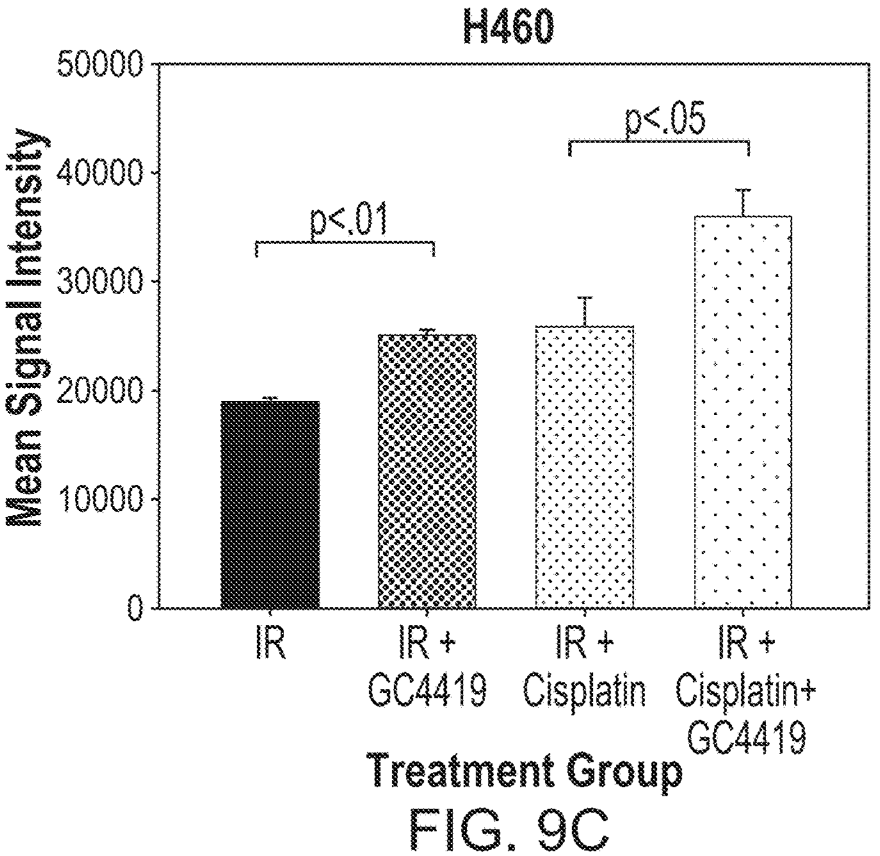
Figure 9D:
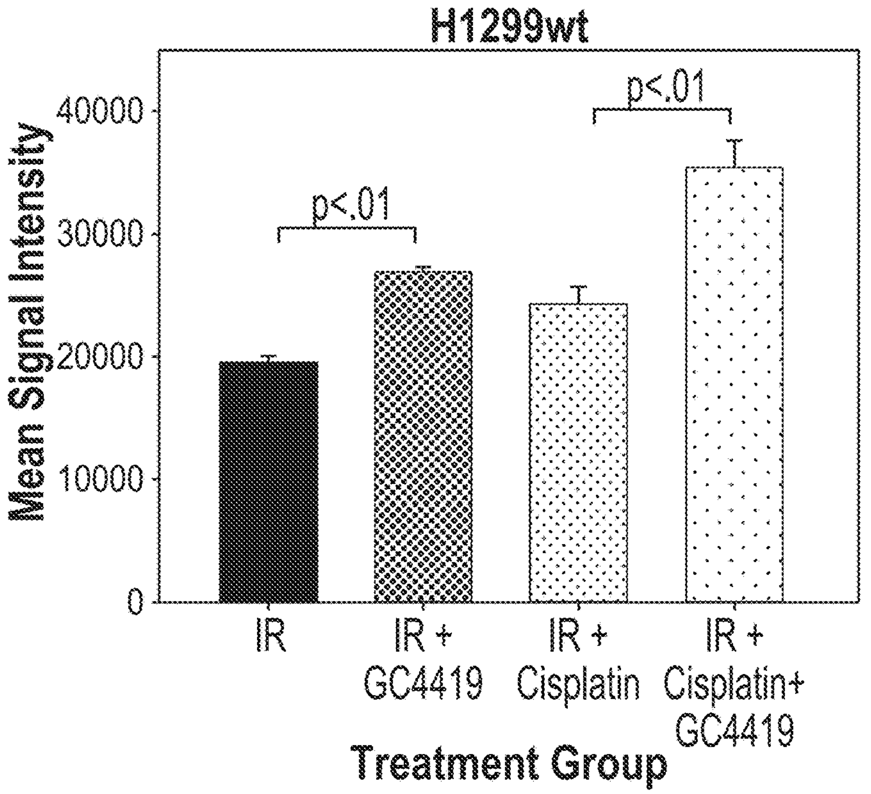

H1299CAT cells were also exposed to 6 Gy irradiation (IR), 24 μM GC4419, and/or 1 μM cisplatin for 24 hr. When treated with doxcycline, H1299CAT cells express greater levels of human catalase (CAT) than the “parent” cells, H1299 (wild type), eliminating all or part of the $H_2O_2$ generated from superoxide by GC4419 or other Mn pentaazamacrocyclic dismutase mimetcs. PARP activation in H1299CAT cells not exposed to doxycycline (data not shown) responded to cisplatin, IR and GC4419 treatments comparably to H1299 wild type cells (see FIG. 5). But when CAT expression was induced in H1299CAT with doxycycline treatment, GC4419 significantly ($p<0.05$) reduced the PARP activation response to cisplatin ($p<0.01$, FIG. 6B), IR ($p<0.05$, FIG. 6C) and to IR+cisplatin ($p<0.001$, FIG. 6C). These results strongly suggest that superoxide generated by cisplatin causes cellular damage, and that GC4419 removal of this superoxide can reduce cellular damage, consistent with the results reported in Example 5 below for reduction of cisplatin nephrotoxicity and hematotoxicity. However, since GC4419 increased PARP response to cisplatin in cancer cells, except when $H_2O_2$ when was removed by CAT overexpression, these results further support that GC4419-generated $H_2O_2$ (unless removed by CAT) was responsible for greater enhancement of cisplatin cellular damage and PARP activation than the superoxide it replaced (see, FIG. 6B: Treatment of H1299CAT cells (with doxycycline induction of CAT overexpression) with Cisplatin and GC4419; and FIG. 6C: Treatment of H1299CAT cells (with doxycycline induction of CAT overexpression) with cisplatin, IR and GC4419).

Example 4

Cisplatin Treatment Increases Total Reactive Oxygen Species (ROS) Levels in Cancer Cells While GC4419 Selectively Decreases Superoxide and Increases $H_2O_2$ Levels. H460 and H1299 (wild type) cells were exposed to 6 Gy irradiation (IR), and either 24 μM GC4419, 1 μM cisplatin, or GC4419 and cisplatin. After the treatments and incubations CellROX fluorogenic probes for total ROS were added for 30 minutes continued incubation and the CellROX signal was measured using a flow cytometer. FIGS. 7A-7D show that GC4419 had little effect on total ROS when used alone on either cancer cell line, while cisplatin or cisplatin plus IR increased total ROS. GC4419 appeared to have a synergistic effect on total ROS when added to cisplatin therapy (see, FIGS. 7A-7D: Total Reactive Oxygen Species).

If instead, after the treatments and initial incubations, MitoSOX fluorogenic probe for mitochondrial superoxide was added for 10 minutes continued incubation and the MitoSOX signal was measured using a flow cytometer, FIGS. 8A-8D show that GC4419 significantly reduced the basal levels of mitochondrial superoxide in both cancer cell lines. In addition, GC4419 significantly reduced the increase in mitochondrial superoxide induced by cisplatin or cisplatin plus IR (see, FIGS. 8A-8D: Mitochondrial Superoxide)

In addition, if instead, after the treatments and initial incubations, P0-1 probe for $H_2O_2$ was added, FIGS. 9A-9D show that GC4419 significantly increases both the basal levels of $H_2O_2$, and significantly further increases the increase in $H_2O_2$ induced by cisplatin or cisplatin plus IR, in both cancer cell lines (see, FIGS. 9A-9D: Hydrogen Peroxide).

Reduced Toxicity of Platinum-Based Anticancer Agents

Example 5

Effect of GC4419 on Cisplatin-induced Nephrotoxicity in Mice. 4 month old male C57BL/6J mice (young) were purchased from Jackson Laboratories and 18 month old mice (old) were obtained as collaboration with Dr. Amy Sindler (University of Iowa) from the National institute of Aging. All mice were maintained in accordance with ACURF approval #4121235 at the University of Iowa Animal Care facility. Mice were maintained on normal diets and water ad libitum through the course of the experiment. Animals were randomly assigned to experimental groups which included vehicle control, cisplatin only, GC4419 and cisplatin+GC4419.

A cisplatin-induced acute kidney injury (AKI) model was as follows: Male C57BL/6J mice, either 4 months or 18 months of age were administered a single dose of 10 mg/kg cisplatin or 0.9% saline by i.p, injection. Animals were sacrificed 72 hours following cisplatin treatment. Animals in GC4419 only and cisplatin+GC4419 groups were treated with 10 mg/kg GC4419 daily starting 4 days prior to the cisplatin dose and until the day of euthanasia. Animals in the cisplatin only group were also given a bolus dose of saline every day following cisplatin treatment to avoid dehydration.

Whole blood urea nitrogen (BUN) and creatinine levels were measured using an i-STAT handheld clinical analyzer purchased from Abbott-Point of Care (Princeton, NJ) using single-use i-STAT test cartridges (Chem8+) prior to the start of treatment with GC4419 and 72 hours following cisplatin treatment. Animals were weighed every other day following the start of treatment with GC4419.

Figure 10A:
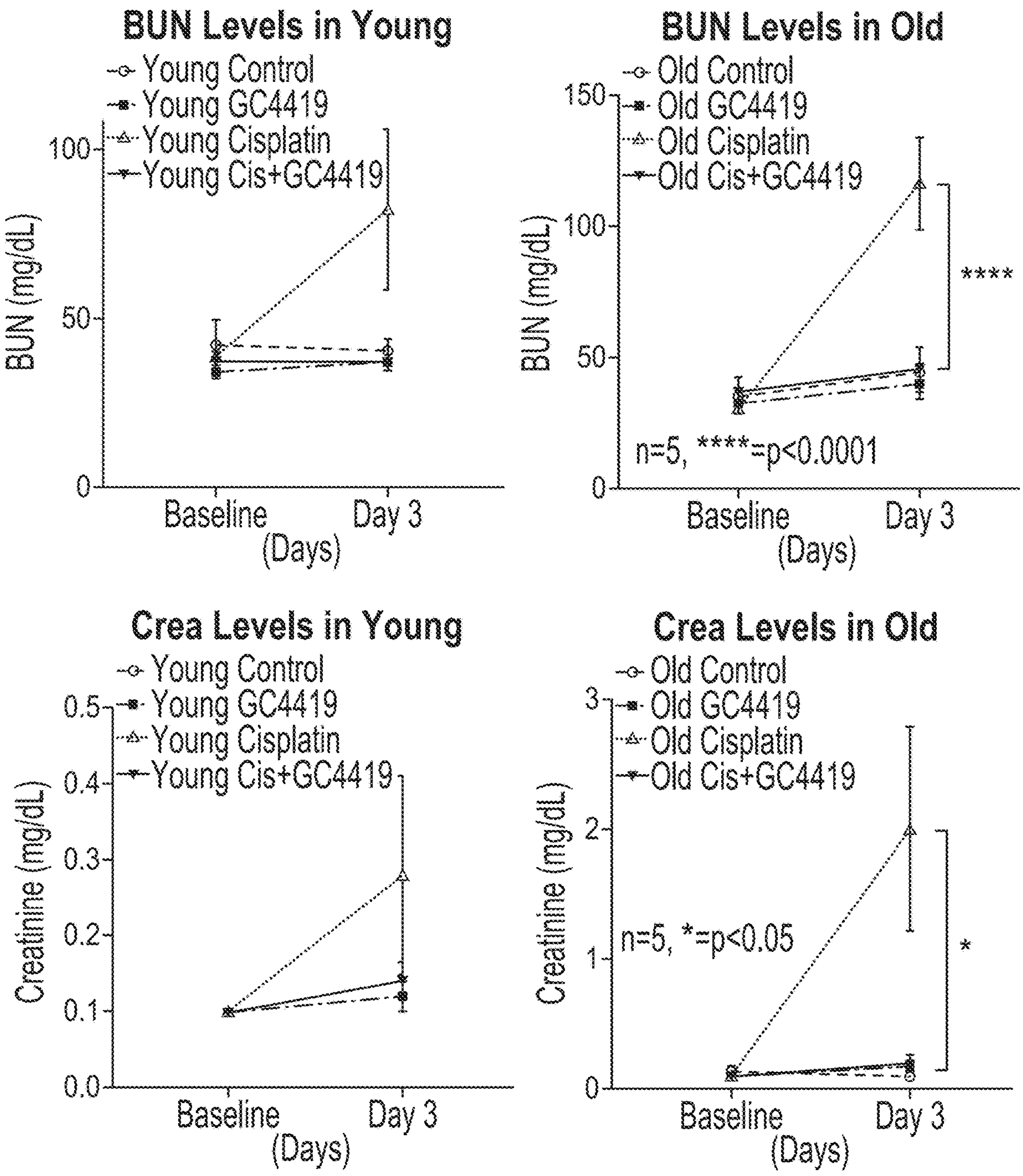
FIG. 10A shows BUN and creatinine Levels in cisplatin-treated mice.

As seen in FIG. 10A, cisplatin increased BUN and creatinine levels three days after administration, both in young, and more dramatically in old, mice, indicating significant impairment of kidney function. GC4419 completely prevented these increases in BUN and creatinine, suggesting that it prevented acute kidney injury (see FIG. 10A: BUN and Creatinine Levels in Cisplatin-treated Mice).

Figure 10B:
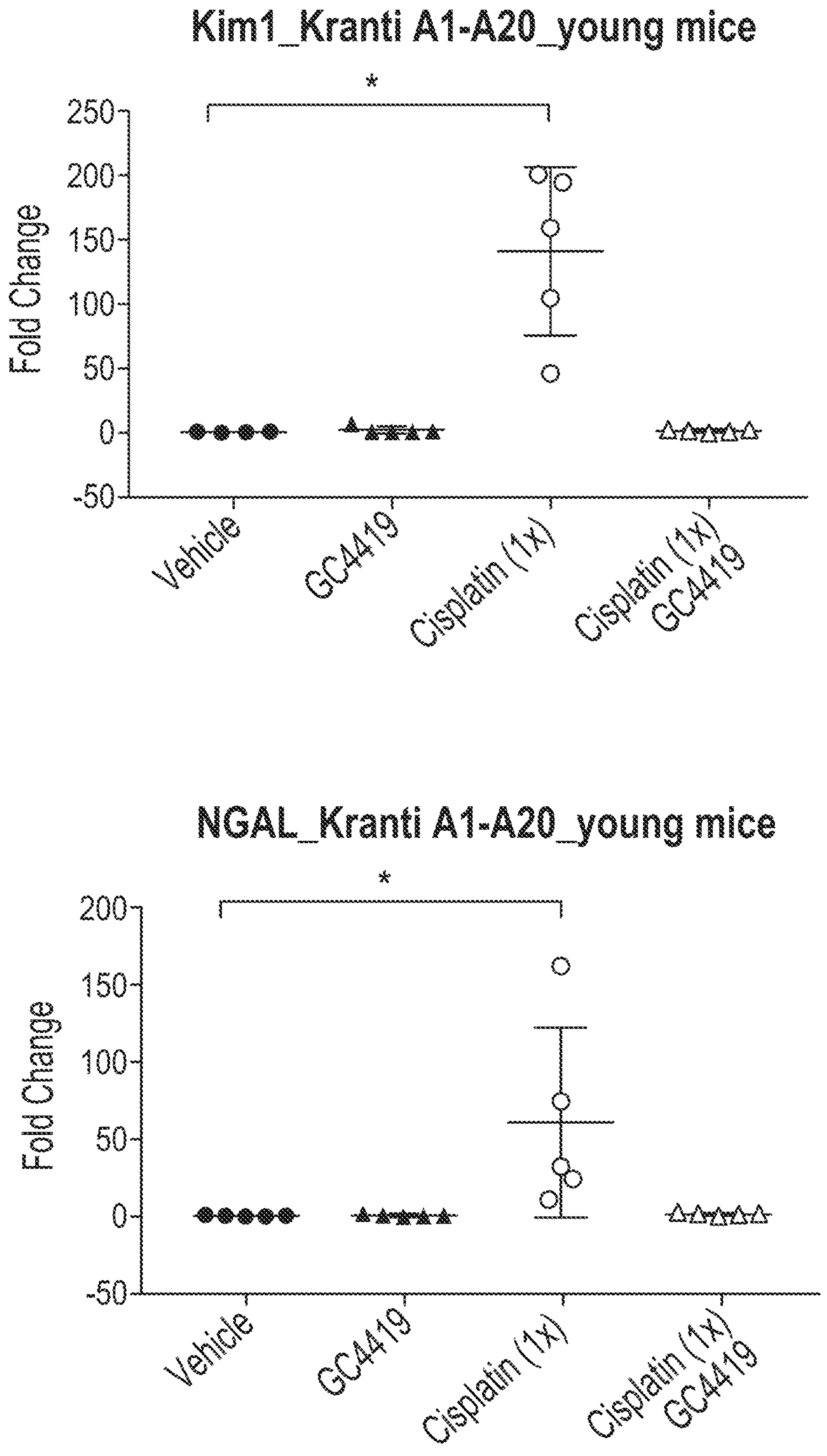
FIG. 10B shows KIM1 and NGAL biomarkers in cisplatin-treated mice.

Two specific biomarkers of kidney injury, kidney injury molecule 1 (KIM1) and neutrophil gelatinase-associated lipocalin (NGAL) were also assessed. As seen in FIG. 10B, these biomarkers are consistent with the BUN and creatinine levels, demonstrating that cisplatin caused nephrotoxicity and GC4419 prevented that injury (see, FIG. 10B: KIM1 and NGAL biomarkers in Cisplatin-treated Mice).

Figure 10C:
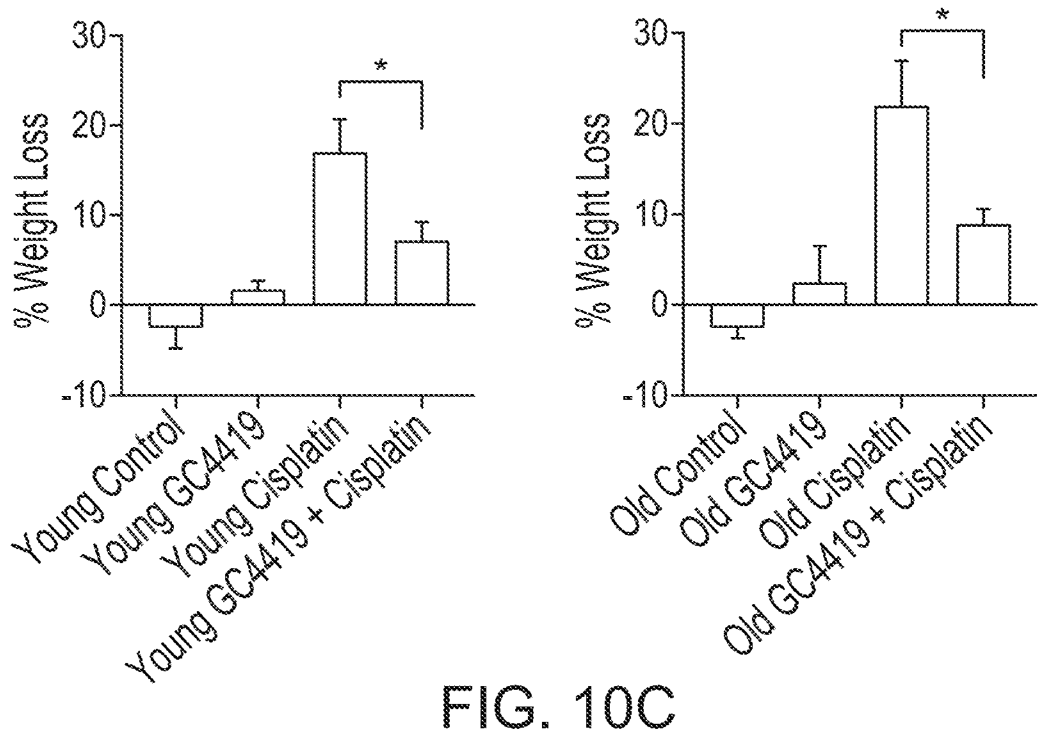
FIG. 10C shows cisplatin-induced weight loss.
Figure 10D:
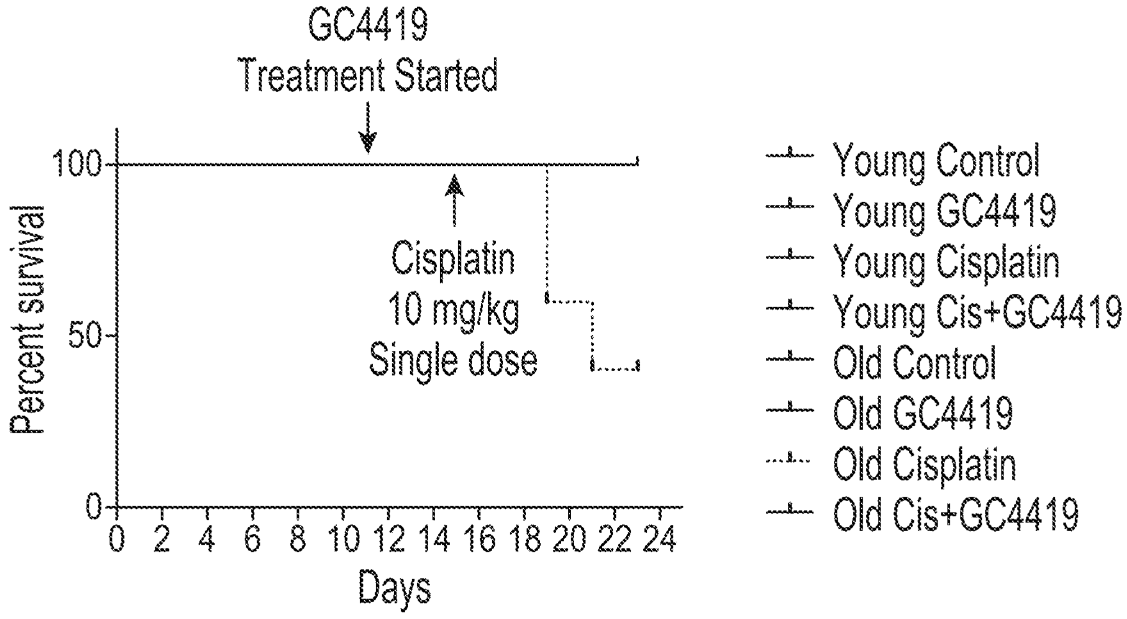
FIG. 10D shows survival in cisplatin-treated mice.

Further consistent with these kidney injury and function results, cisplatin caused significant weight loss in both young and old mice (FIG. 10C) and decreased survival in the more sensitive old mice (FIG. 10D). GC4419 reduced the amount of weight loss in both sets of mice and prevented cisplatin mortality in the old mice (see, FIG. 10C: Cisplatin-induced Weight Loss; and FIG. 10D: Survival in Cisplatin-treated Mice).

Further consistent with these kidney injury and function results, cisplatin caused significant weight loss in both young and old mice (FIG. 10C) and decreased survival in the more sensitive old mice (FIG. 10D). GC4419 reduced the amount of weight loss in both sets of mice and prevented cisplatin mortality in the old mice.

Example 6

Effect of GC4419 on Cisplatin-induced Hematotoxicity in Mice. 7 week old athymic female Nu/Nu (nude) mice were implanted in a hind leg with SQ20B human head and neck squamous cell carcinoma cells. After tumors had been allowed to form and grow for 4 days, the mice received either no treatment or 2.7 mg/kg cisplatin and 2 Gy radiation (IR) every second or third day for five times. In addition, one group that received cisplatin and IR treatment also received 10 mg/kg GC4419 every day during the treatment period and for two days following. Mice were assessed for blood counts by tail vein blood collection either 2 days or 2 weeks after the treatment period.

Figure 11A:
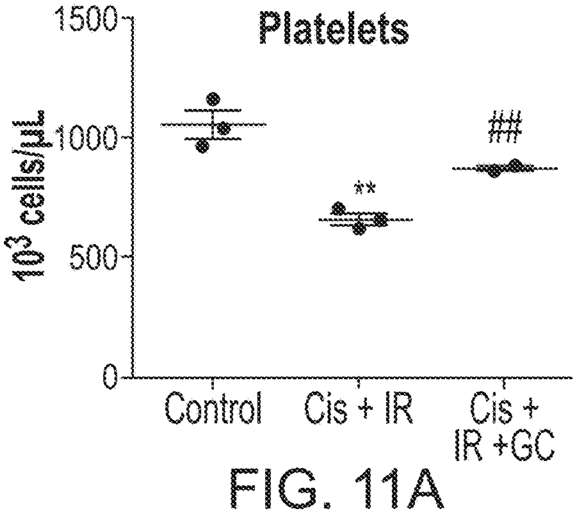
FIG. 11A shows cisplatin-induced thrombocytopenia.

As seen in FIG. 11A, cisplatin+IR treatment resulted in a decrease in platelets (thrombocytopenia) measured two days after the end of treatments and GC4419 significantly restored platelet levels (see, FIG. 11A: Cisplatin-induced Thrombocytopenia).

Figure 11B:
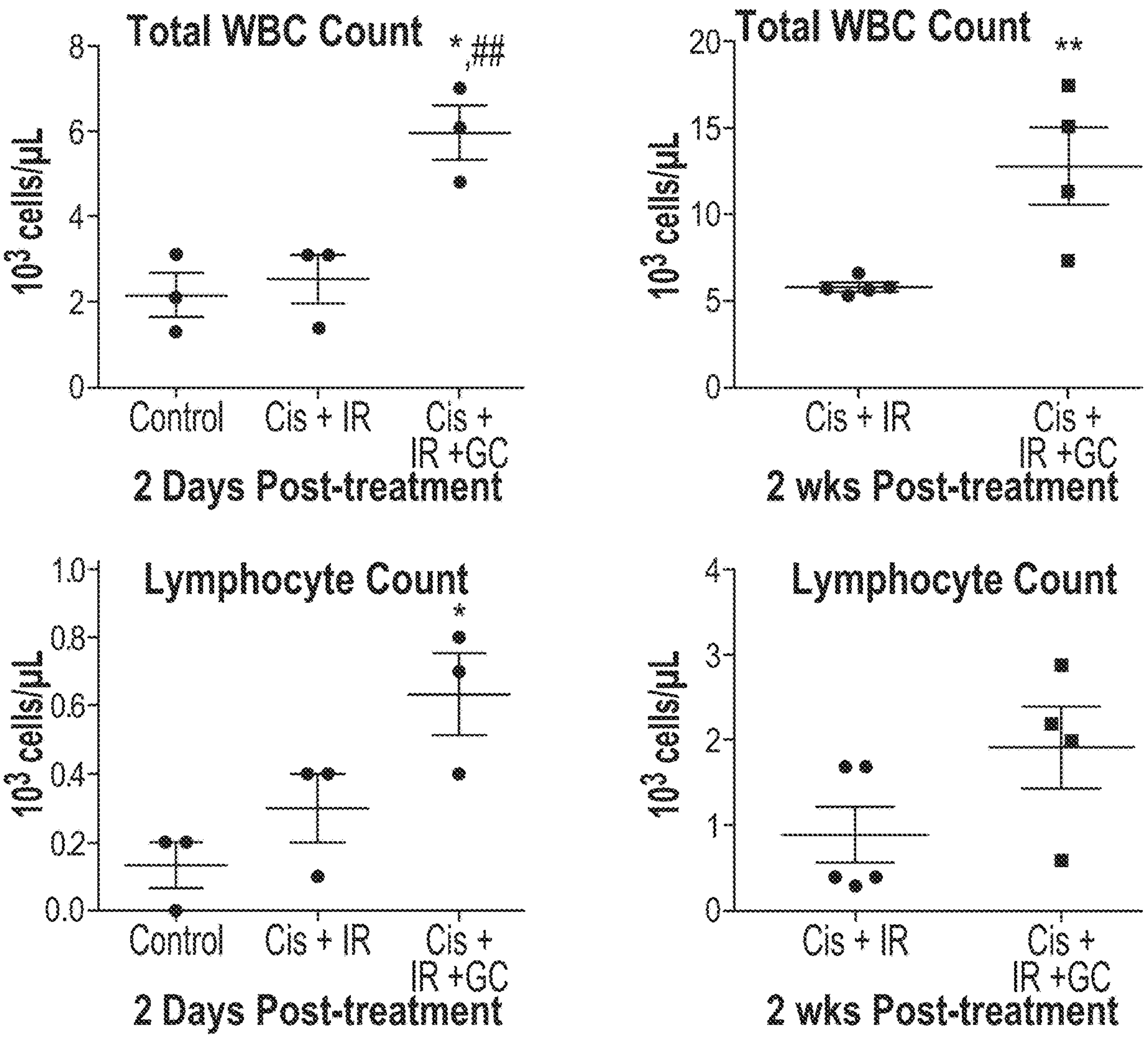
FIG. 11B shows GC4419 and white blood cell count.

As seen in FIG. 11B GC4419 treatment stimulated leukocyte (WBC) and proportionally lymphocyte subset production in mice treated with the combination of cisplatin and radiation at both 2 days and 2 weeks after the end of treatment (see, FIG. 11B: GC4419 and WBC Count).

Figure 11C:
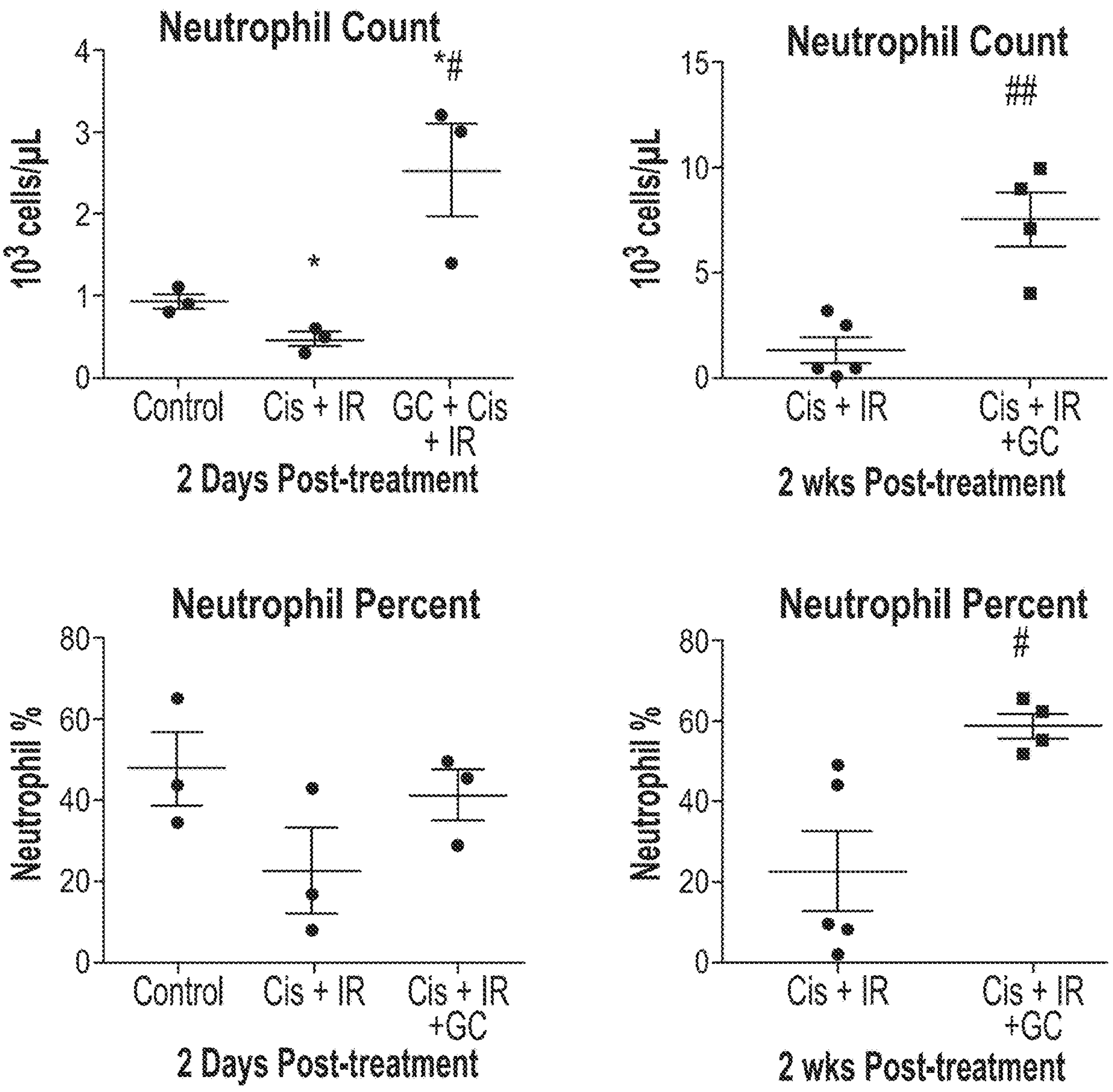
FIG. 11C shows cisplatin-induced neutropenia.

As seen in FIG. 11C, cisplatin+IR treatment resulted in a decrease in neutrophil count and percentage (neutropenia), measured two days or two weeks after the end of treatments and GC4419 maintained neutrophil percentage at apparently normal levels (see, FIG. 11C: Cisplatin-induced Neutropenia).

Figure 11D:
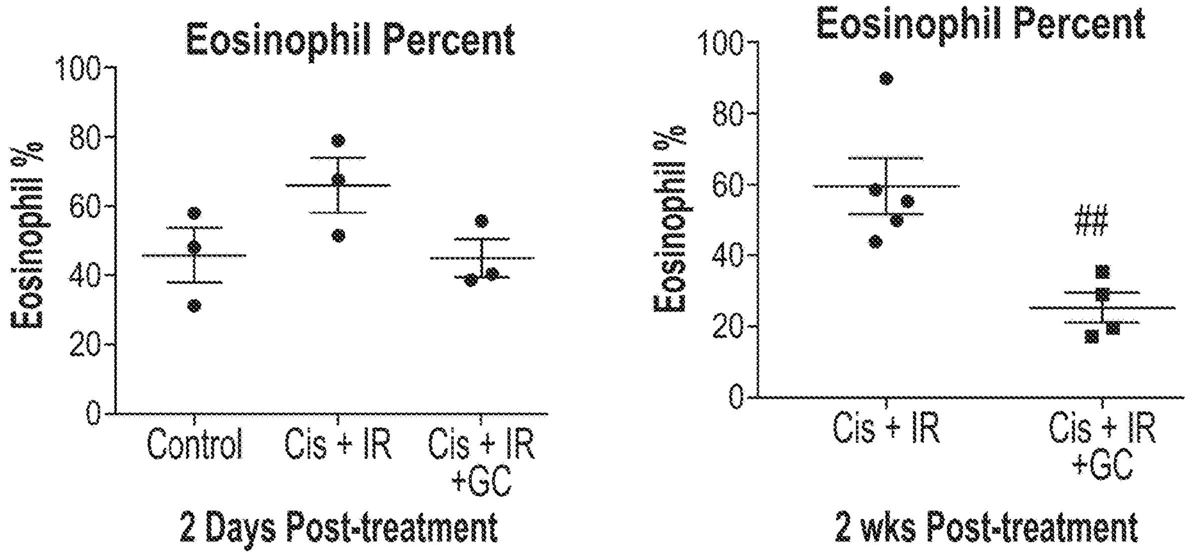
FIG. 11D shows cisplatin-induced eospinophil increase.

Conversely, as seen in FIG. 11D, cisplatin+IR treatment resulted in an increase in eosinophil percentage, measured two days or two weeks after the end of treatments and GC4419 maintained eosinophil percentage at apparently normal levels (see, FIG. 11D: Cisplatin-induced Eospinophil Increase).

The following are exemplary embodiments of aspects of the disclosure, but are not intended to be limiting, and the disclosure may encompass further aspects.

Embodiment 1. A method of treating and/or reducing the reducing toxic effects to a mammalian subject associated with treatment with a platinum-based anti-cancer agent in a subject in need thereof, the method comprising administering to the subject a therapeutically effective amount of a platinum-based anticancer agent; and administering to the subject a therapeutically effective amount of a pentaaza macrocyclic ring complex corresponding to the Formula (I) below, prior to, concomitantly with, or after administration of the platinum-based anticancer agent, to reduce toxic effects of the platinum-based anti-cancer agent:

(I)

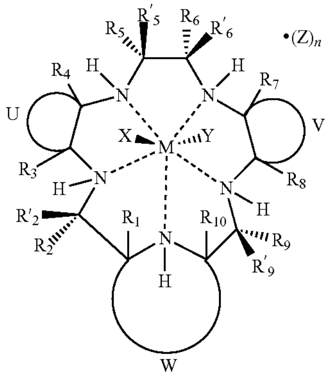

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$NR_{11}R_{12}$, —$COR_{11}$, —$CO_2R_1$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Embodiment 2. The method according to Embodiment 1, wherein the subject is afflicted with cancer.

Embodiment 3. The method according to Embodiment 1 or 2, wherein the subject is afflicted with and/or at risk for a toxicity induced by treatment with the platinum-based anti-cancer agent, that is a toxicity selected from the group consisting of nephrotoxicity, myelotoxicity, and ototoxicity Embodiment 4. The method according to any one of Embodiments 1-3, wherein the subject is afflicted with and/or at risk for one or more of nephrotoxicity and myelotoxicity.

Embodiment 5. The method according to any one of Embodiments 1-4, wherein the subject is suffering from nephrotoxicity and/or myelotoxicity associated with treatment with the platinum-based anti-cancer agent.

Embodiment 6. The method according to any one of Embodiments 1-5, comprising administering therapeutically effective amounts of the platinum-based anti-cancer agent and the pentaaza macrocyclic ring complex that increase treatment response to the platinum-based anti-cancer agent.

Embodiment 7. The method of any of Embodiments 1-6, wherein the pentaaza macrocyclic ring complex is administered in a therapeutically effective amount that results in an increase in cancer response corresponding to any selected from the group consisting of reduced tumor volume, reduced tumor growth rate, increased survival, reduced occurrence and/or extent of metastasis, and reduced proliferation of cancer cells.

Embodiment 8. The method of any of Embodiments 1-7, wherein the pentaaza macrocyclic ring is administered in a therapeutically effective amount that reduces levels of at least one of creatine and blood urea nitrogen (BUN).

Embodiment 9. The method of any of Embodiments 1-8, wherein the pentaaza macrocyclic ring is administered in a therapeutically effective amount that reduces levels of markers for kidney damage selected from the group consisting of kidney injury molecule 1 (KIM1) and neutrophil gelatinase-associated lipocalin (NGAL)

Embodiment 10. A method of treating and/or reducing the risk for a toxic effect associated with treatment with a platinum-based anti-cancer agent in a mammalian subject in need thereof, the method comprising: administering to the subject a pentaaza macrocyclic ring complex corresponding to the Formula (I) below, prior to, concomitantly with, or after administration of the platinum-based anticancer agent, to reduce toxic effects of the platinum-based anti-cancer agent:

(I)

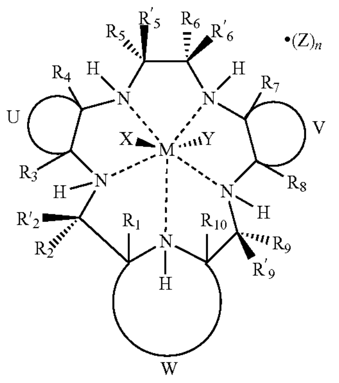

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$NR_{11}R_{12}$, —$COR_{11}$, —$CO_2R_{11}$, —$CONR_{11}R_{12}$, —$SR_{11}$, —$SOR_{11}$, —$SO_2R$ 11, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Embodiment 11. The method according to Embodiment 10, wherein the subject is afflicted with cancer.

Embodiment 12. The method according to Embodiment 10 or 11, wherein the subject is afflicted with and/or at risk for a toxicity induced by treatment with the platinum-based anti-cancer agent, that is a toxicity selected from the group consisting of nephrotoxicity, myelotoxicity, and ototoxicity.

Embodiment 13. The method according to any one of Embodiments 10-12, wherein the subject is afflicted with and/or at risk for one or more of nephrotoxicity and myelotoxicity.

Embodiment 14. The method according to any one of Embodiments 10-13, wherein the subject is suffering from nephrotoxicity and/or myelotoxicity associated with treatment with the platinum-based anti-cancer agent.

Embodiment 15. The method according to any one of Embodiments 10-14, comprising administering therapeutically effective amounts of the platinum-based anti-cancer agent and the pentaaza macrocyclic ring complex that increase treatment response to the platinum-based anti-cancer agent.

Embodiment 16. The method of any one of Embodiments 10-15, wherein the pentaaza macrocyclic ring complex is administered in a therapeutically effective amount that results in an increase in cancer response corresponding to any selected from the group consisting of reduced tumor volume, reduced tumor growth rate, increased survival, reduced occurrence and/or extent of metastasis, and reduced proliferation of cancer cells.

Embodiment 17. The method of any one of Embodiments 10-16, wherein the pentaaza macrocyclic ring is administered in a therapeutically effective amount that reduces levels of at least one of creatine and blood urea nitrogen (BUN).

Embodiment 18. The method of any one of Embodiments 10-17, wherein the pentaaza macrocyclic ring is administered in a therapeutically effective amount that reduces levels of markers for kidney damage selected from the group consisting of kidney injury molecule 1 (KIM1) and neutrophil gelatinase-associated lipocalin (NGAL).

Embodiment 19. A method of treating a cancer in a mammalian subject afflicted with the cancer, the method comprising:

administering to the subject a therapeutically effective amount of a platinum-based anticancer agent;

administering to the subject a therapeutically effective amount of a pentaaza macrocyclic ring complex corresponding to the Formula (I) below, prior to, concomitantly with, or after administration of the platinum-based anticancer agent, whereby response of the cancer to the platinum-based anticancer agent is increased:

(I)

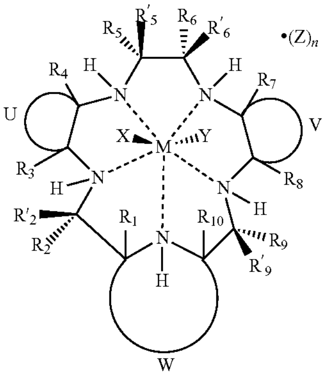

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$NR_{11}R_{12}$, —$COR_{11}$, —$CO_2R_1$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Embodiment 20. The method of Embodiment 19, comprising administering therapeutically effective amounts of the platinum-based anti-cancer agent and the pentaaza macrocyclic ring complex that reduce toxic effects of the platinum anti-cancer agent.

Embodiment 21. The method of Embodiment 19 or 20, wherein the pentaaza macrocyclic ring complex is administered in a therapeutically effective amount that results in an increase in cancer response corresponding to any selected from the group consisting of reduced tumor volume, reduced tumor growth rate, increased survival, reduced occurrence and/or extent of metastasis and reduced proliferation of cancer cells, and/or may decrease cancer complications.

Embodiment 22. The method of Embodiment 19, 20 or 21, wherein the pentaaza macrocyclic ring is administered in a therapeutically effective amount that reduces levels of at least one of creatine and blood urea nitrogen (BUN).

Embodiment 23. The method of Embodiment 19, 20, 21 or 22, wherein the pentaaza macrocyclic ring is administered in a therapeutically effective amount that reduces levels of markers for kidney damage selected from the group consisting of kidney injury molecule 1 (KIM1) and neutrophil gelatinase-associated lipocalin (NGAL).

Embodiment 24. A method of increasing the sensitivity of a mammalian subject to treatment with a platinum-based anti-cancer agent in a subject in need thereof, the method comprising:

administering to the subject a therapeutically effective amount of a pentaaza macrocyclic ring complex corresponding to the Formula (I) below, prior to, concomitantly with, or after administration of the platinum-based anticancer agent, whereby treatment response to the platinum-based anti-cancer agent is increased:

(I)

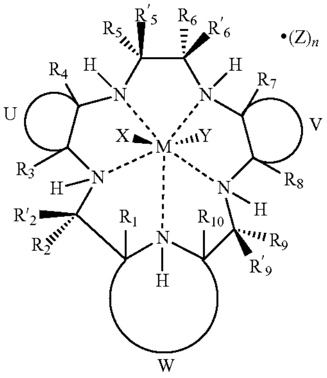

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$NR_{11}R_{12}$, —$COR_{11}$, —$CO_2R_1$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Embodiment 25. The method of Embodiment 24, wherein the subject is afflicted with cancer.

Embodiment 26. The method of Embodiment 24 or 25, comprising administering therapeutically effective amounts of the platinum-based anti-cancer agent and the pentaaza macrocyclic ring complex that reduce toxic effects of the platinum anti-cancer agent.

Embodiment 27. The method of Embodiment 24, 25 or 26, wherein the pentaaza macrocyclic ring complex is administered in a therapeutically effective amount that results in an increase in cancer response corresponding to any selected from the group consisting of reduced tumor volume, reduced tumor growth rate, increased survival, reduced occurrence and/or extent of metastasis, and reduced proliferation of cancer cells, and/or may decrease cancer complications.

Embodiment 28. The method of Embodiment 24, 25, 26 or 27, wherein the pentaaza macrocyclic ring is administered in a therapeutically effective amount that reduces levels of at least one of creatine and blood urea nitrogen (BUN).

Embodiment 29. The method of any of Embodiments 24-28, wherein the pentaaza macrocyclic ring is administered in a therapeutically effective amount that reduces levels of markers for kidney damage selected from the group consisting of kidney injury molecule 1 (KIM1) and neutrophil gelatinase-associated lipocalin (NGAL).

Embodiment 30. A method of treating and/or reducing the risk of a toxic effect selected from the group consisting of nephrotoxicity and myelotoxicity associated with treatment with a platinum-based anti-cancer agent in a mammalian subject in need thereof, the method comprising:

administering to the subject a therapeutically effective amount of a platinum-based anticancer agent; and administering to the subject a therapeutically effective amount of a pentaaza macrocyclic ring complex corresponding to the Formula (I) below, prior to, concomitantly with, or after administration of the platinum-based anticancer agent, whereby toxic effects of the platinum-based anti-cancer agent are reduced:

(I)

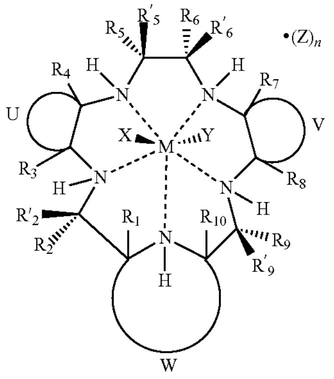

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-NR_{11}R_{12}$, $-COR_{11}$, $-CO_2R_1$, $-CONR_{11}R_{12}$, $-SR_{11}$, $-SOR_{11}$, $-SO_2R$ 11, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Embodiment 31. The method according to Embodiment 30, wherein the subject is afflicted with cancer.

Embodiment 32. The method according to any one of Embodiments 30-31, wherein the subject is suffering from nephrotoxicity and/or myelotoxicity associated with treatment with the platinum-based anti-cancer agent.

Embodiment 33. The method according to any one of Embodiments 30-32, comprising administering therapeutically effective amounts of the platinum-based anti-cancer agent and the pentaaza macrocyclic ring complex that increase treatment response to the platinum-based anti-cancer agent.

Embodiment 34. The method of any of Embodiments 30-33, wherein the pentaaza macrocyclic ring complex is administered in a therapeutically effective amount that results in an increase in cancer response corresponding to any selected from the group consisting of reduced tumor volume, reduced tumor growth rate, increased survival, reduced occurrence and/or extent of metastasis, and reduced proliferation of cancer cells, and/or may decrease cancer complications Embodiment 35. The method of any of Embodiments 30-34, wherein the pentaaza macrocyclic ring is administered in a therapeutically effective amount that reduces levels of at least one of creatine and blood urea nitrogen (BUN).

Embodiment 36. The method of any of Embodiments 30-35, wherein the pentaaza macrocyclic ring is administered in a therapeutically effective amount that reduces levels of markers for kidney damage selected from the group consisting of kidney injury molecule 1 (KIM1) and neutrophil gelatinase-associated lipocalin (NGAL).

Embodiment 37. A method of treating and/or reducing the risk of a toxic effect selected from the group consisting of nephrotoxicity and myelotoxicity associated with treatment with a platinum-based anti-cancer agent in a mammalian subject in need thereof, the method comprising:

administering to the subject a pentaaza macrocyclic ring complex corresponding to the Formula (I) below, prior to, concomitantly with, or after administration of the platinum-based anticancer agent, whereby toxic effects of the platinum-based anti-cancer agent are reduced:

(I)

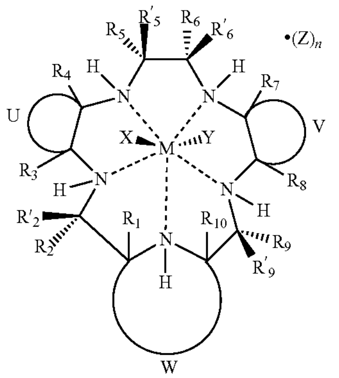

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$NR_{11}R_{12}$, —$COR_{11}$, —$CO_2R_1$, —$CONR_{11}R_{12}$, —$SR_{11}$, —$SOR_{11}$, —$SO_2R$ 11, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Embodiment 38. The method according to Embodiment 37, wherein the subject is afflicted with cancer.

Embodiment 39. The method according to any one of Embodiments 37-38, wherein the subject is suffering from nephrotoxicity and/or myelotoxicity associated with treatment with the platinum-based anti-cancer agent.

Embodiment 40. The method according to any one of Embodiments 37-39, comprising administering therapeutically effective amounts of the platinum-based anti-cancer agent and the pentaaza macrocyclic ring complex that increase treatment response to the platinum-based anti-cancer agent.

Embodiment 41. The method of any one of Embodiments 37-40, wherein the pentaaza macrocyclic ring complex is administered in a therapeutically effective amount that results in an increase in cancer response corresponding to any selected from the group consisting of reduced tumor volume, reduced tumor growth rate, increased survival, reduced occurrence and/or extent of metastasis, and reduced proliferation of cancer cells, and/or may decrease cancer complications.

Embodiment 42. The method of any one of Embodiments 37-41, wherein the pentaaza macrocyclic ring is administered in a therapeutically effective amount that reduces levels of at least one of creatine and blood urea nitrogen (BUN).

Embodiment 43. The method of any one of Embodiments 37-42, wherein the pentaaza macrocyclic ring is administered in a therapeutically effective amount that reduces levels of markers for kidney damage selected from the group consisting of kidney injury molecule 1 (KIM1) and neutrophil gelatinase-associated lipocalin (NGAL).

Embodiment 44. The method according to any preceding Embodiment, wherein $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

Embodiment 45. The method according to any preceding Embodiment, wherein W is an unsubstituted pyridine moiety.

Embodiment 46. The method according to any preceding Embodiment, wherein U and V are transcyclohexanyl fused rings.

Embodiment 47. The method according to any preceding Embodiment, wherein the pentaaza macrocyclic ring complex is represented by Formula (II):

(II)

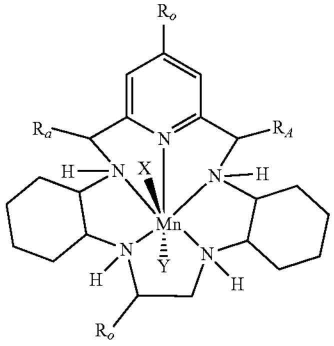

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$—$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Embodiment 48. The method according to any preceding claim, wherein the pentaaza macrocyclic ring complex is represented by Formula (III) or Formula (IV):

(III)

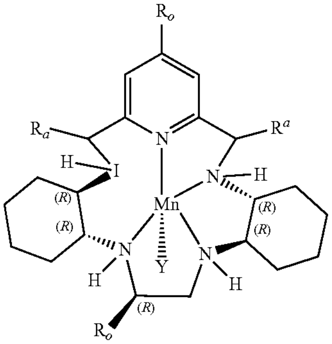

(IV)

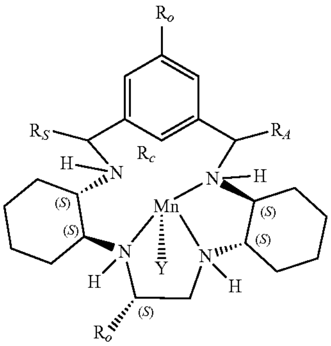

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$NR_{11}R_{12}$, —$COR_{11}$, —$CO_2R_1$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Embodiment 49. The method according to any preceding Embodiment, wherein the pentaaza macrocyclic ring complex is a compound represented by a formula selected from the group consisting of Formulae (V)-(XVI):

(V)

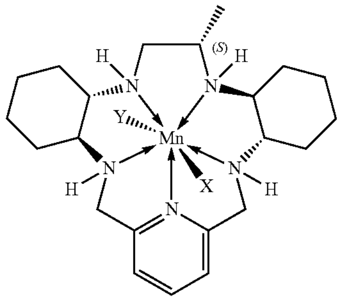

(VI)

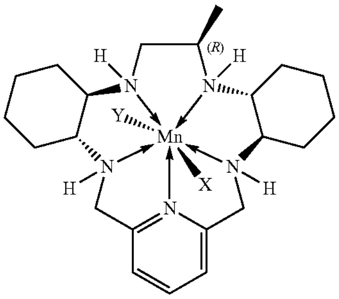

(VII)

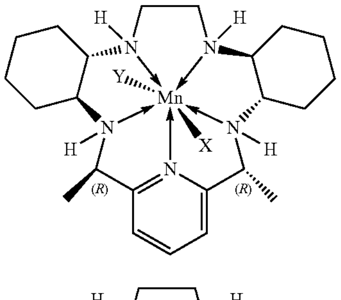

(VIII)

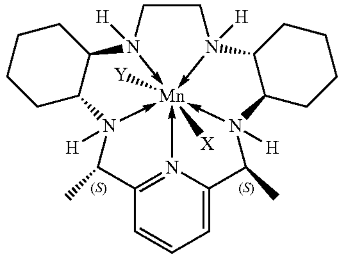

-continued (IX)

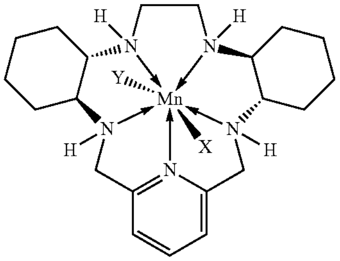

(X)

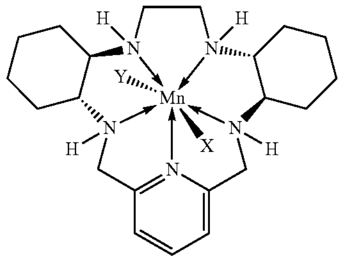

Embodiment 50. The method according to any preceding Embodiment, wherein X and Y are independently selected from substituted or unsubstituted moieties of the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof;

or X and Y correspond to —O—C(O)—$X_1$, where each $X_1$ is —C($X_2$)($X_3$)($X_4$), and each $X_1$ is independently substituted or unsubstituted phenyl or —C(—$X_2$)(—$X_3$)(—$X_4$);

each $X_2$ is independently substituted or unsubstituted phenyl, methyl, ethyl or propyl;

each $X_3$ is independently hydrogen, hydroxyl, methyl, ethyl, propyl, amino, —$X_5$C(═O)$R_{13}$ where $X_5$ is NH or O, and $R_{13}$ is C1-C18 alkyl, substituted or unsubstituted aryl or C1-C18 aralkyl, or —O$R_{14}$, where $R_{14}$ is C1-C18 alkyl, substituted or unsubstituted aryl or C1-C18 aralkyl, or together with $X_4$ is (═O); and each $X_4$ is independently hydrogen or together with $X_3$ is (═O);

or X and Y are independently selected from the group consisting of charge-neutralizing anions which are derived from any monodentate or polydentate coordinating ligand and a ligand system and the corresponding anion thereof;

or X and Y are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$.

Embodiment 51. The method according to any preceding Embodiment, wherein X and Y are independently selected from the group consisting of fluoro, chloro, bromo, and iodo anions.

Embodiment 52. The method according to any preceding Embodiment, wherein X and Y are independently selected from the group consisting of alkyl carboxylates, aryl carboxylates and arylalkyl carboxylates.

Embodiment 53. The method according to any preceding Embodiment, wherein X and Y are independently amino acids.

Embodiment 54. The method according to any preceding Embodiment, wherein the pentaaza macrocyclic ring complex is a compound represented by the formula:

(4419)

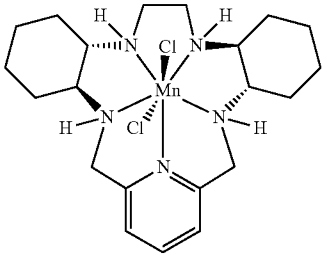

Embodiment 55. The method according to any preceding Embodiment, wherein the pentaaza macrocyclic ring complex is a compound represented by the formula:

(4403)

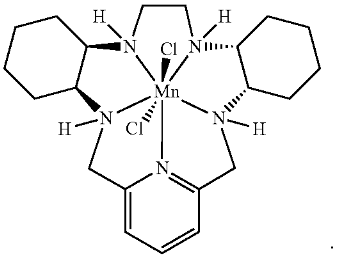

Embodiment 56. The method according to any preceding Embodiment, wherein the pentaaza macrocyclic ring complex is a compound represented by the formula:

(4401)

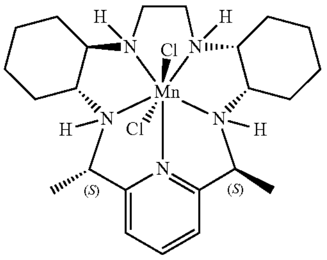

.

Embodiment 57. The method according to any preceding Embodiment, wherein the pentaaza macrocyclic ring complex is represented by the formula:

GC4444

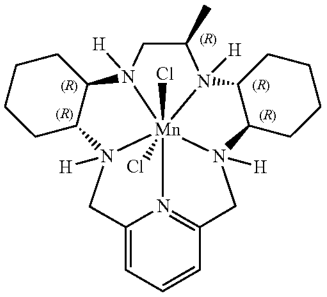

Embodiment 58. The method according to any preceding Embodiment, wherein the pentaaza macrocyclic ring complex is represented by the formula:

GC4702

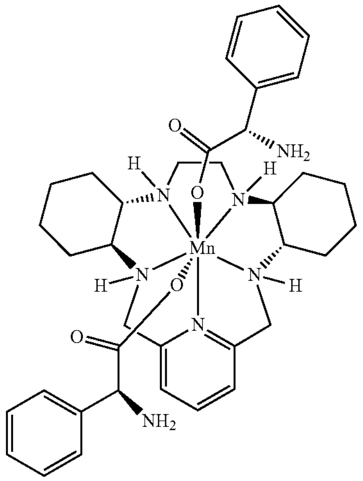

.

Embodiment 59. The method according to any preceding Embodiment, wherein the pentaaza macrocyclic ring complex is represented by the formula:

GC4711

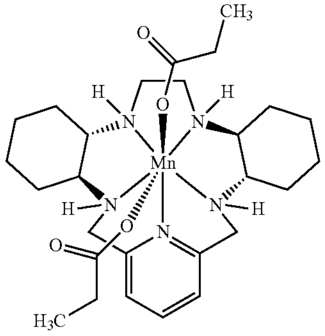

Embodiment 60. The method according to any preceding Embodiment, wherein the platinum-based anticancer agent is one selected from the group consisting of cisplatin, carboplatin, oxaliplatin, nedaplatin, lobaplatin, heptaplatin, dicycloplation, lipoplatin, LA-12, phosphaplatin, phenanthriplatin, ProLindac, triplatin tetranitrate, picoplatin, satraplatin, pyriplantin, and/or a pharmaceutically acceptable salt thereof.

Embodiment 61. The method according to any preceding Embodiment, wherein the platinum-based anti-cancer agent comprises cisplatin.

Embodiment 62. The method according to any preceding Embodiment, wherein the platinum-based anticancer agent is administered at a dosage in the range of 20 $mg/m^2$ to 200 $mg/m^2$.

Embodiment 63. The method according to any preceding Embodiment, wherein administration of the pentaaza macrocyclic ring complex in a course of therapy is administered a predetermined period of time before administration of the platinum-based anti-cancer agent.

Embodiment 64. The method according to any preceding Embodiment, wherein administration of the pentaaza macrocyclic ring complex in a course of therapy is administered at least one week, one day or one hour before administration of the platinum-based anti-cancer agent.

Embodiment 65. The method according to any preceding Embodiment, wherein administration of the pentaaza macrocyclic ring complex in a course of therapy is administered no more than 1 hour before, and/or simultaneously with, administration of the platinum-based anti-cancer agent.

Embodiment 66. The method according to any preceding Embodiment, wherein administration of the pentaaza macrocyclic ring complex in a course of therapy is administered no more than 1 hour, 1 day or 1 week after administration of the platinum-based anti-cancer agent.

Embodiment 67. The method according to any preceding Embodiment, comprising administering the platinum based anti-cancer agent to a subject that is concurrently receiving radiation therapy.

Embodiment 68. The method according to any one of Embodiments 1-66, comprising administering the platinum based anti-cancer agent and pentaaza macrocyclic ring complex to a subject that is not receiving radiation therapy.

Embodiment 69. The method according to any one of Embodiments 1-66, wherein a course of therapy comprising administration of the pentaaza macrocyclic ring complex and the platinum-based anti-cancer agent, is administered to a subject that does not receive radiation therapy during the course of therapy.

Embodiment 70. The method according to any one of Embodiments 1-66, comprising administering one or more of the pentaaza macrocyclic ring complex and the platinum-based anti-cancer agent to the subject on a day other than a day that the subject is receiving radiation therapy.

Embodiment 71. The method according to any one of Embodiments 1-66, comprising administering a course of therapy comprising administration of the platinum-based anti-cancer agent and the pentaaza macrocyclic ring complex to a subject that has not received radiation therapy for at least a day.

Embodiment 72. The method according to any one of Embodiments 1-66, comprising administering a course of therapy comprising administration of the platinum-based anti-cancer agent and the pentaaza macrocyclic ring complex to a subject that has not received radiation therapy for at least a week.

Embodiment 73. The method according to any one of Embodiments 1-66, comprising administering a course of therapy comprising administration of the platinum-based anti-cancer agent and the pentaaza macrocyclic ring complex to a subject that has not received radiation therapy for at least a month.

Embodiment 74. The method according to any one of Embodiments 1-66, comprising administering a course of therapy comprising administration of the platinum-based anti-cancer agent and the pentaaza macrocyclic ring complex to a subject that has not received radiation therapy for at least six months.

Embodiment 75. The method according to any one of Embodiments 1-66, comprising administering the platinum-based anti-cancer agent and pentaaza macrocyclic ring complex to a subject, and delaying any radiation therapy optionally administered to the subject thereafter by at least one day after a final administration of the pentaaza macrocyclic ring complex.

Embodiment 76. The method according to any one of Embodiments 1-66, comprising administering the platinum-based anti-cancer agent and pentaaza macrocyclic ring complex to a subject, and delaying any radiation therapy optionally administered to the subject thereafter by at least one week after a final administration of the pentaaza macrocyclic ring complex.

Embodiment 77. The method according to any one of Embodiments 1-66, comprising administering the platinum-based anti-cancer agent and pentaaza macrocyclic ring complex to a subject, and delaying any radiation therapy optionally administered to the subject thereafter by at least one month after a final administration of the pentaaza macrocyclic ring complex.

Embodiment 78. The method according to any one of Embodiments 1-66, comprising administering the platinum-based anti-cancer agent and the pentaaza macrocyclic ring complex to a subject, and delaying any radiation therapy optionally administered to the subject thereafter by at least six months after a final administration of the pentaaza macrocyclic ring complex.

Embodiment 79. The method according to any preceding claim, wherein the cancer is selected from the group consisting of breast cancer, non-small-cell lung cancer, melanoma, renal cell carcinoma, urothelial carcinoma, bladder cancer, pancreatic cancer, head and neck cancers, colorectal cancer, prostate cancer, brain cancer, spindle cell carcinoma, and oral squamous cell carcinoma.

Embodiment 80. The method according to any preceding Embodiment, wherein the cancer is selected from the group consisting of breast cancer, lung cancer, renal cell carcinoma, spindle cell carcinoma, colorectal cancer, oral squamous cell carcinoma, and head and neck cancer.

Embodiment 81. The method according to any preceding Embodiment, wherein the cancer is at least one of lung cancer and head and neck cancer.

Embodiment 82. The method according to any preceding Embodiment, wherein the pentaaza macrocyclic ring complex is administered to the subject in a dose in a range of from 0.2 mg/kg to 40 mg/kg.

Embodiment 83. The method according to any preceding Embodiment, wherein the pentaaza macrocyclic ring complex is administered to the subject in a dose in a range of from 0.2 mg/kg to 24 mg/kg.

Embodiment 84. The method according to any preceding Embodiment, wherein the pentaaza macrocyclic ring complex is administered to the subject in a dose in a range of from 0.2 mg/kg to 10 mg/kg.

Embodiment 85. The method according to any preceding Embodiment, wherein the pentaaza macrocyclic ring complex is administered via at least one of parenteral route and oral route.

Embodiment 86. The method according to any preceding Embodiment, wherein the pentaaza macrocyclic ring complex is administered intraperitoneally or intravenously.

Embodiment 87. The method according to any preceding Embodiment, wherein the subject is a human.

Embodiment 88. A kit for treating cancer and/or reducing the toxic effects of a platinum-based anti-cancer agent in a mammalian subject in need thereof, the kit comprising:

a platinum-based anti-cancer agent;

a pentaaza macrocyclic ring complex corresponding to Formula (I) below: and instructions for administering a therapeutically effective amount of the platinum anti-cancer agent and a therapeutically effective amount of the pentaaza macrocyclic ring complex to perform a method according to any of the preceding claims, wherein the pentaaza macrocyclic ring complex according to Formula (I) is as follows:

(I)

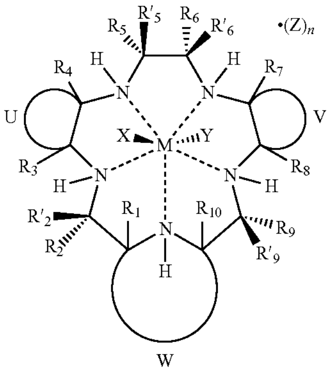

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $—NR_{11}R_{12}$, $—COR_{11}$, $—CO_2R_1$, $—CONR_{11}R_{12}$, $—SR_{11}$, $—SOR_{11}$, $—SO_2R_{11}$, $—SO_2NR_{11}R_{12}$, $—N(OR_{11})(R_{12})$, $—P(O)(OR_{11})(OR_{12})$, $—P(O)(OR_{11})(R_{12})$, and $—OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

What is claimed is:

1. A method of treating and/or reducing a risk of a nephrotoxic effect associated with treatment with a platinum-based anti-cancer agent in a mammalian subject afflicted with cancer in need thereof, the method consisting essentially of:

administering to the subject a therapeutically effective amount of a platinum-based anticancer agent; and administering to the subject a therapeutically effective amount of a pentaaza macrocyclic ring complex corresponding to the formula below, prior to, concomitantly with, or after administration of the platinum-based anticancer agent, whereby the nephrotoxic effect of the platinum-based anti-cancer agent is reduced:

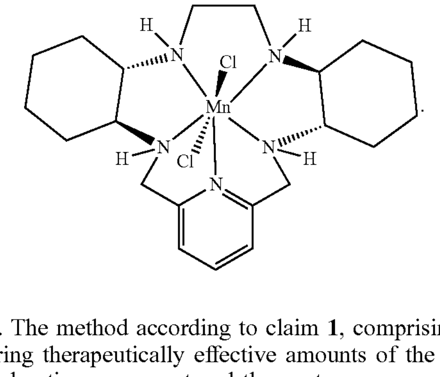

2. The method according to claim 1, comprising administering therapeutically effective amounts of the platinum-based anti-cancer agent and the pentaaza macrocyclic ring complex that increase treatment response to the platinum-based anti-cancer agent.

3. The method according to claim 1, wherein the pentaaza macrocyclic ring complex is administered in a therapeutically effective amount that results in an increase in cancer response corresponding to any selected from the group consisting of reduced tumor volume, reduced tumor growth rate, increased survival, reduced occurrence and/or extent of metastasis, and reduced proliferation of cancer cells, and/or may decrease cancer complications.

4. The method according to claim 1, wherein the pentaaza macrocyclic ring is administered in a therapeutically effective amount that reduces levels of at least one of creatine and blood urea nitrogen (BUN).

5. The method according to claim 1, wherein the pentaaza macrocyclic ring is administered in a therapeutically effective amount that reduces levels of markers for kidney damage selected from the group consisting of kidney injury molecule 1 (KIM1) and neutrophil gelatinase-associated lipocalin (NGAL).

6. A method of treating and/or reducing a risk of a nephrotoxic effect associated with treatment with a platinum-based anti-cancer agent in a mammalian subject afflicted with cancer in need thereof, the method consisting essentially of:

administering to the subject a pentaaza macrocyclic ring complex corresponding to the formula below, prior to, concomitantly with, or after administration of the platinum-based anticancer agent, whereby the nephrotoxic effect of the platinum-based anti-cancer agent is reduced:

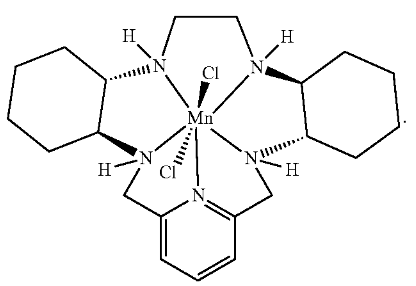

7. The method according to claim 6, comprising administering therapeutically effective amounts of the platinum-based anti-cancer agent and the pentaaza macrocyclic ring complex that increase treatment response to the platinum-based anti-cancer agent.

8. The method according to claim 6, wherein the pentaaza macrocyclic ring complex is administered in a therapeutically effective amount that results in an increase in cancer response corresponding to any selected from the group consisting of reduced tumor volume, reduced tumor growth rate, increased survival, reduced occurrence and/or extent of metastasis, and reduced proliferation of cancer cells, and/or may decrease cancer complications.

9. The method according to claim 6, wherein the pentaaza macrocyclic ring is administered in a therapeutically effective amount that reduces levels of at least one of creatine and blood urea nitrogen (BUN).

10. The method according to claim 6, wherein the pentaaza macrocyclic ring is administered in a therapeutically effective amount that reduces levels of markers for kidney damage selected from the group consisting of kidney injury molecule 1 (KIM1) and neutrophil gelatinase-associated lipocalin (NGAL).

11. The method according to claim 6, wherein the platinum-based anticancer agent is one selected from the group consisting of cisplatin, carboplatin, oxaliplatin, nedaplatin, lobaplatin, heptaplatin, dicycloplation, lipoplatin, LA-12, phosphaplatin, phenanthriplatin, ProLindac, triplatin tetranitrate, picoplatin, satraplatin, pyriplantin, and/or a pharmaceutically acceptable salt thereof.

12. The method according to claim 6, wherein the platinum-based anti-cancer agent is cisplatin.

13. The method according to claim 6, wherein the platinum-based anticancer agent is administered at a dosage in the range of 20 $mg/m^2$ to 200 $mg/m^2$.

14. The method according to claim 6, wherein administration of the pentaaza macrocyclic ring complex in a course of therapy is administered a predetermined period of time before administration of the platinum-based anti-cancer agent.

15. The method according to claim 6, wherein administration of the pentaaza macrocyclic ring complex in a course of therapy is administered at least one week, one day or one hour before administration of the platinum-based anti-cancer agent.

16. The method according to claim 6, wherein administration of the pentaaza macrocyclic ring complex in a course of therapy is administered no more than 1 hour before, and/or simultaneously with, administration of the platinum-based anti-cancer agent.

17. The method according to claim 6, wherein administration of the pentaaza macrocyclic ring complex in a course of therapy is administered no more than 1 hour, 1 day or 1 week after administration of the platinum-based anti-cancer agent.

18. The method according to claim 1, wherein the cancer is selected from the group consisting of breast cancer, non-small-cell lung cancer, melanoma, renal cell carcinoma, urothelial carcinoma, bladder cancer, pancreatic cancer, head and neck cancers, colorectal cancer, prostate cancer, brain cancer, spindle cell carcinoma, and oral squamous cell carcinoma.

19. The method according to claim 1, wherein the cancer is selected from the group consisting of breast cancer, lung cancer, renal cell carcinoma, spindle cell carcinoma, colorectal cancer, oral squamous cell carcinoma, and head and neck cancer.

20. The method according to claim 1, wherein the cancer is at least one of lung cancer and head and neck cancer.

21. The method according to claim 1, wherein the pentaaza macrocyclic ring complex is administered to the subject in a dose in a range of from 0.2 mg/kg to 40 mg/kg.

22. The method according to claim 1, wherein the pentaaza macrocyclic ring complex is administered to the subject in a dose in a range of from 0.2 mg/kg to 24 mg/kg.

23. The method according to claim 1, wherein the pentaaza macrocyclic ring complex is administered to the subject in a dose in a range of from 0.2 mg/kg to 10 mg/kg.

24. The method according to claim 1, wherein the pentaaza macrocyclic ring complex is administered via at least one of parenteral route and oral route.

25. The method according to claim 1, wherein the pentaaza macrocyclic ring complex is administered intraperitoneally or intravenously.

26. The method according to claim 1, wherein the subject is a human.

27. The method according to claim 1, wherein the platinum-based anticancer agent is cisplatin.

28. The method according to claim 1, wherein the platinum-based anticancer agent is carboplatin.

29. The method according to claim 1, wherein the platinum-based anticancer agent is oxaliplatin.

30. The method according to claim 6, wherein the platinum-based anticancer agent is carboplatin.

31. The method according to claim 6, wherein the platinum-based anticancer agent is oxaliplatin.

* * * * *